US005707747A

United States Patent [19]

Tomiyama et al.

[11] Patent Number: 5,707,747
[45] Date of Patent: Jan. 13, 1998

[54] AMINE COMPOUND AND ELECTRO-LUMINESCENCE DEVICE COMPRISING SAME

[75] Inventors: Hiromitsu Tomiyama; Masahiko Oshino; Ikuko Ihara; Naoko Nakanishi, all of Ibaraki; Mutsumi Suzuki; Masao Fukuyama, both of Kanagawa; Mutsuaki Murakami; Taro Nambu, both of Tokyo, all of Japan

[73] Assignees: Hodogaya Chemical Co., Ltd., Tokyo; Matsushita Electric Industrial Co., Ltd., Kadoma, both of Japan

[21] Appl. No.: 738,326

[22] Filed: Oct. 25, 1996

Related U.S. Application Data

[62] Division of Ser. No. 332,726, Nov. 1, 1994, Pat. No. 5,639,914.

[30] Foreign Application Priority Data

| Nov. 1, 1993 | [JP] | Japan | 5-273883 |
| Nov. 1, 1993 | [JP] | Japan | 5-293800 |
| Nov. 1, 1993 | [JP] | Japan | 5-293801 |
| Jun. 15, 1994 | [JP] | Japan | 6-132744 |
| Jun. 15, 1994 | [JP] | Japan | 6-155470 |
| Sep. 30, 1994 | [JP] | Japan | 6-236622 |
| Sep. 30, 1994 | [JP] | Japan | 6-259688 |

[51] Int. Cl.$^6$ ............................................. C07C 211/55
[52] U.S. Cl. ...................... 428/457; 257/40; 257/103; 313/498; 313/504; 313/506; 313/509; 428/411.1; 428/461; 428/515; 428/917; 430/59; 430/72; 430/76; 552/110; 564/50; 564/309
[58] Field of Search ........................ 428/411.1, 457, 428/461, 515, 917; 313/498, 504, 506, 509; 430/59, 72, 76; 564/50, 309; 552/110; 257/40, 103

[56] References Cited

U.S. PATENT DOCUMENTS

| 4,588,666 | 5/1986 | Stolka et al. ................... 430/59 |
| 4,720,432 | 1/1988 | Vanslyke et al. ................ 428/457 |
| 4,833,054 | 5/1989 | Akasaki et al. ................. 430/59 |
| 5,482,822 | 1/1996 | Mihara et al. ............... 430/270.14 |

FOREIGN PATENT DOCUMENTS

| 5-239455 | 9/1993 | Japan . |
| 6-199745 | 7/1995 | Japan ........................ 564/309 |

OTHER PUBLICATIONS

Tang et al., Appl. Phys. Lett., vol. 51, No. 12, pp. 913–915, Oct. 1987.

DATABASE WPI, Derwent Publications Ltd., AN 91-187965, JP-A-2 234 394, Oct. 1990.

Nakaya et al., Chemical Abstracts, vol. 123, abstract 270294, 1995.

*Primary Examiner*—Richard L. Raymond
*Attorney, Agent, or Firm*—Oblon, Spivak, McClelland, Maier & Neustadt, P.C.

[57] ABSTRACT

The present invention provides novel amine compounds useful as electron-transporting materials to be incorporated in organic electro-luminescence devices. More particularly, the present invention provides an organic electro-luminescence device (organic EL device) which can find wide application in various display units, requires a low applied voltage and exhibits a high luminance and an excellent stability.

5 Claims, 10 Drawing Sheets

AMINE COMPOUND AND ELECTRO-LUMINESCENCE DEVICE COMPRISING SAME

This is a Division of application Ser. No. 08/332,726 filed Nov. 1, 1994, now U.S. Pat. No. 5,639,914.

FIELD OF THE INVENTION

The present invention relates to novel amine compounds useful as hole-transporting materials to be incorporated in organic electro-luminescence devices. Furthermore, the present invention relates to an organic electro-luminescence device (organic EL device) which can find wide application in various display units, requires a low applied voltage and exhibits a high luminance and an excellent stability.

BACKGROUND OF THE INVENTION

Since an electro-luminescence device can emit light itself, it is capable of providing a brighter and sharper display than liquid crystal device. Thus, the electro-luminescence device has long been studied by many scholars. Hitherto, an electro-luminescence device comprising an inorganic material ZnS has been made practicable. However, such an inorganic electro-luminescence device requires an applied voltage of not lower than 200 V to emit light and thus cannot find wide application.

On the other hand, the organic electro-luminescence device comprising an organic material, though having heretofore been far from practicable, can enjoy rapid progress in its properties made by a laminated structure developed by C. W. Tang et al. of Kodak Corporation in 1987. They developed a laminate of an organic fluorescent substance, an organic material capable of transporting carriers (carrier transporting layer) and an electrode. Both holes and electrons injected from the respective electrodes were injected into the fluorescent substance, resulting in a successful emission of light. Thus, the light emission efficiency of the organic EL device was enhanced. Many scholars have made studies to enhance the properties of organic EL device, and at present, a luminescence of not lower than 10,000 cd/m² can be obtained.

As the organic fluorescent substance which can be used for an organic EL device having a laminate structure there has been used a fluorescent organic dye such as tris-8-quinolinol aluminum complex (Alq) and coumarin. As the carrier-transporting material there have been studied various compounds well known as organic materials for electrophotographic photoreceptor. Examples of such compounds include diamine compounds such as N,N'-di(m-tolyl)-N,N'-diphenylbenzidine (TPD) and 1,1-bis[N,N-di(p-tolyl) aminophenyl]cyclohexane (TPAC), and hydrazone compounds such as 4-(N,N-diphenyl)aminobenzaldehyde-N,N-diphenylhydrazone. Further, porphyrin compounds such as copper phthalocyanine may be used.

The basic luminescence of such an organic EL device is high enough to make the product practicable. The impracticability of the organic EL device is mainly responsible for (1) the lack of stability luminescence on operation, and (2) the lack of storage stability. The deterioration in operation as used herein means the drop of luminance, occurrence of a region which emits no light, i.e., dark spot, or destruction due to device shortcircuit during operation where an electric current is applied to the device. The storage stability as used herein means the stability of luminescence during the storage of the device.

In order to eliminate these difficulties of organic EL devices in luminescence stability and storage stability, the inventors have made studies of the mechanism of deterioration of organic EL devices. As a result, it was found that the deterioration of the properties of organic EL devices is mainly responsible for the properties of a carrier-transporting layer. In some detail, it was found that a commonly used hole-transporting material such as those described above (1) crystallizes due to moisture, temperature or current to give unevenly shaped thin film, (2) denatures with the passage of current, or (3) deteriorates its adhesive property to a substrate and a light-emitting layer, causing a remarkable deterioration of the luminescence of the organic EL device.

SUMMARY OF THE INVENTION

It is therefore an object of the present invention to provide a novel amine compound useful as a hole-transporting material which can realize an organic electro-luminescence device excellent in luminescence stability and storage stability.

Such a hole-transporting material is required to:

(1) have an excellent capability of transporting holes;

(2) be thermally stable to maintain a stable glass state;

(3) be able to form a thin film;

(4) be electrically and chemically stable.

It is another object of the present invention to provide an organic EL device excellent in luminescence stability and storage stability using such a hole-transporting material.

These and other objects of the present invention will become more apparent from the following detailed description and examples.

The foregoing objects of the present invention are accomplished with amine compounds represented by the following formulae (I) to (V):

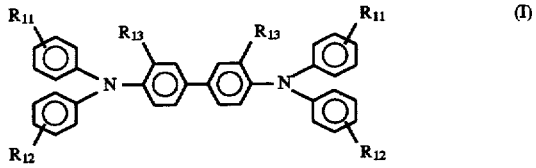

wherein $R_{11}$ and $R_{12}$ may be the same or different and each represent a hydrogen atom, a lower alkyl group, a lower alkoxy group, an unsubstituted phenyl group, or a phenyl group having a lower alkyl group or a lower alkoxy group as a substituent(s), with the proviso that at least one of $R_{11}$ and $R_{12}$ is a normal butyl group, an isobutyl group, a secondary butyl group, a tertiary butyl group, a phenyl group, or a phenyl group having a lower alkyl group or a lower alkoxy group; and $R_{13}$ represents a hydrogen atom, a lower alkyl group (preferably a methyl group), a lower alkoxy group (preferably a methoxy group) or a chlorine atom:

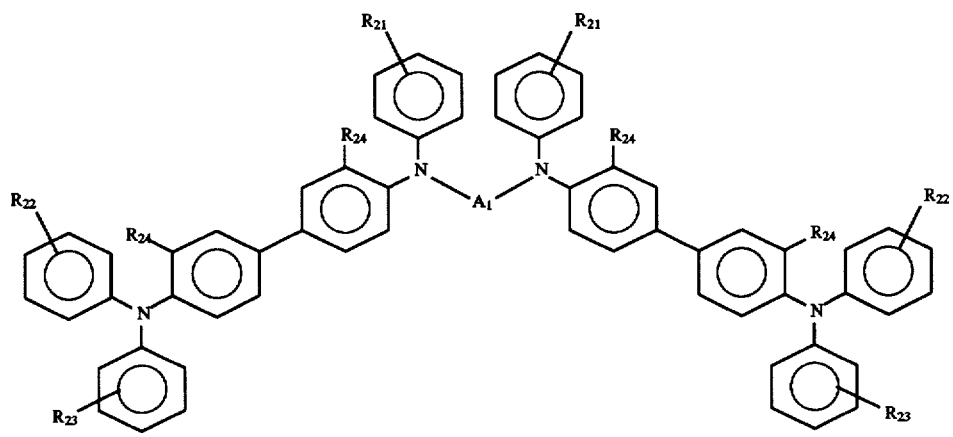

wherein $R_{21}$, $R_{22}$ and $R_{23}$ may be the same or different and each represent a hydrogen atom, a lower alkyl group, a lower alkoxy group, an unsubstituted phenyl group, or a phenyl group having a lower alkyl group or a lower alkoxy group as a substituent(s); $R_{24}$ represents a hydrogen atom, a lower alkyl group (preferably a methyl group), a lower alkoxy group (preferably a methoxy group) or a chlorine atom; and $A_1$ represents a group represented by any one of the following structural formulae (a1) to (i1);

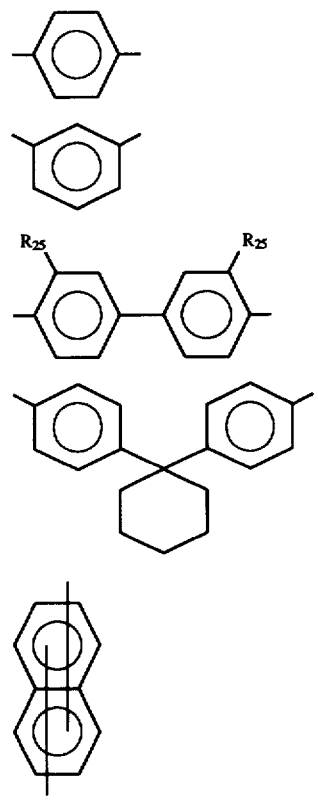

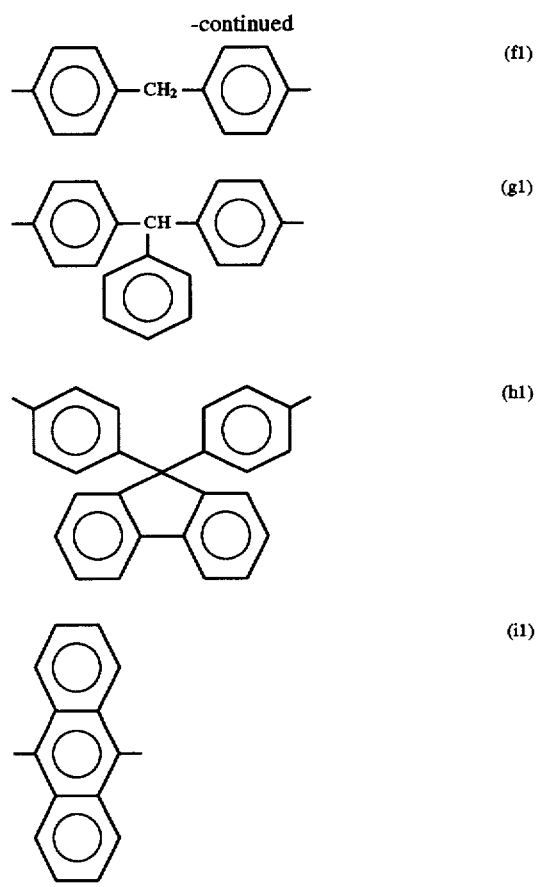

(in which $R_{25}$ represents a hydrogen atom, a lower alkyl group (preferably a methyl group), a lower alkoxy group (preferably a methoxy group) or a chlorine atom):

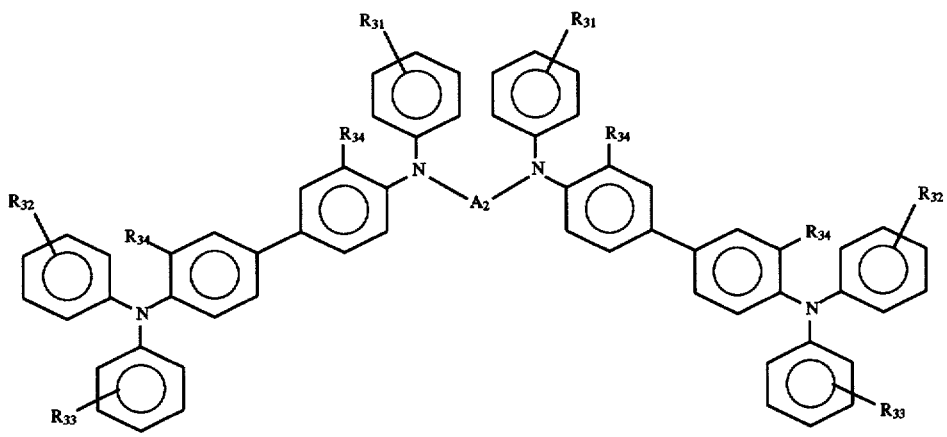

wherein $R_{31}$, $R_{32}$ and $R_{33}$ may be the same or different and each represent a hydrogen atom, a lower alkyl group, a lower alkoxy group, an unsubstituted phenyl group, or a phenyl group having a lower alkyl group or a lower alkoxy group as a substituent(s); $R_{34}$ represents a hydrogen atom, a lower alkyl group (preferably a methyl group), a lower alkoxy group (preferably a methoxy group) or a chlorine atom; and $A_2$ represents a group represented by any one of the following formulae (j1) to (n1);

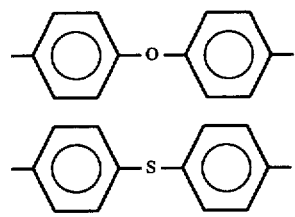

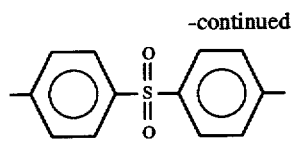

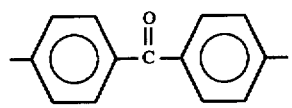

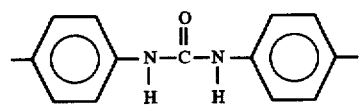

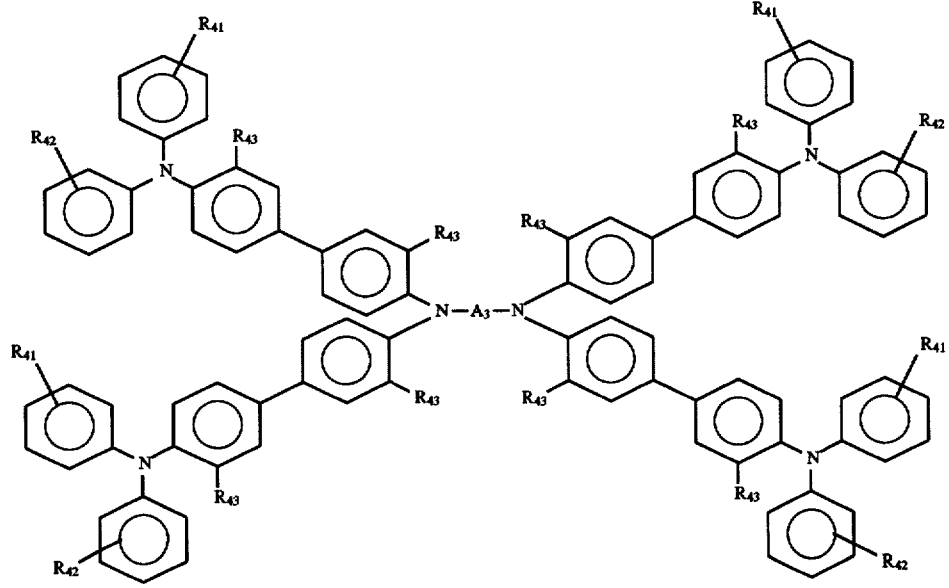

wherein $R_{41}$ and $R_{42}$ may be the same or different and each represent a hydrogen atom, a lower alkyl group, a lower alkoxy group, an unsubstituted phenyl group, or a phenyl group having a lower alkyl group or a lower alkoxy group as a substituent(s); $R_{43}$ represents a hydrogen atom, a lower alkyl group (preferably a methyl group), a lower alkoxy group (preferably a methoxy group) or a chlorine atom; and $A_3$ represents a group represented by any one of the following structural formulae (a2) to (i2):

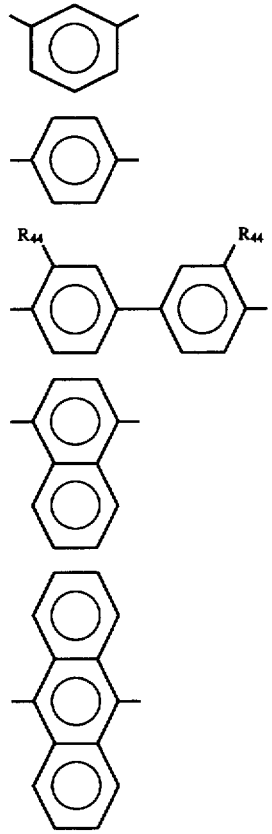

(a2)

(b2)

(c2)

(d2)

(e2)

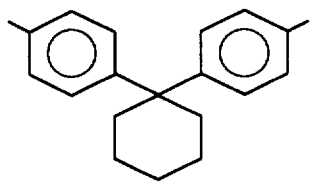

(f2)

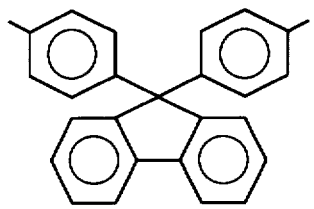

(g2)

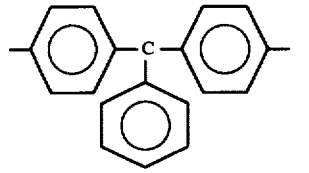

(h2)

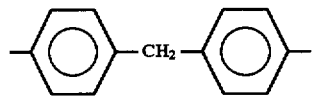

(i2)

(in which $R_{44}$ represents a hydrogen atom, a lower alkyl group (preferably a methyl group), a lower alkoxy group (preferably a methoxy group) or a chlorine atom):

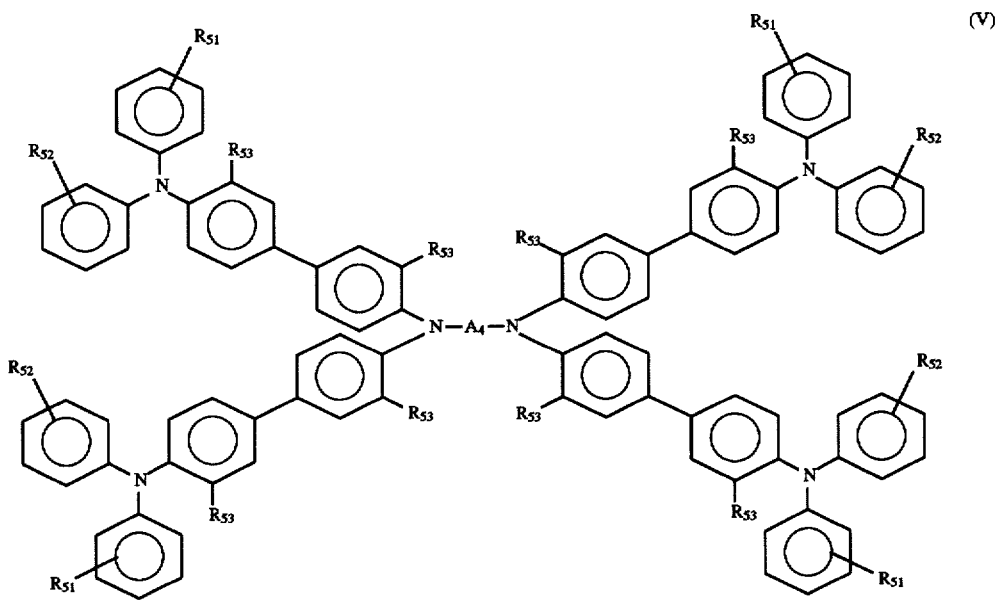

(V)

wherein $R_{51}$ and $R_{52}$ may be the same or different and each represent a hydrogen atom, a lower alkyl group, a lower alkoxy group, an unsubstituted phenyl group, or a phenyl group having a lower alkyl group or a lower alkoxy group as a substituent(s); $R_{53}$ represents a hydrogen atom, a lower alkyl group (preferably a methyl group), a lower alkoxy group (preferably a methoxy group) or a chlorine atom; and $A_4$ represents a group represented by any one of the following structural formulae (j2) to (n2);

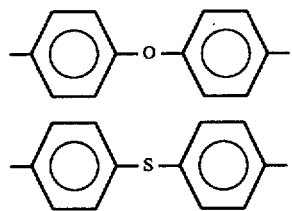

(j2)

(k2)

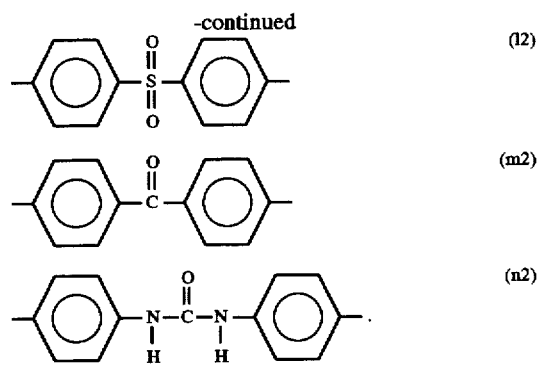

(l2)

(m2)

(n2)

The objects of the present invention are also accomplished with an electro-luminescence device comprising at least one of the compounds represented by the above-described formulae (I) to (V) and the following formula (VI):

(VI)

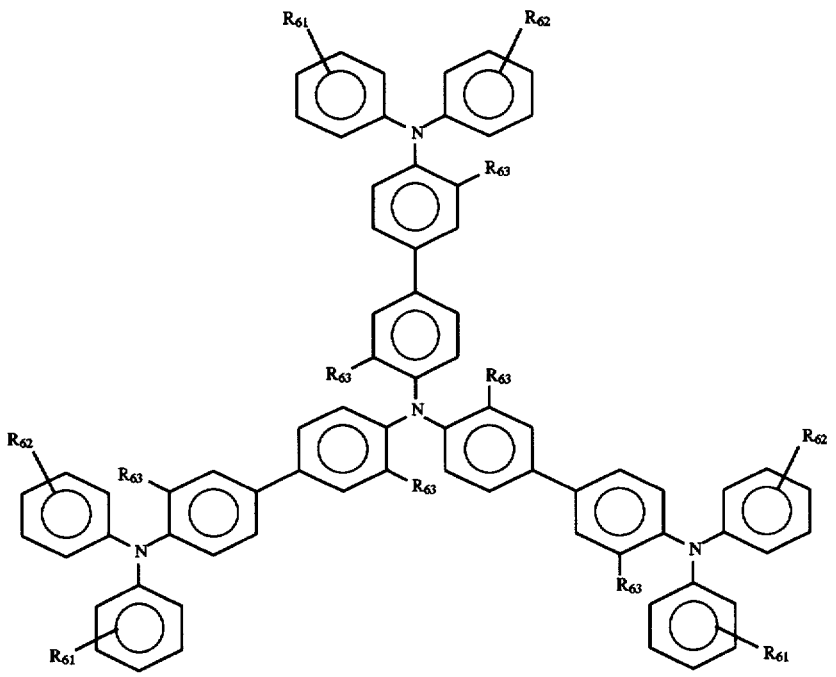

wherein $R_{61}$ and $R_{62}$ may be the same or different and each represent a hydrogen atom, a lower alkyl group, a lower alkoxy group, an unsubstituted phenyl group, or a phenyl group having a lower alkyl group or a lower alkoxy group as a substituent(s); and $R_{63}$ represents a hydrogen atom, a lower alkyl group (preferably a methyl group), a lower alkoxy group (preferably a methoxy group) or a chlorine atom.

The terms "lower alkyl group" and "lower alkoxy group" as used herein mean "$C_{1-4}$ alkyl group" and "$C_{1-4}$ alkoxy group", respectively.

BRIEF DESCRIPTION OF THE DRAWINGS

By way of example and to make the description more clear, reference is made to the accompanying drawings in which.

DETAILED DESCRIPTION OF THE INVENTION

Figure 1:
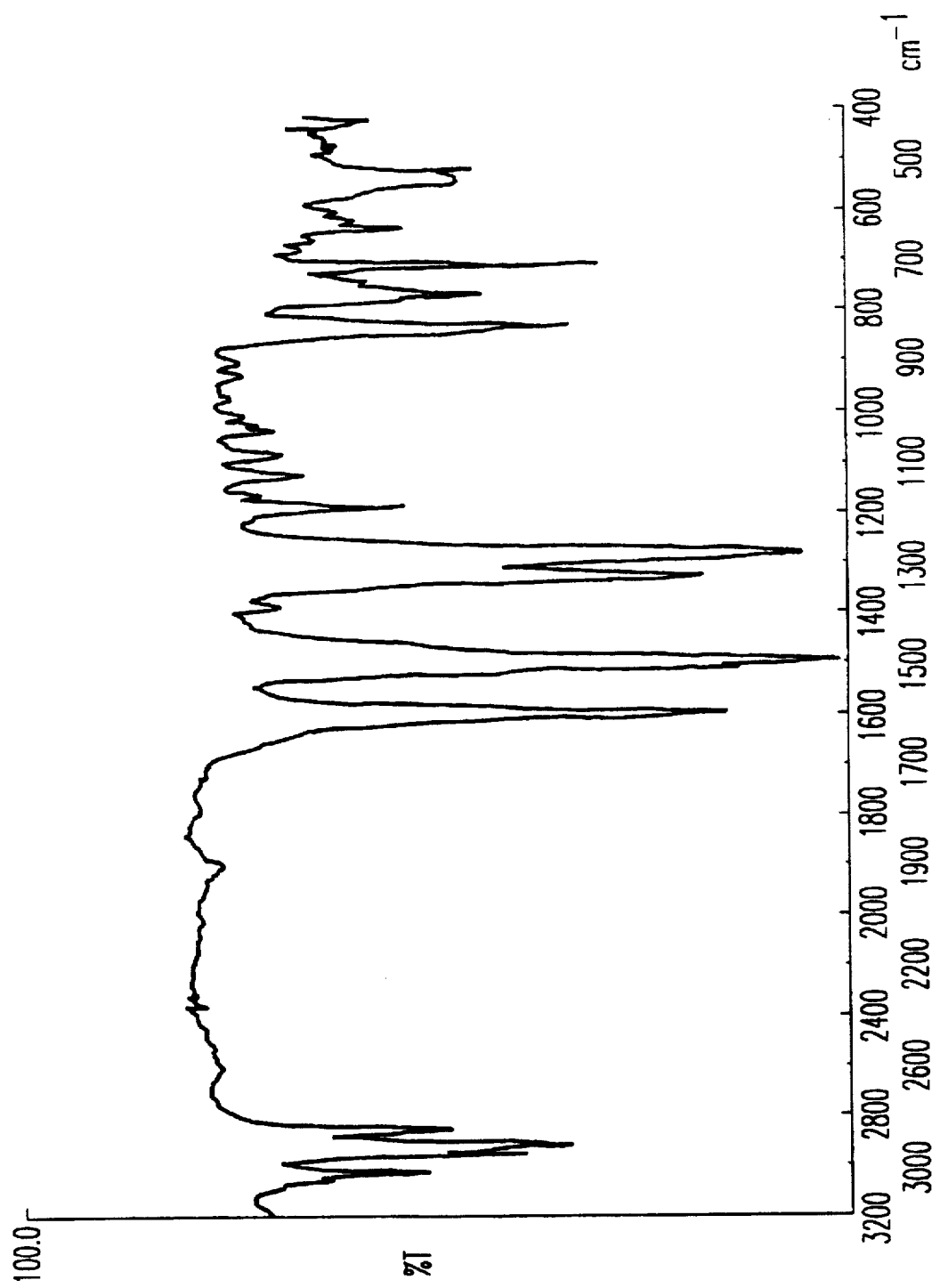
FIG. 1 shows IR spectrum of N,N'-bis(p-normalbutylphenyl)-N,N'-diphenylbenzidine.
Figure 2:
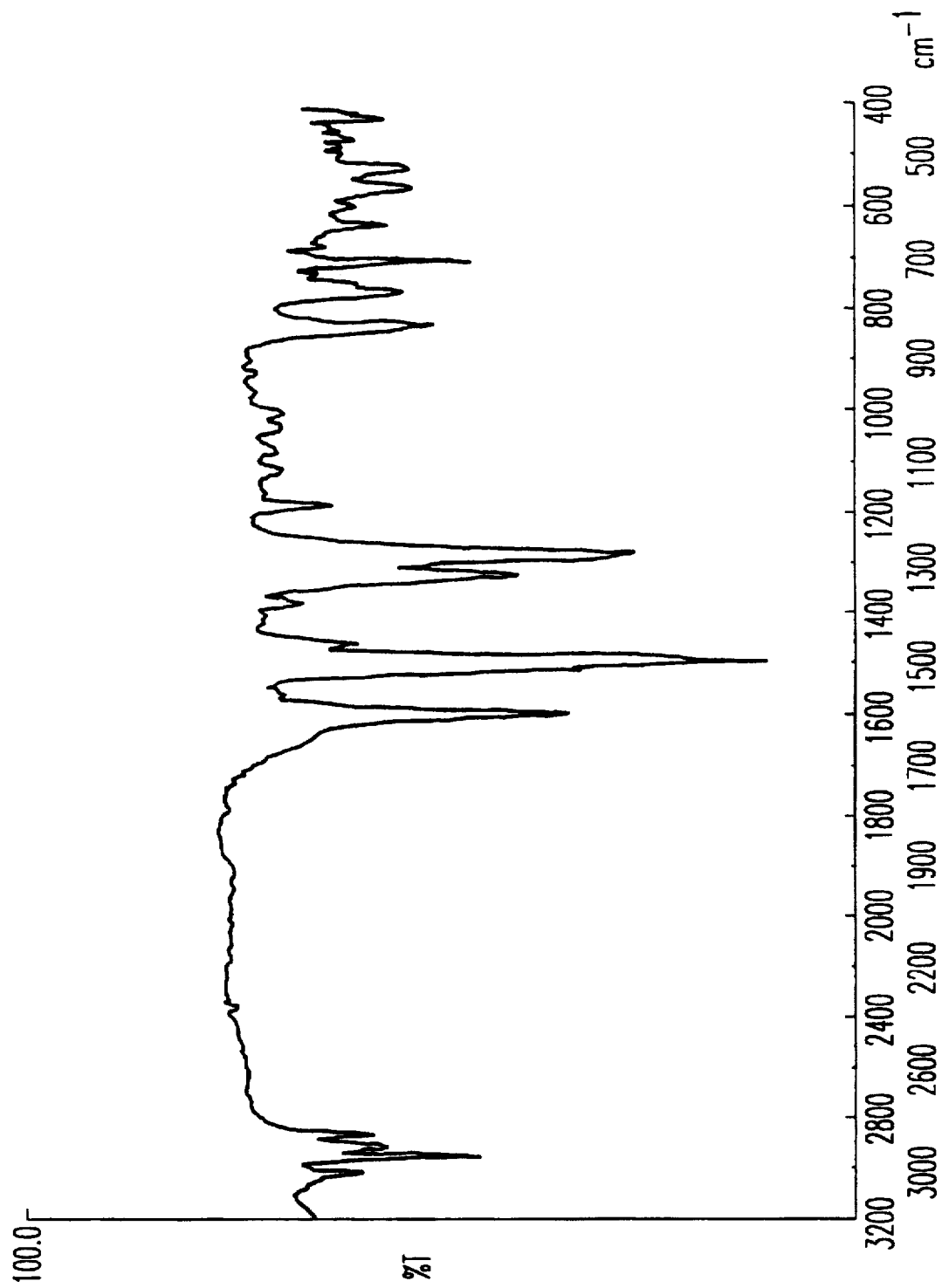
FIG. 2 shows IR spectrum of N,N'-bis(p-isobutylphenyl)-N,N'-diphenylbenzidine.
Figure 3:
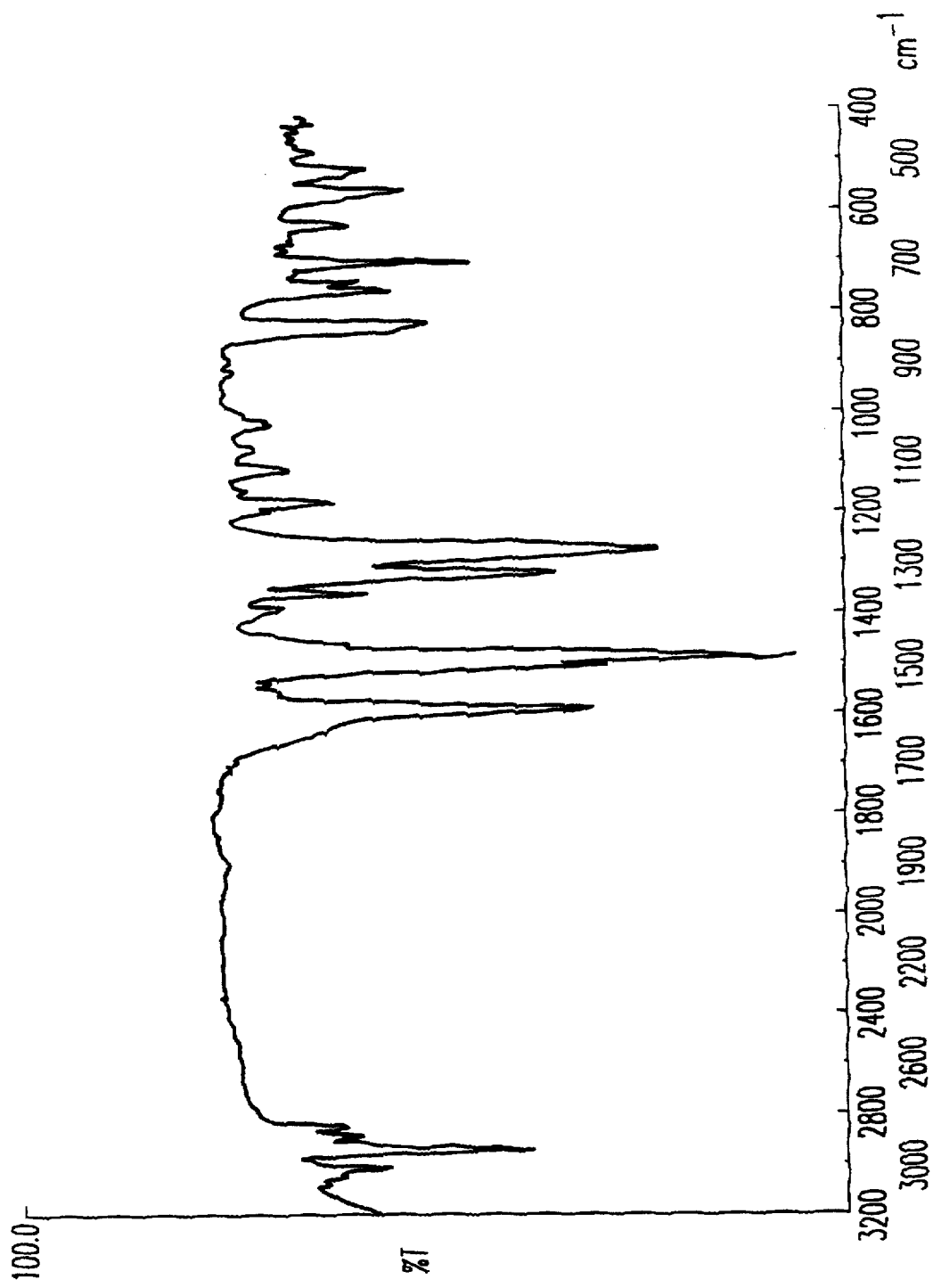
FIG. 3 shows IR spectrum of N,N'-bis(p-tertiarybutylphenyl)-N,N'-diphenylbenzidine.
Figure 4:
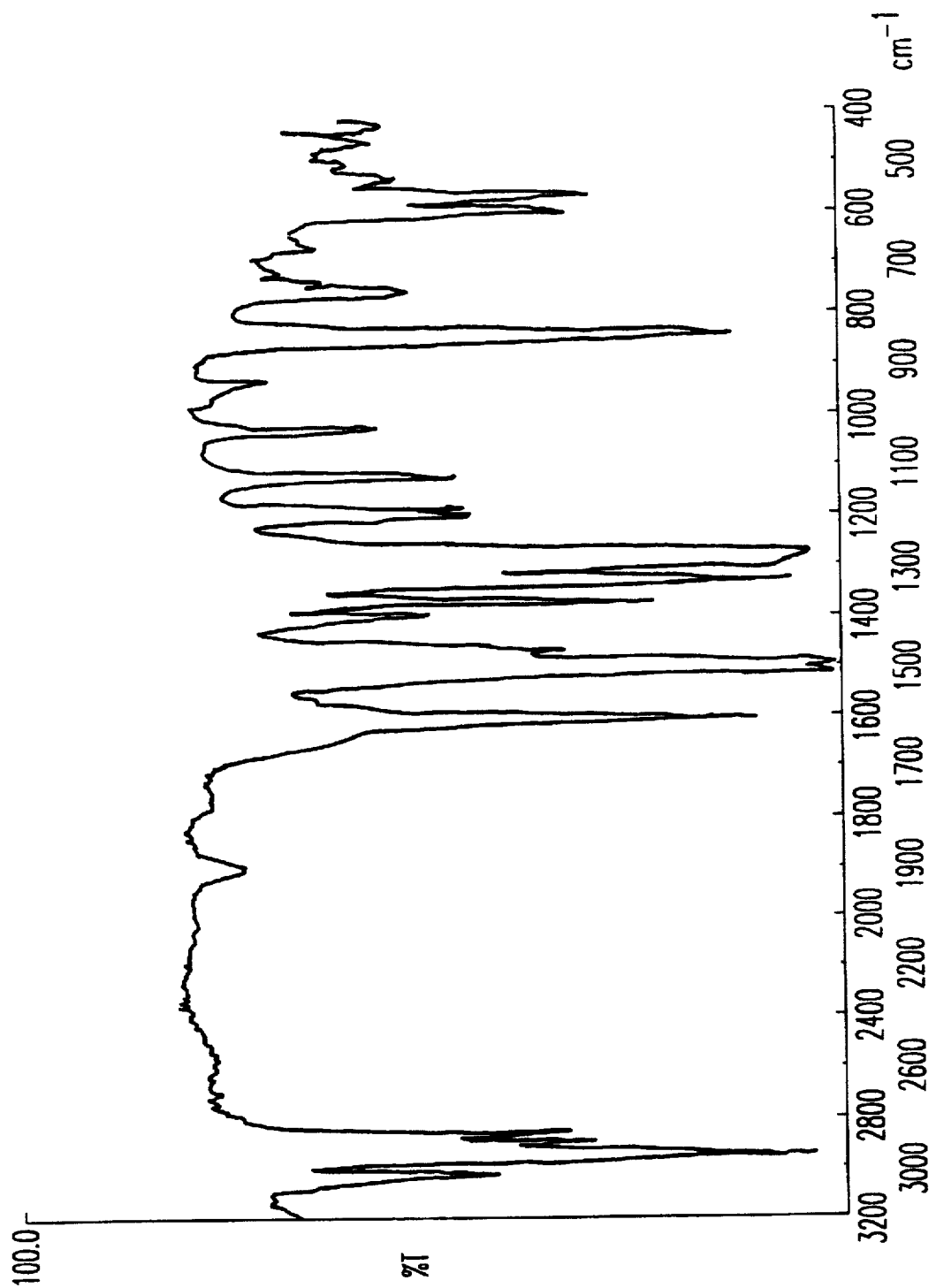
FIG. 4 shows IR spectrum of N,N,N',N'-tetrakis(p-tertiarybutylphenyl)benzidine.
Figure 5:
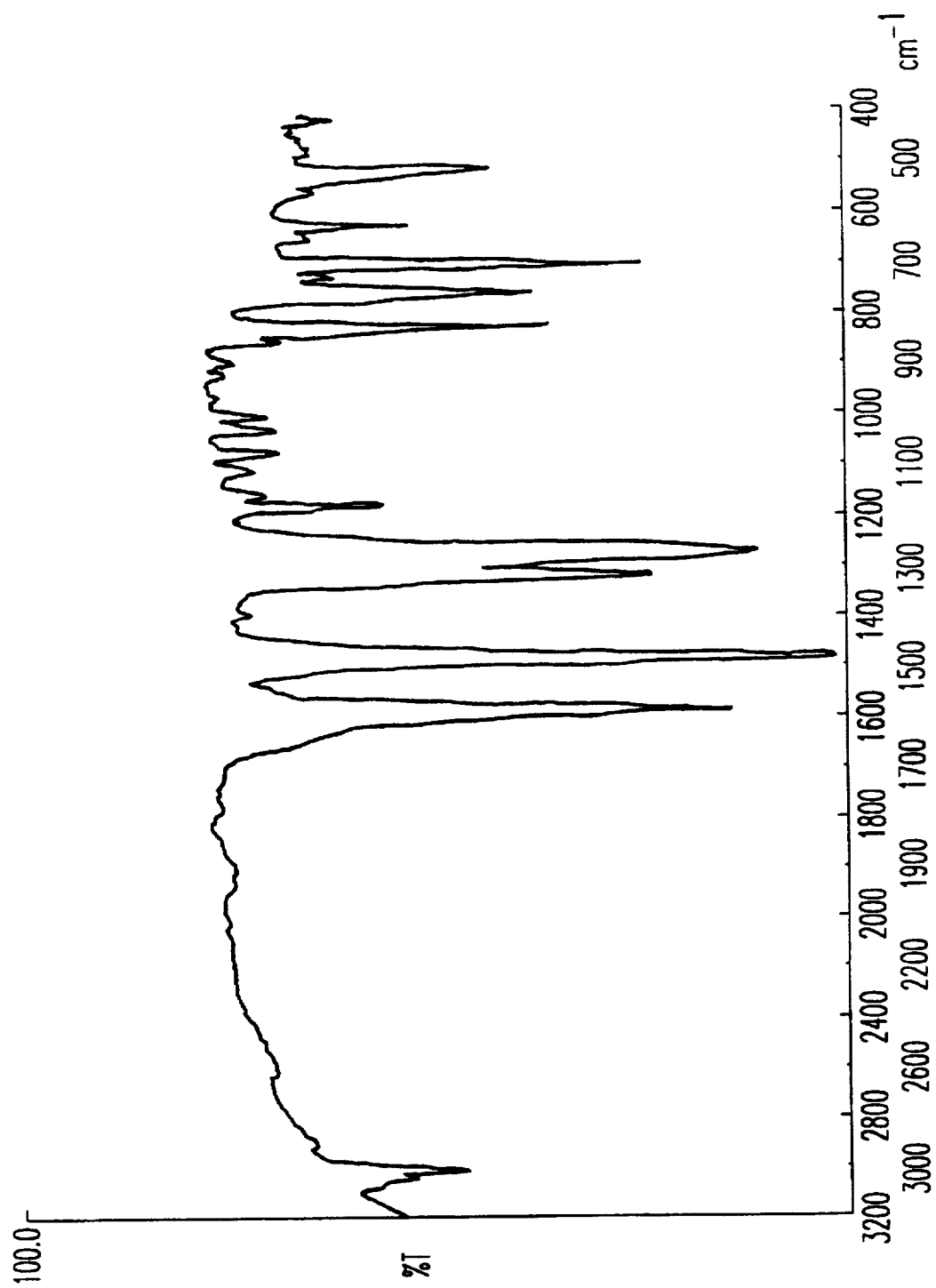
FIG. 5 shows the infrared absorption spectrum of N,N'-bis(4'-diphenylamino-4-biphenylyl)-N,N'-diphenylbenzidine.
Figure 6:
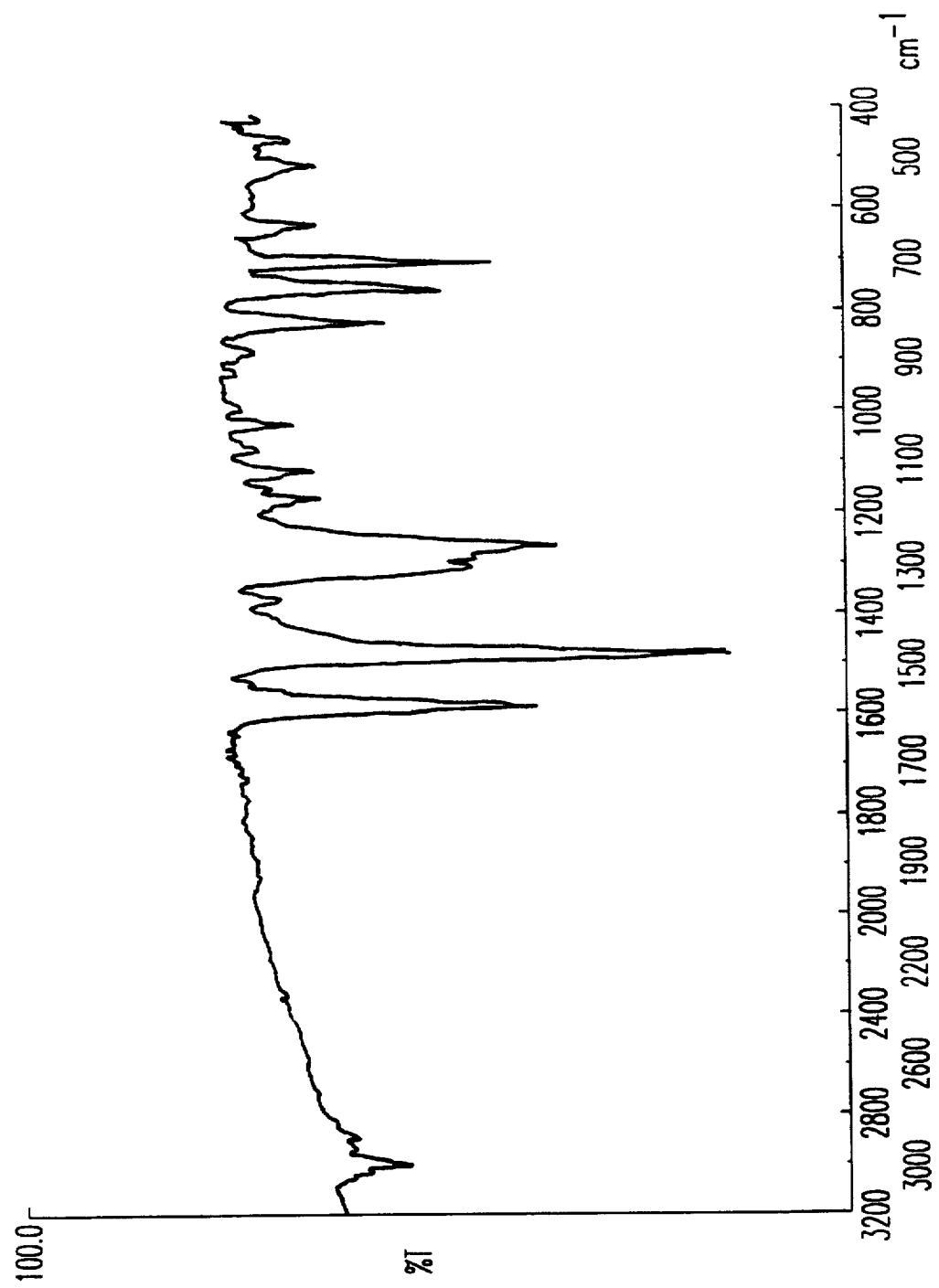
FIG. 6 shows the infrared absorption spectrum of N,N'-bis(3,3'-dimethyl-4'-diphenylamino-4-biphenylyl)-N,N'diphenylbenzidine.
Figure 7:
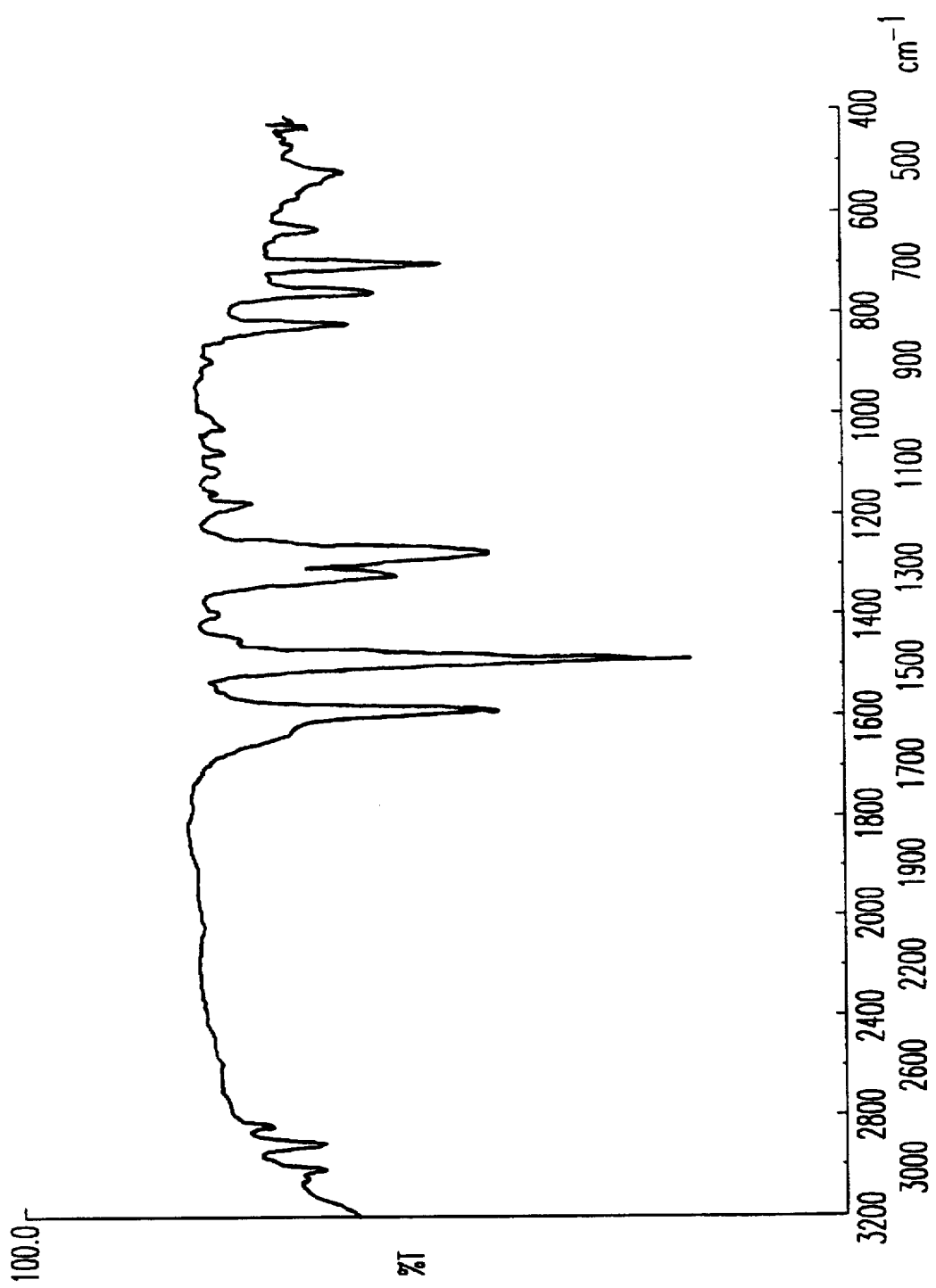
FIG. 7 shows the infrared absorption spectrum of 1,1-bis[p-[N-(4'-diphenylamino-4-biphenylyl)anilino]phenyl]cyclohexane.
Figure 8:
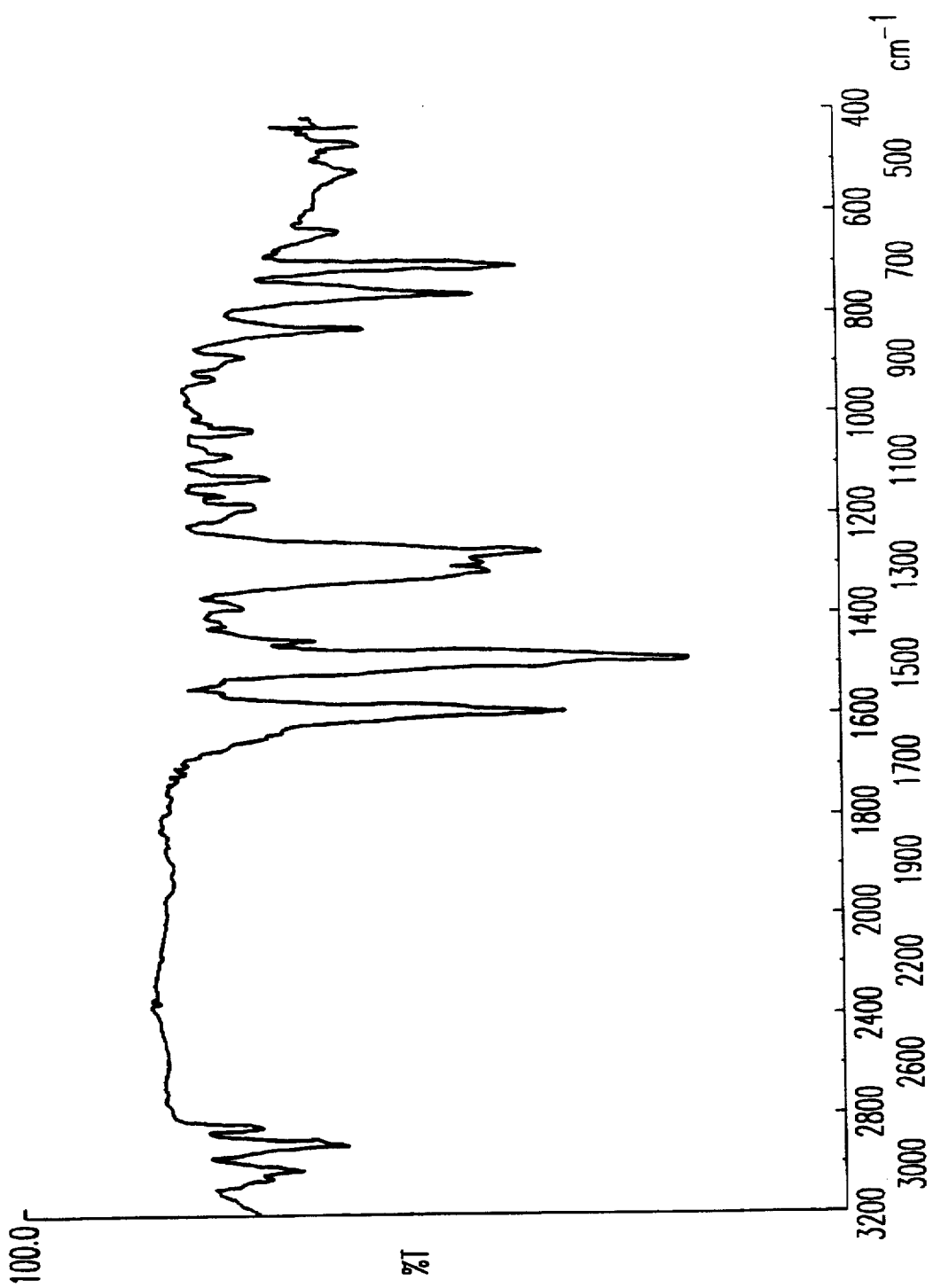
FIG. 8 shows the infrared absorption spectrum of 1,1-bis[p-[N-(4'-diphenylamino-3,3'-dimethyl-4-biphenylyl)anilino]phenyl]cyclohexane.

The present invention will be further described hereinafter.

The amine compound represented by formula (I) is a novel compound. The synthesis of the amine compound can be accomplished by the condensation reaction of the corresponding 4,4'-dihalogenated biphenyl with the corresponding diphenylamine compound or the condensation reaction of the corresponding benzidine compound with the corresponding halogenated aryl. The condensation reaction is known as Ullmann reaction.

For example, an aniline compound represented by the following formula:

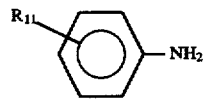

wherein $R_{11}$ is as defined above is N-acetylated to obtain an anilide compound which is then acted upon by a halogenated aryl represented by the following formula:

wherein $R_{12}$ is as defined above; and $X_1$ represents a chlorine, bromine or iodine atom to undergo condensation reaction. The reaction product is then hydrolyzed to obtain a diphenylamine compound represented by the following formula:

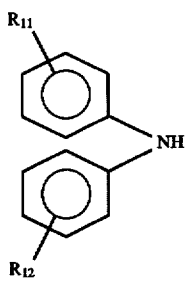

wherein $R_{11}$ and $R_{12}$ are as defined above. The diphenylamine compound thus obtained is then allowed to undergo condensation reaction with 4,4'-dihalogenated biphenyl represented by the following formula:

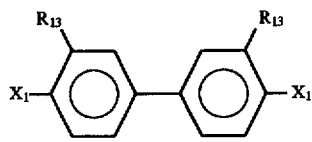

wherein $R_{13}$ and $X_1$ are as defined above, with the proviso that $R_{13}$ and $X_1$ are not chlorine atoms at the same time, to obtain an amine compound according to the present invention.

If an amine compound represented by the following formula:

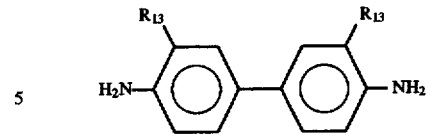

wherein $R_{13}$ is as defined above is used as a starting material, it is acetylated to obtain an N,N'-diacetyl compound which is then acted upon by a halogenated aryl represented by the following formula:

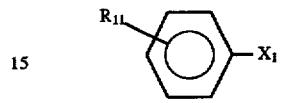

wherein $R_{11}$ and $X_1$ are as defined above. The reaction product is then hydrolyzed. The resulting hydrolyzate is then acted upon by a halogenated aryl represented by the following formula:

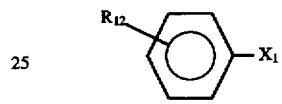

wherein $R_{12}$ and $X_1$ are as defined above to undergo condensation reaction to obtain an amine compound of formula (I) according to the present invention.

Specific examples of the compound of formula of the present invention will be given below.

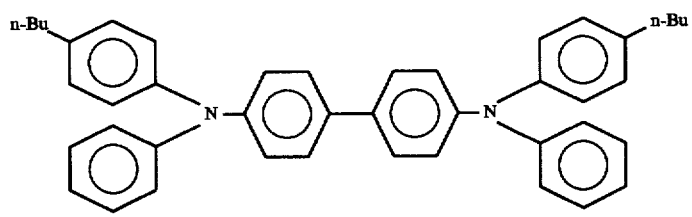

I-1

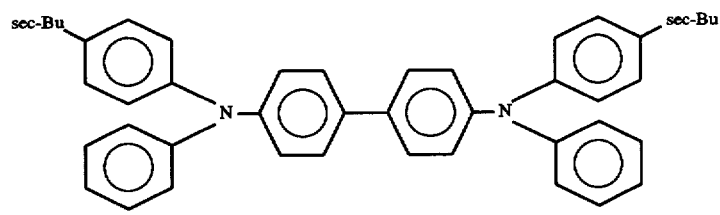

I-2

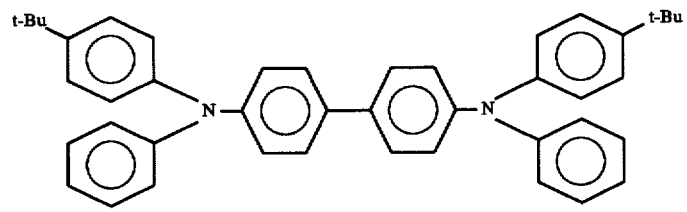

I-3

-continued
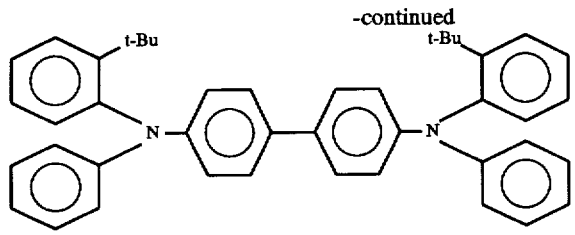 I-4
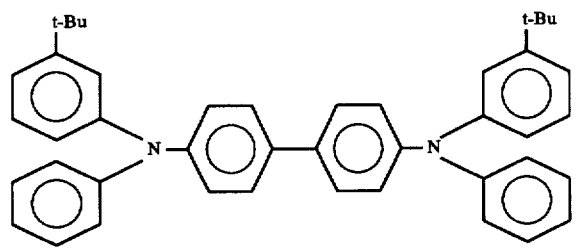 I-5
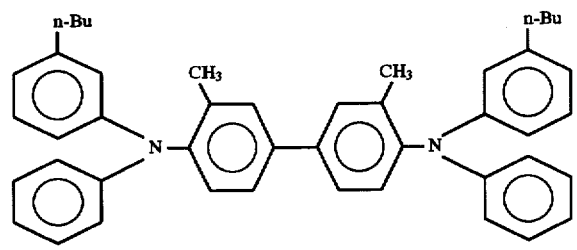 I-6
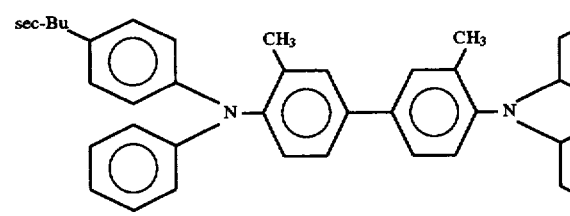 I-7
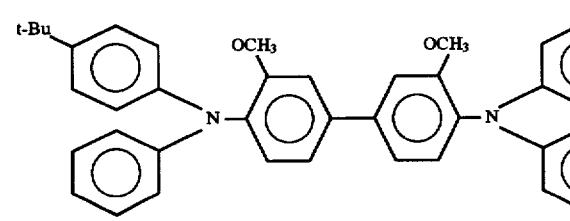 I-8
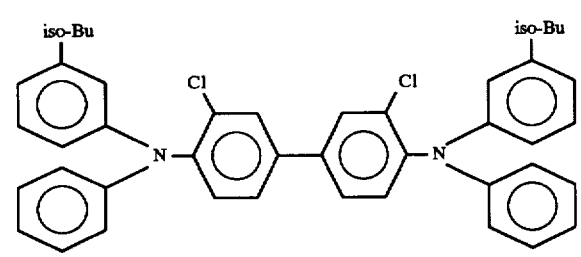 I-9
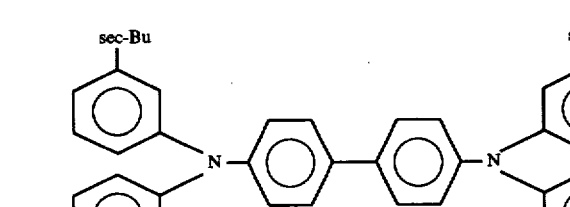 I-10

-continued
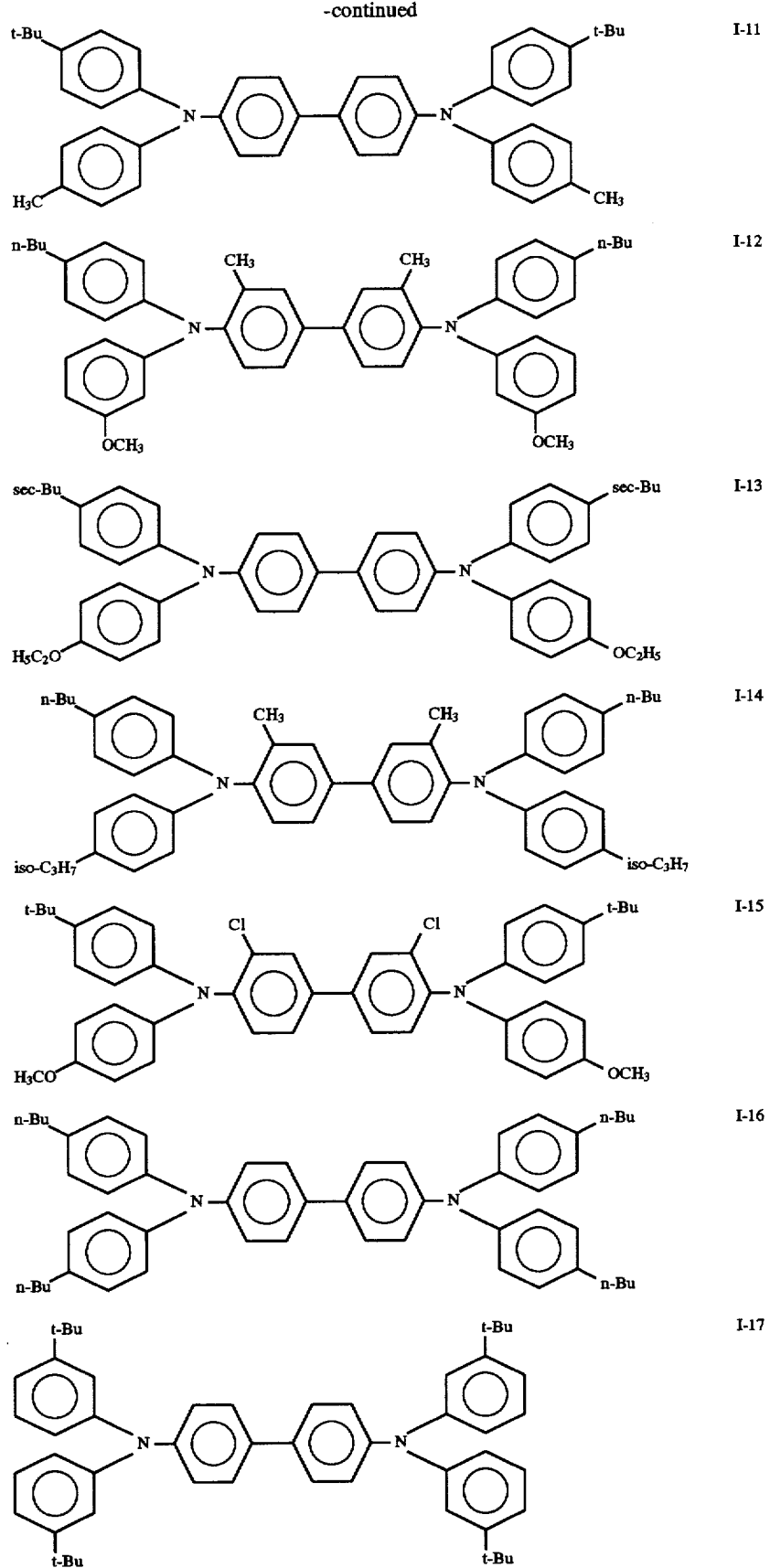

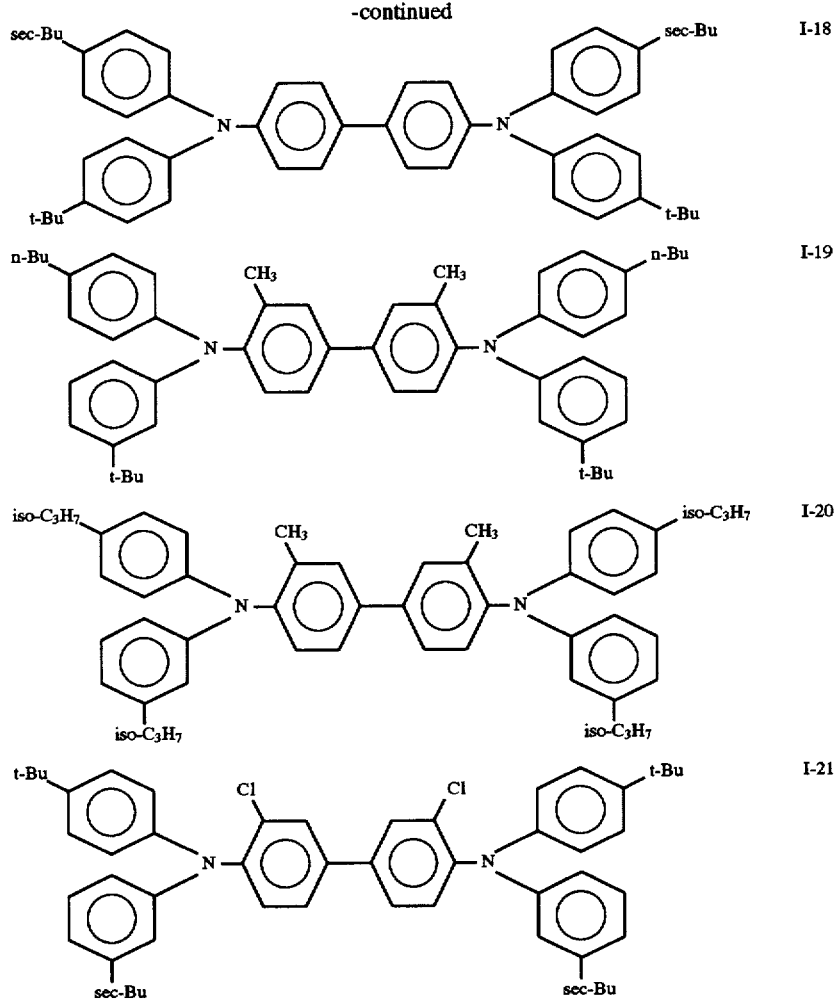

The novel amine compound of formula (I) can easily form and stably maintain a glass state and is the thermally and chemically stable. Thus, the amine compound of the present invention is extremely useful as a hole-transporting material to be incorporated in organic electro-luminescence devices.

The synthesis of the amine compound of formula (I) will be further described in the following synthesis examples.

SYNTHESIS EXAMPLE 1

95.0 g (0.64 mol) of p-normalbutylaniline was dissolved in 170 ml of glacial acetic acid. 81.3 g (0.80 mol) of acetic anhydride was then added dropwise to the solution at a temperature of 30° C. After the completion of dropwise addition, the reaction mixture was then allowed to undergo reaction at a temperature of 40° C. for 1 hour. The reaction solution was then poured into 600 ml of water. The resulting crystal was filtered off, washed with water, and then dried. The crystal thus obtained was then recrystallized from a mixture of 120 ml of toluene and 1,000 ml of n-hexane to obtain 117.5 g (yield: 96.4%) of p-normalbutylacetanilide. The melting point of the crystal was from 105.5° C. to 106.0° C.

20.1 g (0.11 mol) of p-normalbutylacetanilide thus obtained, 24.8 g (0.16 mol) of bromobenzene, 19.4 g (0.14 mol) of anhydrous potassium carbonate, and 0.96 g (0.015 mol) of copper powder were mixed. The reaction mixture was then allowed to undergo reaction at a temperature of 160° C. to 220° C. for 10 hours. The reaction product was then extracted with 100 ml of toluene. The insoluble contents were removed by filtration. The filtrate was then concentrated to dryness. The concentrate was then dissolved in 30 ml of isoamyl alcohol. The material was then hydrolyzed with 3.8 g of water and 13.2 g (0.2 mol) of 85 potassium hydroxide at a temperature of 131° C. The material was then subjected to steam distillation to distill off isoamyl alcohol and excess bromobenzene. The residue was extracted with 140 ml of toluene, washed with water, and then concentrated to dryness. The concentrate was then dried to obtain 21.1 g (yield: 89.4%) of N-phenyl-p-normalbutylaniline.

21.1 g (0.094 mol) of N-phenyl-p-normalbutylaniline, 15.4 g (0.038 mol) of 4,4'-diiodobiphenyl, 15.7 g (0.11 mol) of anhydrous potassium carbonate, and 1.1 g (0.017 mol) of copper powder were mixed. The mixture was then allowed to undergo reaction at a temperature of 170° to 220° C. for 27 hours. The reaction product was then extracted with 140 ml of toluene. The insoluble contents were removed by filtration. The filtrate was then concentrated to obtain an oily material. The crude product thus obtained was then purified by column chromatography (carrier: silica gel; elute: 1/5 mixture of toluene and n-hexane) to obtain 13.4 g (yield: 58.6%) of N,N'-bis(p-normalbutylphenyl)-N,N'-diphenylbenzidine. The melting point of the product was from 135.0° C. to 135.5° C.

SYNTHESIS EXAMPLE 2

70.0 g (0.47 mol) of p-isobutylaniline was dissolved in 126 ml of glacial acetic acid. 59.9 g (0.58 mol) of acetic anhydride was then added dropwise to the solution at a temperature of 30° C. After the completion of dropwise addition, the reaction mixture was then allowed to undergo reaction at a temperature of 40° C. for 1 hour. The reaction solution was then poured into 500 ml of water. The resulting crystal was filtered off, washed with water, and then dried. The crystal thus obtained was then recrystallized from a mixture of 140 ml of toluene and 700 ml of n-hexane to obtain 60.4 g (yield: 67.3%) of p-isobutylacetanilide. The melting point of the crystal was from 124.5° C. to 125.0° C.

17.9 g (0.094 mol) of p-isobutylacetanilide thus obtained, 22.1 g (0.14 mol) of bromobenzene, 16.9 g (0.12 mol) of anhydrous potassium carbonate, and 0.89 g (0.014 mol) of copper powder were mixed. The reaction mixture was then allowed to undergo reaction at a temperature of 168° C. to 217° C. for 14 hours. The reaction product was then extracted with 100 ml of toluene. The insoluble contents were removed by filtration. The filtrate was then concentrated to dryness. The concentrate was then dissolved in 30 ml of isoamyl alcohol. The material was then hydrolyzed with 3.4 g of water and 11.8 g (0.18 mol) of 85 potassium hydroxide at a temperature of 131° C. The material was then subjected to steam distillation to distill off isoamyl alcohol and excess bromobenzene. The residue was extracted with 120 ml of toluene, washed with water, and then concentrated to dryness. The concentrate was then dried to obtain 17.6 g (yield: 86.8%) of N-phenyl-p-isobutylaniline.

17.6 g (0.078 mol) of N-phenyl-p-isobutylaniline, 12.6 g (0.031 mol) of 4,4'-diiodobiphenyl, 12.9 g (0.093 mol) of anhydrous potassium carbonate, and 0.89 g (0.014 mol) of copper powder were mixed. The mixture was then allowed to undergo reaction at a temperature of 190° to 220° C. for 12 hours. The reaction product was then extracted with 70 ml of toluene. The insoluble contents were removed by filtration. The filtrate was then concentrated to obtain an oily material. The crude product thus obtained was then purified by column chromatography (carrier: silica gel; elute: 1/6 mixture of toluene and n-hexane) to obtain 8.5 g (yield: 45.7%) of N,N'-bis(p-isobutylphenyl)-N,N'-diphenylbenzidine. The melting point of the product was from 133.8° C. to 135.3° C.

SYNTHESIS EXAMPLE 3

8.2 g (0.061 mol) of acetanilide, 19.2 g (0.090 mol) of p-tertiarybutylbromobenzene, 9.95 g (0.072 mol) of anhydrous potassium carbonate, and 0.50 g (0.008 mol) of copper powder were mixed. The reaction mixture was then allowed to undergo reaction at a temperature of 190° C. to 203° C. for 23 hours. The reaction product was then extracted with 75 ml of toluene. The insoluble contents were removed by filtration. The filtrate was then concentrated to dryness. The concentrate was then dissolved in 30 ml of isoamyl alcohol. The material was then hydrolyzed with 1.1 g of water and 7.9 g (0.12 mol) of 85% potassium hydroxide at a temperature of 125° C. The material was then subjected to steam distillation to distill off isoamyl alcohol and excess p-tertiarybutylbromobenzene. The residue was extracted with 80 ml of toluene, washed with water, and then concentrated to dryness. The concentrate was then recrystallized from 100 ml of n-hexane to obtain 8.1 g (yield: 58.9%) of N-phenyl-p-tertiarybutylaniline.

8.1 g (0.036 mol) of N-phenyl-p-tertiarybutylaniline, 7.3 g (0.018 mol) of 4,4'-diiodobiphenyl, 7.5 g (0.054 mol) of anhydrous potassium carbonate, and 0.53 g (0.008 mol) of copper powder were mixed. The mixture was then allowed to undergo reaction at a temperature of 210° to 225° C. for 12 hours. The reaction product was then extracted with 70 ml of toluene. The insoluble contents were removed by filtration. The filtrate was then concentrated to obtain an oily material. The crude product thus obtained was then purified by column chromatography (carrier: silica gel; elute: 1/4 mixture of toluene and n-hexane) to obtain 4.5 g (yield: 41.7%) of N,N'-bis(p-tertiarybutylphenyl)-N,N'-diphenylbenzidine. The melting point of the product was from 232.2° C. to 232.6° C.

SYNTHESIS EXAMPLE 4

10.6 g (0.071 mol) of p-tertiarybutylaniline was dissolved in 19 ml of glacial acetic acid. 8.0 g (0.078 mol) of acetic anhydride was then added dropwise to the solution at a temperature of 30° C. After the completion of dropwise addition, the reaction mixture was then allowed to undergo reaction at a temperature of 40° C. for 3 hours. The reaction solution was then poured into 200 ml of water. The resulting crystal was filtered off, washed with water, and then dried to obtain 13.5 g (yield: 99.9%) of p-tertiarybutylacetanilide. The melting point of the crystal was from 172.5° C. to 173.5° C.

13.5 g (0.071 mol) of p-tertiarybutylacetanilide thus obtained, 19.6 g (0.092 mol) of p-teriarybutylbromobenzene, 11.8 g (0.085 mol) of anhydrous potassium carbonate, and 0.58 g (0.009 mol) of copper powder were mixed. The reaction mixture was then allowed to undergo reaction at a temperature of 215° C. to 225° C. for 19 hours. The reaction product was then extracted with 200 ml of toluene. The insoluble contents were removed by filtration. The filtrate was then concentrated. To the concentrate was then added 60 ml of n-hexane to obtain a crystal. The crystal thus obtained was then dissolved in 50 ml of isoamyl alcohol. The material was then hydrolyzed with 1.9 g of water and 6.2 g (0.15 mol) of 93% potassium hydroxide at a temperature of 131° C. The material was then subjected to steam distillation to distill off isoamyl alcohol and excess p-tertiarybutylbromobenzene. The residue was extracted with 120 ml of toluene, washed with water, and then concentrated to dryness. The concentrate was then dried to obtain 15.1 g (yield: 99.4%) of 4,4'-ditertiarybutyl-N,N-diphenylamine.

13.4 g (0.048 mol) of 4,4'-ditertiarybutyl-N,N-diphenylamine, 7.7 g (0.019 mol) of 4,4'-diiodobiphenyl, 7.7 g (0.056 mol) of anhydrous potassium carbonate, 0.53 g (0.008 mol) of copper powder, and 5 ml of nitrobenzene were mixed. The reaction mixture was then allowed to undergo reaction at a temperature of 200° to 215° C. for 4 hours. The reaction product was then extracted with 100 ml of THF. The insoluble contents were removed by filtration. The filtrate was then concentrated to obtain a crystal. The crude crystal thus obtained was then purified by column chromatography (carrier: silica gel; elute: 1/2 mixture of toluene and n-hexane) to obtain 4.3 g (yield: 31.7%) of N,N,N',N'-tetrakis(p-tertiarybutylphenyl)benzidine. The melting point of the product was from 402.0° C. to 403.0° C.

FIGS. 1 to 4 show the infrared absorption spectra of the compounds obtained in Synthesis Examples 1 to 4, respectively. The infrared absorption spectra were determined by KBr tablet process by means of IR-700 available from Nihon Bunko Kogyo K.K.

The results of elementary analysis of the compounds obtained in Synthesis Examples 1 to 4 are set forth in Table

TABLE 1

| Synthesis Example No. | Elementary Analysis (Measured/calculated) | | |
|---|---|---|---|
| | C (%) | H (%) | N (%) |
| 1 | 87.93/87.96 | 7.45/7.38 | 4.57/4.66 |
| 2 | 87.77/87.96 | 7.43/7.38 | 4.51/4.66 |
| 3 | 87.81/87.96 | 7.42/7.38 | 4.67/4.66 |
| 4 | 87.53/87.59 | 8.55/8.48 | 3.76/3.93 |

The amine compound represented by formula (II) is a novel compound. The synthesis of the amine compound can be accomplished by hydrolyzing the product of the condensation reaction of the corresponding triphenylbenzidine compound with the corresponding dihalogenated compound or the condensation reaction of the corresponding N,N'-diacetylated diamino compound with the corresponding 4'-halogenated biphenylacetanilide compound, and then subjecting the hydrolyzate to condensation reaction with the corresponding halogenated aryl. The condensation reaction is known as Ullmann reaction.

For example, a 4,4'-dihalogenated biphenyl compound represented by the following formula:

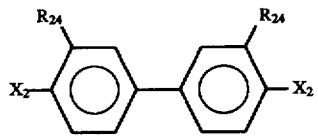

wherein $R_{24}$ is as defined above; and $X_2$ represents a chlorine atom, bromine atom or iodine atom, with the proviso that $R_{24}$ and $X_2$ are not chlorine atoms at the same time, is condensed with an anilide compound represented by the following formula:

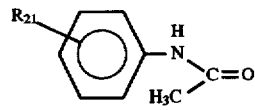

wherein $R_{21}$ is as defined above in the same molar quantity, to obtain a 4'-halogenated biphenylacetanilide compound represented by the following formula:

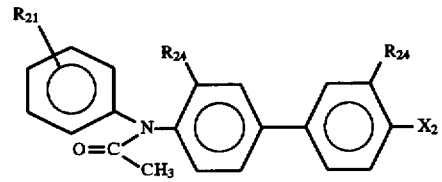

wherein $R_{21}$, $R_{24}$ and $X_2$ are as defined above, with the proviso that $R_{24}$ and $X_2$ are not chlorine atoms at the same time. The 4'-halogenated biphenylacetanilide compound thus obtained is then condensed with a diphenylamine compound represented by the following formula:

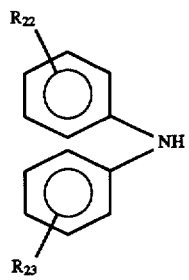

wherein $R_{22}$ and $R_{23}$ are as defined above. The condensation product is then hydrolyzed to obtain a triphenylbenzidine compound represented by the following formula:

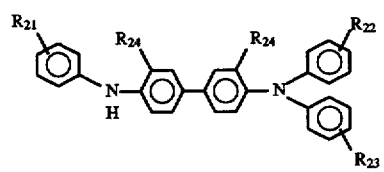

wherein $R_{21}$, $R_{22}$, $R_{23}$ and $R_{24}$ are as defined above. Two equivalents of the triphenylbenzidine compound are acted upon by one equivalent of a dihalogenated compound represented by the following formula:

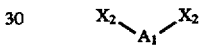

wherein $X_2$ and $A_1$ are as defined above, to obtain an amine compound of formula (II) of the present invention.

If a diamino compound represented by the following formula:

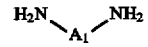

wherein $A_1$ is as defined above is used as a starting material, the amino group is acetylated to obtain a diacetylated compound which is then condensed with a halogenated aryl represented by the following formula:

wherein $R_{21}$ and $X_2$ are as defined above. The reaction product is then hydrolyzed to obtain a diaryldiamino compound represented by the following formula:

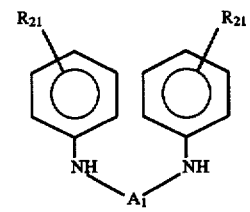

wherein $R_{21}$ and $A_1$ are as defined above. The dihalogenated biphenyl compound is then condensed with a 4'-halogenated biphenylacetanilide compound represented by the following formula:

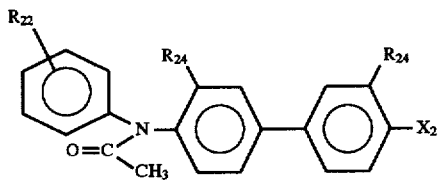

wherein $R_{22}$, $R_{24}$ and $X_2$ are as defined above, with the proviso that $R_{24}$ and $X_2$ are not chlorine atoms at the same time, synthesized from a dihalogenated biphenyl compound and an anilide compound in the same manner as above. The condensate is then hydrolyzed to obtain a tetramine compound represented by the following formula:

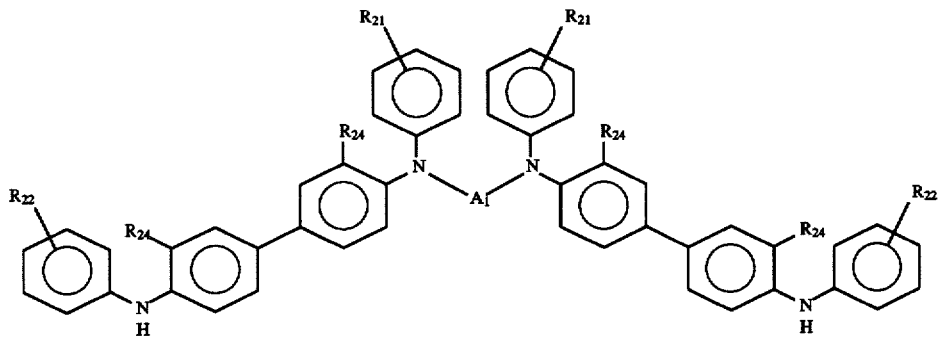

wherein $R_{21}$, $R_{22}$, $R_{24}$ and $A_1$ are as defined above. The tetramine compound thus obtained is then condensed with a halogenated aryl represented by the following formula:

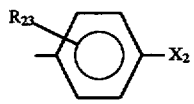

wherein $R_{23}$ and $X_2$ are as defined above to obtain an amine compound of formula (II). Among the foregoing condensation reactions, the condensation reaction of 4,4'-dihalogenated biphenyl with an acetanilide compound may be effected by using benzanilide instead of the acetanilide compound.

The foregoing condensation reaction of various halogenated aryls with various amine compounds is effected in the presence or absence of solvent. As such a solvent there may be used nitrobenzene or dichlorobenzene. As a basic compound to be used a deacidification agent there may be used potassium carbonate, sodium carbonate, sodium hydrogencarbonate, potassium hydroxide, sodium hydroxide or the like. The condensation reaction may be also effected in the presence of a catalyst such as copper powder and halogenated copper. The reaction temperature is normally in the range of 160° to 230° C.

The novel amine compound of formula (II) can easily form and stably maintain a glass state and is thermally and chemically stable. Thus, the amine compound of formula (II) is extremely useful as a hole-transporting material to be incorporated in organic electro-luminescence devices. Specific examples of the compound of formula (II) will be given below.

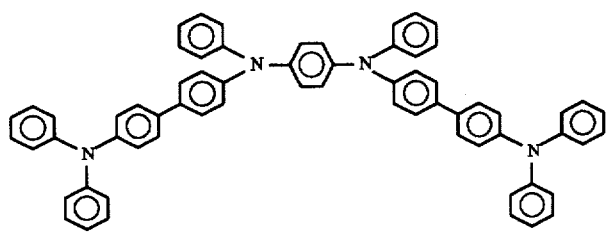
II-1
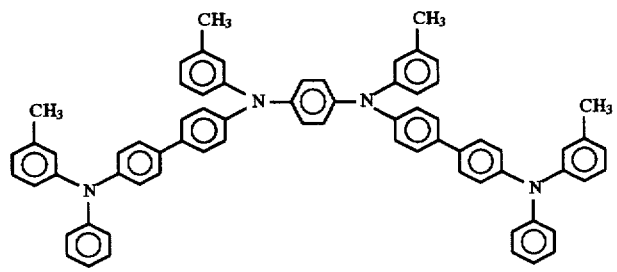
II-2
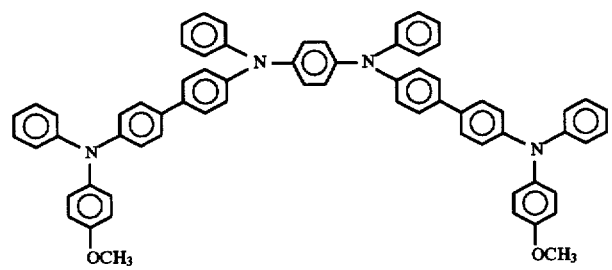
II-3
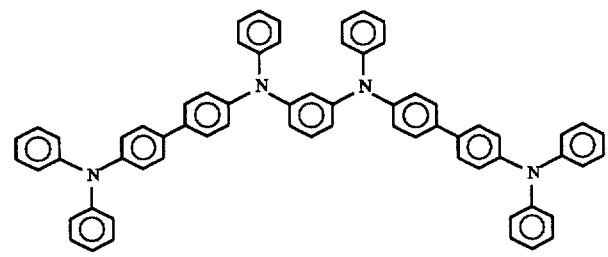
II-4
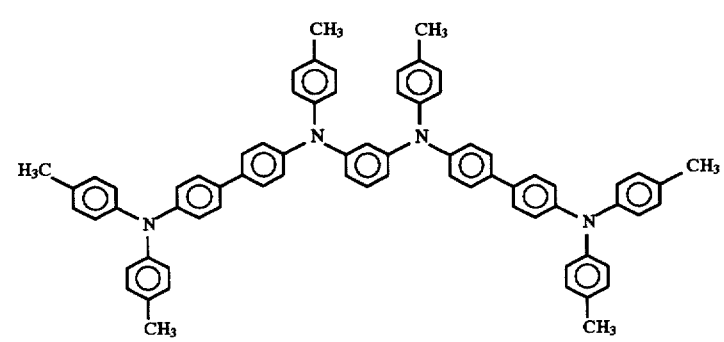
II-5
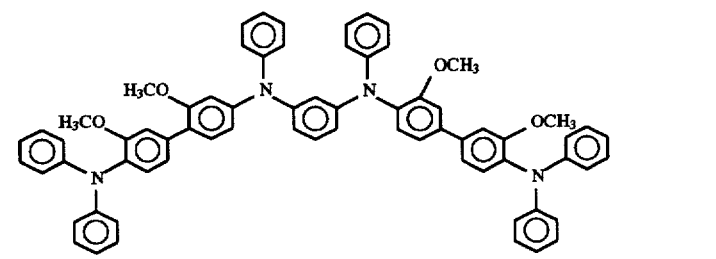
II-6

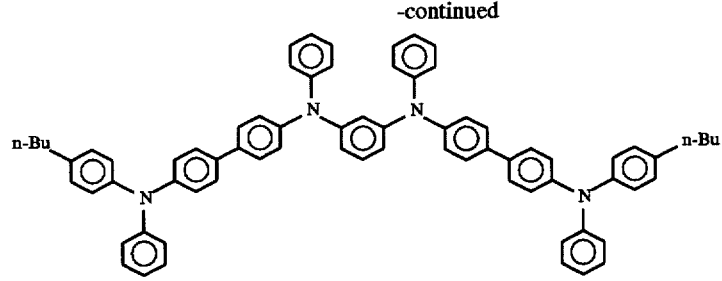
II-7
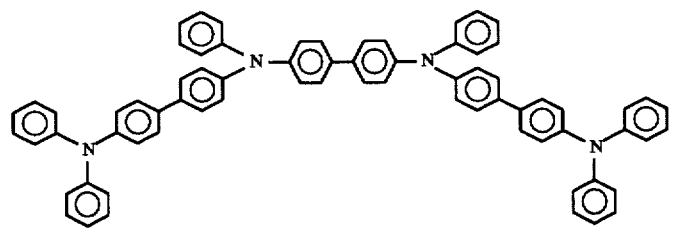
II-8
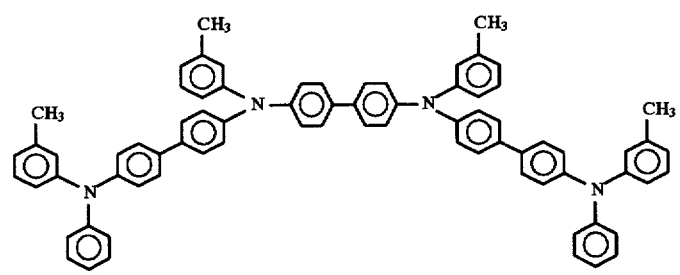
II-9
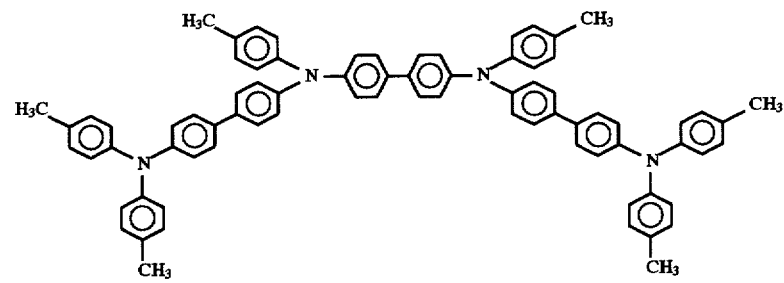
II-10
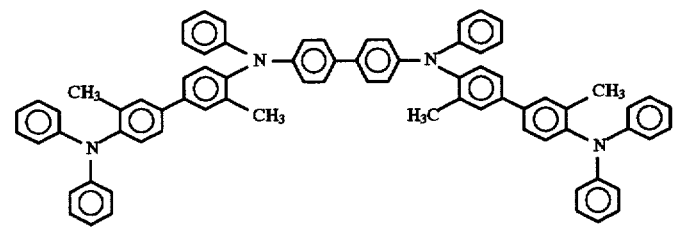
II-11
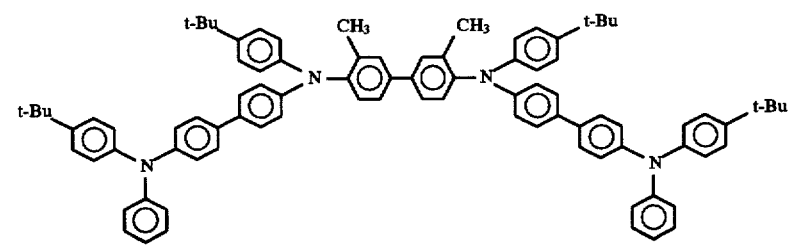
II-12

-continued
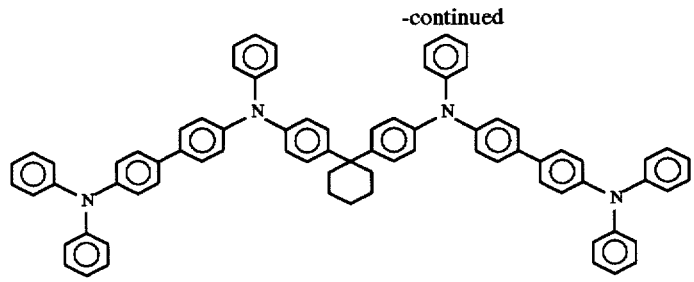
II-13
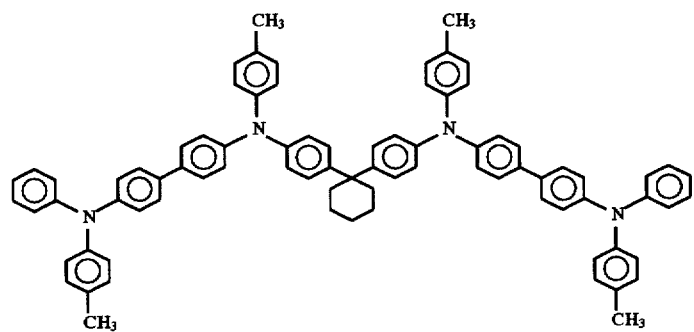
II-14
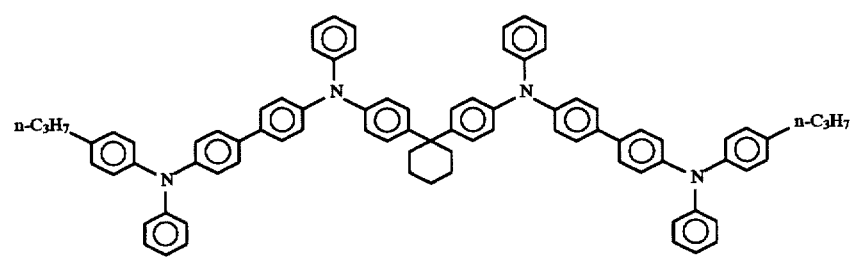
II-15
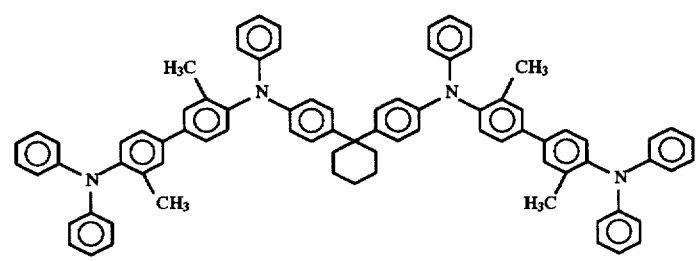
II-16
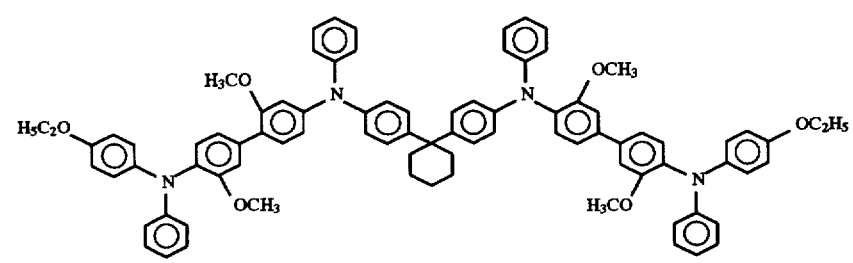
II-17
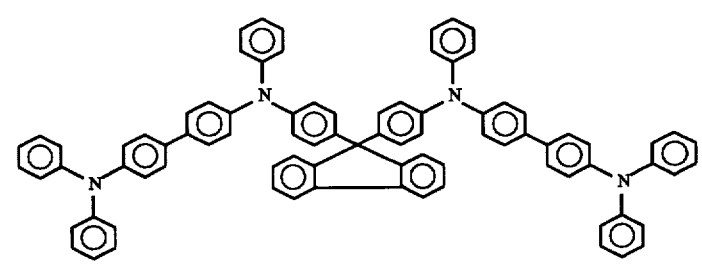
II-18

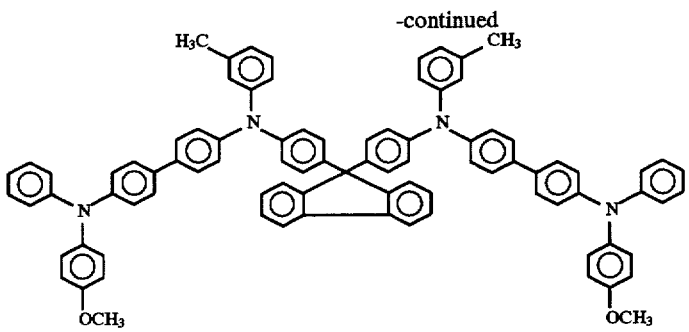

II-19

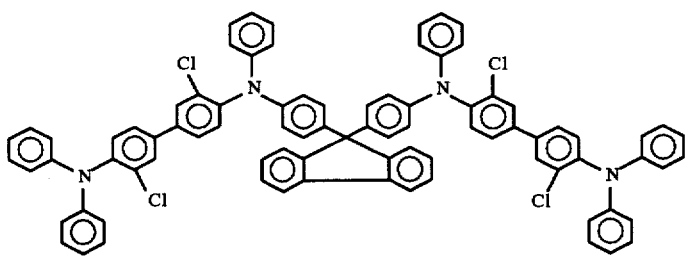

I-20

The synthesis of the amine compound of formula (II) will be further described in the following synthesis examples.

SYNTHESIS EXAMPLE 5

20.3 g (0.15 mol) of acetanilide, 73.1 g (0.18 mol) of 4,4'-diiodobiphenyl, 22.1 g (0.16 mol) of anhydrous potassium carbonate, 2.16 g (0.034 mol) of copper powder, and 35 ml of nitrobenzene were mixed. The reaction mixture was then allowed to undergo reaction at a temperature of 190° C. to 205° C. for 10 hours. The reaction product was then extracted with 200 ml of toluene. The insoluble contents were removed by filtration. The filtrate was then concentrated to dryness. The concentrate was then purified by column chromatography (carrier: silica gel; elute: 6/1 mixture of toluene and ethyl acetate) to obtain 40.2 g (yield: 64.8%) of N-(4'-iodo-4-biphenylyl)acetanilide. The melting point of the product was from 135.0° C. to 136.0° C.

Subsequently, 13.2 g (0.032 mol) of N-(4'-iodo-4-biphenyl)acetanilide thus obtained, 6.60 g (0.039 mol) of diphenylamine, 5.53 g (0.040 mol) of anhydrous potassium carbonate, 0.45 g (0.007 mol) of copper powder, and 10 ml of nitrobenzene were mixed. The reaction mixture was then allowed to undergo reaction at a temperature of 200° to 212° C. for 15 hours. The reaction product was then extracted with 100 ml of toluene. The insoluble contents were then removed by filtration. The filtrate was then concentrated to obtain an oily matter. The oily matter thus obtained was then dissolved in 60 ml of isoamyl alcohol. The material was then hydrolyzed with 1 ml of water and 2.64 g (0.040 mol) of 85% potassium hydroxide at a temperature of 130° C. The reaction solution was then subjected to steam distillation to distill off isoamyl alcohol. The residue was extracted with 250 ml of toluene, washed with water, and then concentrated to dryness. The concentrate was then purified by column chromatography (carrier: silica gel; elute: 1/2 mixture of toluene and n-hexane) to obtain 10.5 g (yield: 72.2%) of N,N,N'-triphenylbenzidine. The melting point of the product was from 167.5° C. to 168.5° C.

8.66 g (0.021 mol) of N,N,N'-triphenylbenzidine thus obtained, 4.06 g (0.01 mol) of 4,4'-diiodobiphenyl, 2.90 g (0.021 mol) of anhydrous potassium carbonate, 0.32 g (0.005 mol) of copper powder, and 10 ml of nitrobenzene were mixed. The reaction mixture was then allowed to undergo reaction at a temperature of 195° C. to 210° C. for 20 hours. The reaction product was then extracted with 140 ml of toluene. The insoluble contents were removed by filtration. The filtrate was then concentrated. To the concentrate was then added 120 ml of n-hexane to recover a crude crystal. The crude crystal thus recovered was then purified by column chromatography (carrier: silica gel; elute: 1/2 mixture of toluene and n-hexane) to obtain 4.73 g (yield: 48.5%) of N,N'-bis(4'-diphenylamino-4-biphenylyl)-N,N'-diphenylbenzidine. The melting point of the product was from 242.5° C. to 243.5° C.

SYNTHESIS EXAMPLE 6

16.2 g (0.12 mol) of acetanilide, 56.4 g (0.13 mol) of 3,3'-dimethyl-4,4'-diiodobiphenyl, 18.0 g (0.13 mol) of anhydrous potassium carbonate, 1.71 g (0.027 mol) of copper powder, and 30 ml of nitrobenzene were mixed. The reaction mixture was then allowed to undergo reaction at a temperature of 192° C. to 203° C. for 13 hours. The reaction product was then extracted with 160 ml of toluene. The insoluble contents were removed by filtration. The filtrate was then concentrated to dryness. The concentrate was then purified by column chromatography (carrier: silica gel; elute: 7/1 mixture of toluene and ethyl acetate) to obtain 36.7 g (yield: 69.3%) of N-(3,3'-dimethyl-4'-iodo-4-biphenylyl)acetanilide. Subsequently, 13.2 g (0.030 mol) of N-(3,3'-dimethyl-4'-iodo-4-biphenylyl)acetanilide thus obtained, 6.09 g (0.036 mol) of diphenylamine, 5.11 g (0.037 mol) of anhydrous potassium carbonate, 0.44 g (0.007 mol) of copper powder, and 10 ml of nitrobenzene were mixed. The reaction mixture was then allowed to undergo reaction at a temperature of 198° to 211° C. for 13 hours. The reaction product was then extracted with 100 ml of toluene. The insoluble contents were then removed by filtration. The filtrate was then concentrated to obtain an oily matter. The oily matter thus obtained was then dissolved in 50 ml of isoamyl alcohol. The material was then hydrolyzed with 1 ml of water and 2.38 g (0.036 mol) of 85% potassium hydroxide at a temperature of 130° C. The reaction solution was then subjected to steam distillation to distill off isoamyl alcohol. The residue was extracted with 200 ml of toluene, washed with water, and then concentrated to dryness. The concentrate was then purified by column chromatography (carrier: silica gel; elute: 1/3 mixture of toluene and n-hexane) to obtain 9.27 g (yield: 70.1%) of 3,3'-dimethyl-N,N,N'-triphenylbenzidine. The melting point of the product was from 104.0° C. to 105.0° C.

8.37 g (0.019 mol) of 3,3'-dimethyl-N,N,N'-triphenylbenzidine thus obtained, 3.65 g (0.009 mol) of 4,4'-diiodobiphenyl, 2.63 g (0.019 mol) of anhydrous potassium carbonate, 0.25 g (0.004 mol) of copper powder, and 7 ml of nitrobenzene were mixed. The reaction mixture was then allowed to undergo reaction at a temperature of 197° C. to 212° C. for 36 hours. The reaction product was then extracted with 130 ml of toluene. The insoluble contents were removed by filtration. The filtrate was then concentrated. To the concentrate was then added 110 ml of n-hexane to recover a crude crystal. The crude crystal thus recovered was then purified by column chromatography (carrier: silica gel; elute: 1/2 mixture of toluene and n-hexane) to obtain 4.84 g (yield: 52.1%) of N,N'-bis(3,3'-dimethyl-4'-diphenylamino-4-biphenylyl)-N,N'-diphenylbenzidine. The melting point of the product was indefinite.

SYNTHESIS EXAMPLE 7

16.0 g (0.06 mol) of 1,1-bis(4-aminophenyl)cyclohexane was dissolved in 50 ml of glacial acetic acid. 13.3 g (0.13 mol) of acetic anhydride was then added dropwise to the solution at a temperature of 40° C. After the completion of dropwise addition, the reaction mixture was then allowed to undergo reaction at a temperature of 60° C. for 2 hours. The reaction solution was then poured into 300 ml of ice water. The resulting crystal was filtered off, washed with water, and then dried. The crystal thus obtained was then recrystallized from a mixture of 40 ml of ethyl acetate and 150 ml of methanol to obtain 13.5 g (yield: 64.3%) of 1,1-bis(4-acetamidephenyl)cyclohexane. The melting point of the product was from 270.0° C. to 271.0° C.

10.5 g (0.03 mol) of 1,1-bis(4-acetamidephenyl)cyclohexane thus obtained, 10.4 g (0.066 mol) of bromobenzene, 8.71 g (0.063 mol) of anhydrous potassium carbonate, and 0.95 g (0.015 mol) of copper powder were mixed. The reaction mixture was then allowed to undergo reaction at a temperature of 170° C. to 200 ° C. for 16 hours. The reaction product was then extracted with 150 ml of toluene. The insoluble contents were removed by filtration. The filtrate was then concentrated to obtain an oily matter. The oily matter thus obtained was then dissolved in 50 ml of isoamyl alcohol. The material was then hydrolyzed with 1 ml of water and 4.16 g (0.063 mol) of 85% potassium hydroxide at a temperature of 130° C. The material was then subjected to steam distillation to distill off isoamyl alcohol. The residue was extracted with 200 ml of toluene, washed with water, and then concentrated to dryness. The concentrate was then purified by column chromatography (carrier: silica gel; elute: 3/2 mixture of toluene and n-hexane) to obtain 9.31 g (yield: 74.1%) of 1,1-bis(4-anilinophenyl)cyclohexane.

Subsequently, in the same manner as in Synthesis Example 5, 18.4 g (0.042 mol) of N-(4'-iodo-4-biphenylyl)acetanilide obtained by the condensation reaction of acetanilide with 4,4'-diiodobiphenyl, 8.37 g (0.02 mol) of 1,1-bis(4-anilinophenyl)cyclohexane thus obtained, 5.80 g (0.042 mol) of anhydrous potassium carbonate, 0.57 g (0.009 mol) of copper powder, and 20 ml of nitrobenzene were mixed. The reaction mixture was then allowed to undergo reaction at a temperature of 198° to 215° C. for 21 hours. The reaction product was then extracted with 150 ml of toluene. The insoluble contents were then removed by filtration. The filtrate was then concentrated to obtain an oily matter. The oily matter thus obtained was then dissolved in 80 ml of isoamyl alcohol. The material was then hydrolyzed with 1 ml of water and 2.77 g (0.042 mol) of 85% potassium hydroxide at a temperature of 130° C. The reaction solution was then subjected to steam distillation to distill off isoamyl alcohol. The residue was extracted with 180 ml of toluene, washed with water, and then concentrated to dryness. The concentrate was then purified by column chromatography (carrier: silica gel; elute: 1/1 mixture of toluene and n-hexane) to obtain 10.4 g (yield: 57.3%) of 1,1-bis[p-[N-(4'-anilino-4-biphenylyl)anilino]phenyl]cyclohexane.

9.05 g (0.01 mol) of 1,1-bis[p-[N-(4'-anilino-4-biphenylyl)anilino]phenyl]cyclohexane thus obtained, 4.49 g (0.022 mol) of iodobenzene, 2.90 g (0.021 mol) of anhydrous potassium carbonate, 0.32 g (0.005 mol) of copper powder, and 15 ml of nitrobenzene were mixed. The reaction mixture was then allowed to undergo reaction at a temperature of 198° C. to 213° C. for 19 hours. The reaction product was then extracted with 150 ml of toluene. The insoluble contents were removed by filtration. The filtrate was then concentrated. To the concentrate was then added 110 ml of n-hexane to recover a crude crystal. The crude crystal thus recovered was then purified by column chromatography (carrier: silica gel; elute: 2/3 mixture of toluene and n-hexane) to obtain 5.17 g (yield: 48.9%) of 1,1-bis[p-[N-(4'-diphenylamino-4-biphenylyl)anilino]phenyl]cyclohexane. The melting point of the product was indefinite.

SYNTHESIS EXAMPLE 8

10.5 g (0.025 mol) of 1,1-bis(4-anilinophenyl)cyclohexane obtained in the same manner as in Synthesis Example 7, 22.9 g (0.052 mol) of N-(3,3'-dimethyl-4'-iodo-4-biphenylyl)acetanilide obtained in the same manner as in Synthesis Example 6, 7.19 g (0.052 mol) of anhydrous potassium carbonate, 0.76 g (0.012 mol) of copper powder, and 20 ml of nitrobenzene were mixed. The reaction mixture was then allowed to undergo reaction at a temperature of 200° to 208° C. for 18 hours. The reaction product was then extracted with 180 ml of toluene. The insoluble contents were then removed by filtration. The filtrate was then concentrated to obtain an oily matter. The oily matter thus obtained was then dissolved in 80 ml of isoamyl alcohol. The solution was then hydrolyzed with 1 ml of water and 2.77 g (0.042 mol) of 85% potassium hydroxide at a temperature of 130° C. The solution was then subjected to steam distillation to distill off isoamyl alcohol. The residue was extracted with 180 ml of toluene, washed with water, and then concentrated to dryness. The concentrate was then purified by column chromatography (carrier: silica gel; elute: 1/1 mixture of toluene and n-hexane) to obtain 13.3 g (yield: 55.1%) of 1,1-bis[p-[N-(4'-anilino-3,3'-dimethyl-4-biphenylyl)anilino]phenyl]cyclohexane.

11.5 g (0.012 mol) of 1,1-bis[p-[N-(4'-anilino-3,3'-dimethyl-4-biphenylyl)anilino]phenyl]cyclohexane thus obtained, 5.30 g (0.026 mol) of iodobenzene, 3.46 g (0.025 mol) of anhydrous potassium carbonate, 0.38 g (0.006 mol) of copper powder, and 15 ml of nitrobenzene were mixed. The reaction mixture was then allowed to undergo reaction at a temperature of 198° C. to 213° C. for 19 hours. The reaction product was then extracted with 150 ml of toluene. The insoluble contents were removed by filtration. The filtrate was then concentrated. To the concentrate was then added 120 ml of n-hexane to recover a crude crystal. The crude crystal thus recovered was then purified by column chromatography (carrier: silica gel; elute: 1/3 mixture of toluene and n-hexane) to obtain 5.57 g (yield: 41.7%) of 1,1-bis[p-[N-(4'-diphenylamino-3,3'-dimethyl-4-biphenylyl)anilino]phenyl]cyclohexane. The melting point of the product was indefinite.

FIGS. 5 to 8 show the infrared absorption spectra of the compounds obtained in Synthesis Examples 5 to 8, respectively. The infrared absorption spectra were determined by KBr tablet process by means of IR-700 available from Nihon Bunko Kogyo K.K.

Table 2 shows the results of elementary analysis of the compounds obtained in Synthesis Examples 5 to 8.

time, is condensed with an anilide compound represented by the following formula:

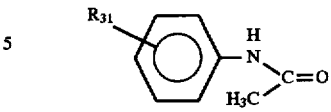

wherein $R_{31}$ is as defined above in the same molar quantity, to obtain a 4'-halogenated biphenylacetanilide compound represented by the following formula:

TABLE 2

| Synthesis Example No. | $R_{21}$ | $R_{22}$ | $R_{23}$ | $R_{24}$ | $A_1$ | C (%) | H (%) | N (%) |
|---|---|---|---|---|---|---|---|---|
| 5 | H | H | H | H | biphenyl | 88.75/88.67 | 5.70/5.58 | 5.68/5.75 |
| 6 | H | H | H | $CH_3$ | biphenyl | 88.50/88.51 | 6.18/6.06 | 5.41/5.43 |
| 7 | H | H | H | H | biphenyl-cyclohexane | 88.69/88.60 | 6.16/6.10 | 5.21/5.30 |
| 8 | H | H | H | $CH_3$ | biphenyl-cyclohexane | 88.37/88.45 | 6.55/6.52 | 5.19/5.03 |

The amine compound represented by formula (III) is a novel compound. The synthesis of the amine compound can be accomplished by hydrolyzing the product of the condensation reaction of the corresponding triphenylbenzidine compound with the corresponding dihalogenated compound or the condensation reaction of the corresponding N,N'-diacetylated diamino compound with the corresponding 4'-halogenated biphenylacetanilide compound, and then subjecting the hydrolyzate to condensation reaction with the corresponding halogenated aryl. The condensation reaction is known as Ullmann reaction.

For example, a 4,4'-dihalogenated biphenyl compound represented by the following formula:

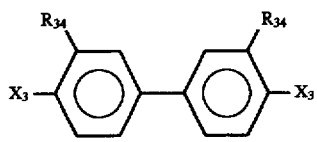

wherein $R_{34}$ is as defined above; and $X_3$ represents a chlorine atom, bromine atom or iodine atom, with the proviso that $R_{34}$ and $X_3$ are not chlorine atoms at the same

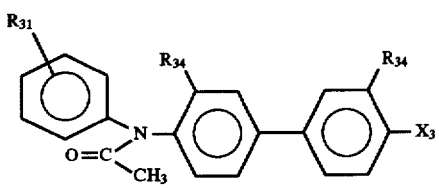

wherein $R_{31}$, $R_{34}$ and $X_3$ are as defined above, with the proviso that $R_{34}$ and $X_3$ are not chlorine atoms at the same time. The 4'-halogenated biphenylacetanilide compound thus obtained is then condensed with a diphenylamine compound represented by the following formula:

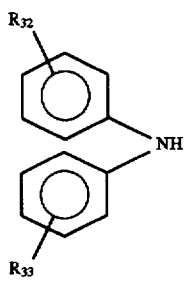

wherein $R_{32}$ and $R_{33}$ are as defined above. The condensation product is then hydrolyzed to obtain a triphenylbenzidine compound represented by the following formula:

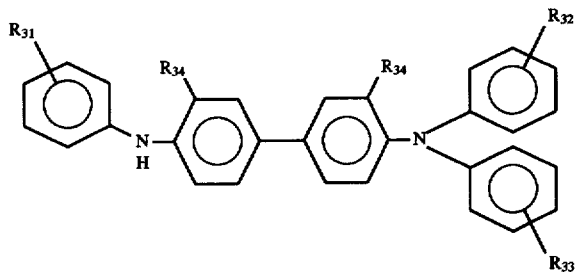

wherein $R_{31}$, $R_{32}$, $R_{33}$ and $R_{34}$ are as defined above. Two equivalents of the triphenylbenzidine compound are acted upon by one equivalent of a dihalogenated compound represented by the following formula:

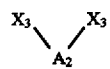

wherein $X_3$ and $A_2$ are as defined above, to obtain an amine compound of formula (III) of the present invention.

If a diamino compound represented by the following formula:

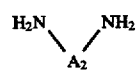

wherein $A_2$ is as defined above is used as a starting material, the amino group is acetylated to obtain a diacetylated compound which is then condensed with a halogenated aryl represented by the following formula:

wherein $R_{31}$ and $X_3$ are as defined above. The reaction product is then hydrolyzed to obtain a diaryldiamino compound represented by the following formula:

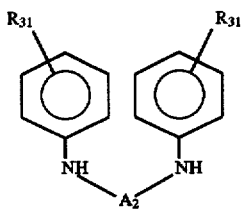

wherein $R_{31}$ and $A_2$ are as defined above. The dihalogenated biphenyl compound is then condensed with a 4'-halogenated biphenylacetanilide compound represented by the following formula:

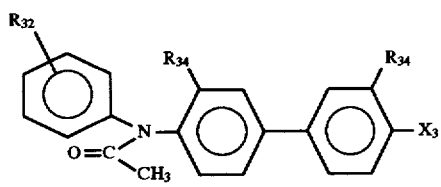

wherein $R_{32}$, $R_{34}$ and $X_3$ are as defined above, with the proviso that $R_{34}$ and $X_3$ are not chlorine atoms at the same time, synthesized from a dihalogenated biphenyl compound and an anilide compound in the same manner as above. The condensate is then hydrolyzed to obtain a tetramine compound represented by the following formula:

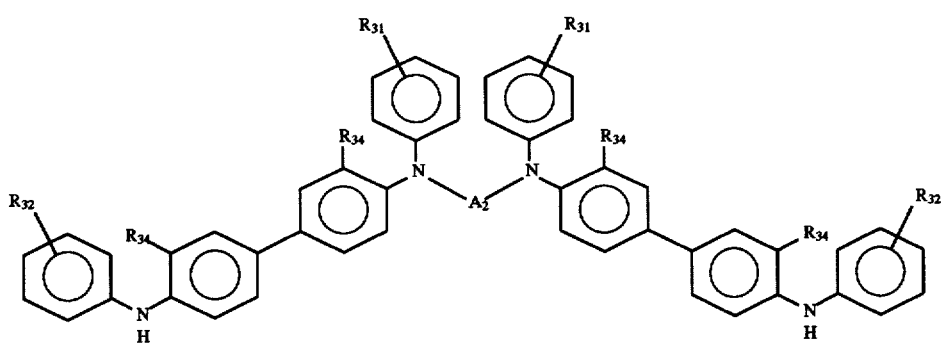

wherein $R_{31}$, $R_{32}$, $R_{34}$ and $A_2$ are as defined above. The tetramine compound thus obtained is then condensed with a halogenated aryl represented by the following formula:

wherein $R_{33}$ and $X_3$ are as defined above to obtain an amine compound of formula (III). Among the foregoing condensation reactions, the condensation reaction of 4,4'-dihalogenated biphenyl with an acetanilide compound may be effected by using benzanilide instead of the acetanilide compound.

The novel amine compound of formula (III) can easily form and stably maintain a glass state and is thermally and chemically stable. Thus, the amine compound of formula (III) is extremely useful as a hole-transporting material to be incorporated in organic electro-luminescence devices. Specific examples of the compound of formula (III) will be given below.

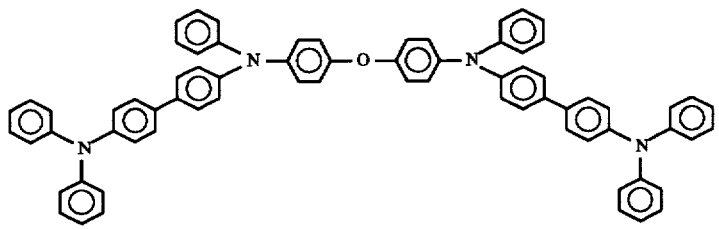

III-1

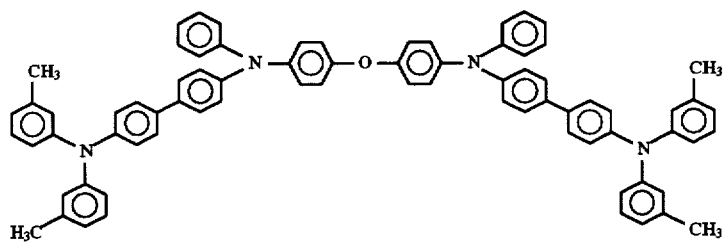

III-2

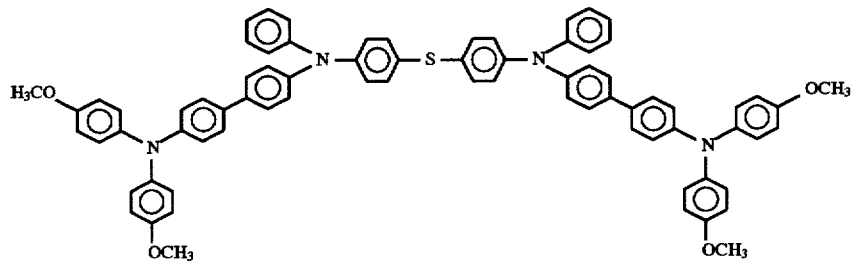

III-3

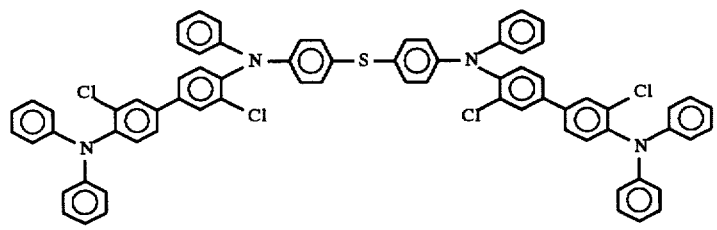

III-4

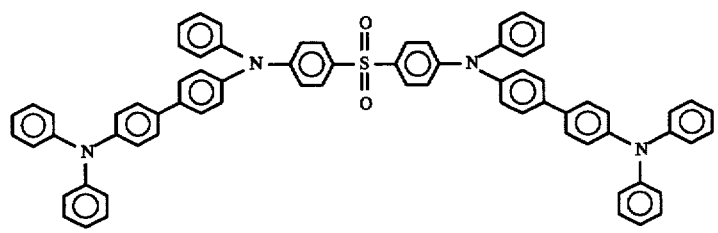

III-5

-continued

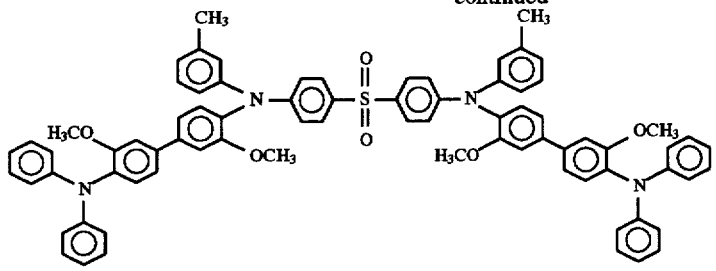
III-6

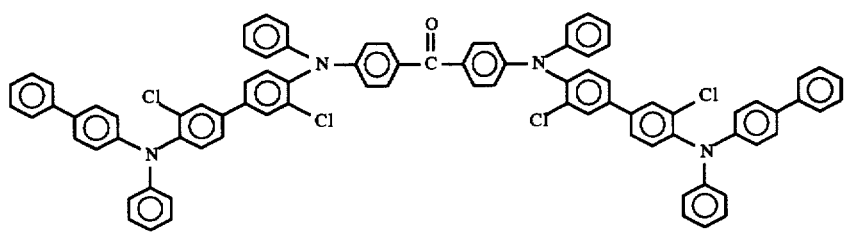
III-7

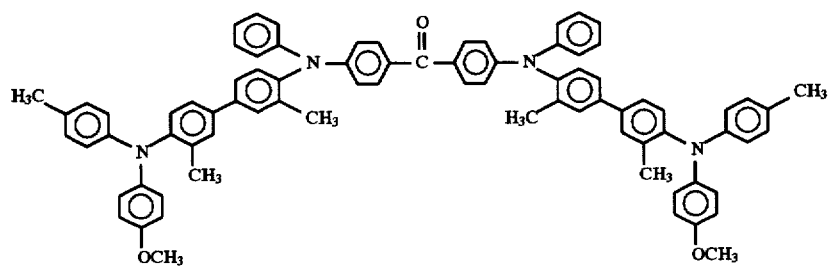
III-8

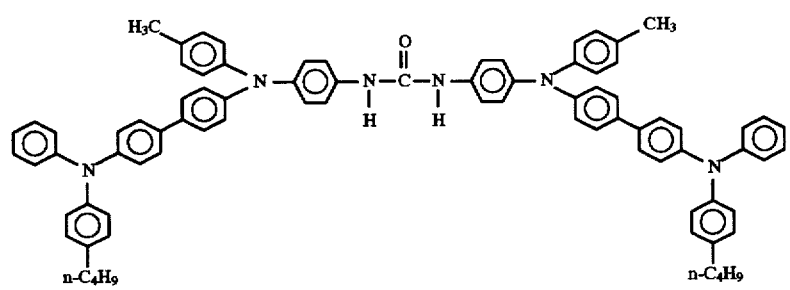
III-9

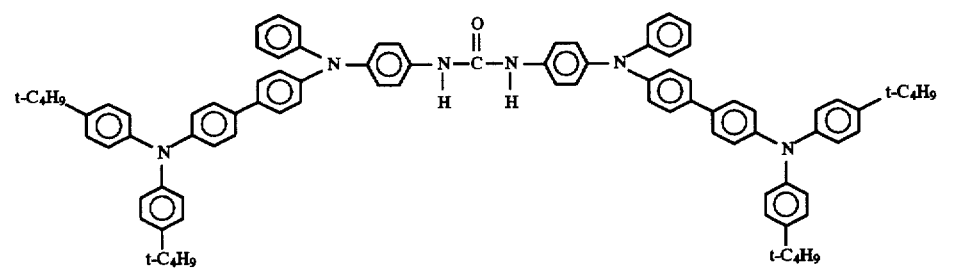
III-10

The synthesis of the amine compound of formula (III) will be further described in the following synthesis examples.

SYNTHESIS EXAMPLE 9

20.0 g (0.15 mol) of acetanilide, 65.0 g (0.16 mol) of 4,4'-diiodobiphenyl, 22.1 g (0.16 mol) of anhydrous potassium carbonate, 2.16 g (0.034 mol) of copper powder, and 35 ml of nitrobenzene were mixed. The reaction mixture was then allowed to undergo reaction at a temperature of 190° C. to 205° C. for 10 hours. The reaction product was then extracted with 200 ml of toluene. The insoluble contents were then removed by filtration. The filtrate was then concentrated to dryness. The concentrate was then purified by column chromatography (carrier: silica gel; elute: 6/1 mixture of toluene and ethyl acetate) to obtain 40.2 g (yield: 64.8%) of N-(4'-iodo-4-biphenylyl)acetanilide. The melting point of the product was from 135.0° C. to 136.0 ° C.

12.0 g (0.06 mol) of 4,4'-diamino-1,1'-diphenyl ether was dissolved in 100 ml of glacial acetic acid. 13.5 g (0.13 mol) of acetic anhydride was then added dropwise to the solution at a temperature of 40° C. After the completion of dropwise addition, the reaction mixture was then allowed to undergo reaction at a temperature of 45° C. for 2 hours. The reaction solution was then poured into 700 ml of ice water. The resulting crystal was filtered off, washed with water, and then dried. The crystal thus obtained was then recrystallized from 160 ml of methanol to obtain 13.4 g (yield: 78.3%) of 4,4'-diacetamide-1,1'-diphenyl ether. The melting point of the product was from 231.0° C. to 231.5° C.

Subsequently, 7.11 g (0.025 mol) of 4,4'-diacetamide-1,1'-diphenyl ether, 22.7 g (0.055 mol) of N-(4'-iodo-4-biphenylyl)acetanilide, 7.60 g (0.055 mol) of anhydrous potassium carbonate, 0.70 g (0.011 mol) of copper powder, and 10 ml of nitrobenzene were mixed. The reaction mixture was then allowed to undergo reaction at a temperature of 185° C. to 195° C. for 8 hours. The reaction product was then extracted with 500 ml of toluene. The insoluble contents were removed by filtration. The filtrate was then concentrated to obtain an oily matter. The oily matter thus obtained was then dissolved in 60 ml of isoamyl alcohol. The solution was then hydrolyzed with 1 ml of water and 1.8 g (0.027 mol) of 85% potassium hydroxide at a temperature of 130° C. The solution was then subjected to steam distillation to distill off isoamyl alcohol. The residue was extracted with 250 ml of toluene, washed with water, and then concentrated to dryness. The concentrate was then purified by column chromatography (carrier: silica gel; elute: 1/1 mixture of toluene and ethyl acetate) to obtain 8.93 g (yield: 52.0%) of 4,4'-bis(4'-anilino-4-biphenylylamino)-1,1'-diphenyl ether. The melting point of the product was from 285.5° C. to 286.5° C.

6.87 g (0.01 mol) of 4,4'-bis(4'-anilino-4-biphenylylamino)-1,1'-diphenyl ether, 24.5 g (0.12 mol) of iodobenzene, 6.08 g (0.044 mol) of anhydrous potassium carbonate, and 0.51 g (0.008 mol) of copper powder were mixed. The reaction mixture was then allowed to undergo reaction at a temperature of 195° C. to 210° C. for 16.5 hours. The reaction product was then extracted with 100 ml of toluene. The insoluble contents were then removed by filtration. The filtrate was then concentrated. To the concentrate was then added 350 ml of n-hexane to recover a crude crystal. The crude crystal thus recovered was then purified by column chromatography (carrier: silica gel; elute: 3/4 mixture of toluene and n-hexane) to obtain 4.06 g (yield: 41.0%) of 4,4'-bis(4'-diphenylamino-4-biphenylylanilinino)-1,1'-diphenyl ether. The melting point of the product was from 175.0° C. to 176.5° C.

Figure 9:
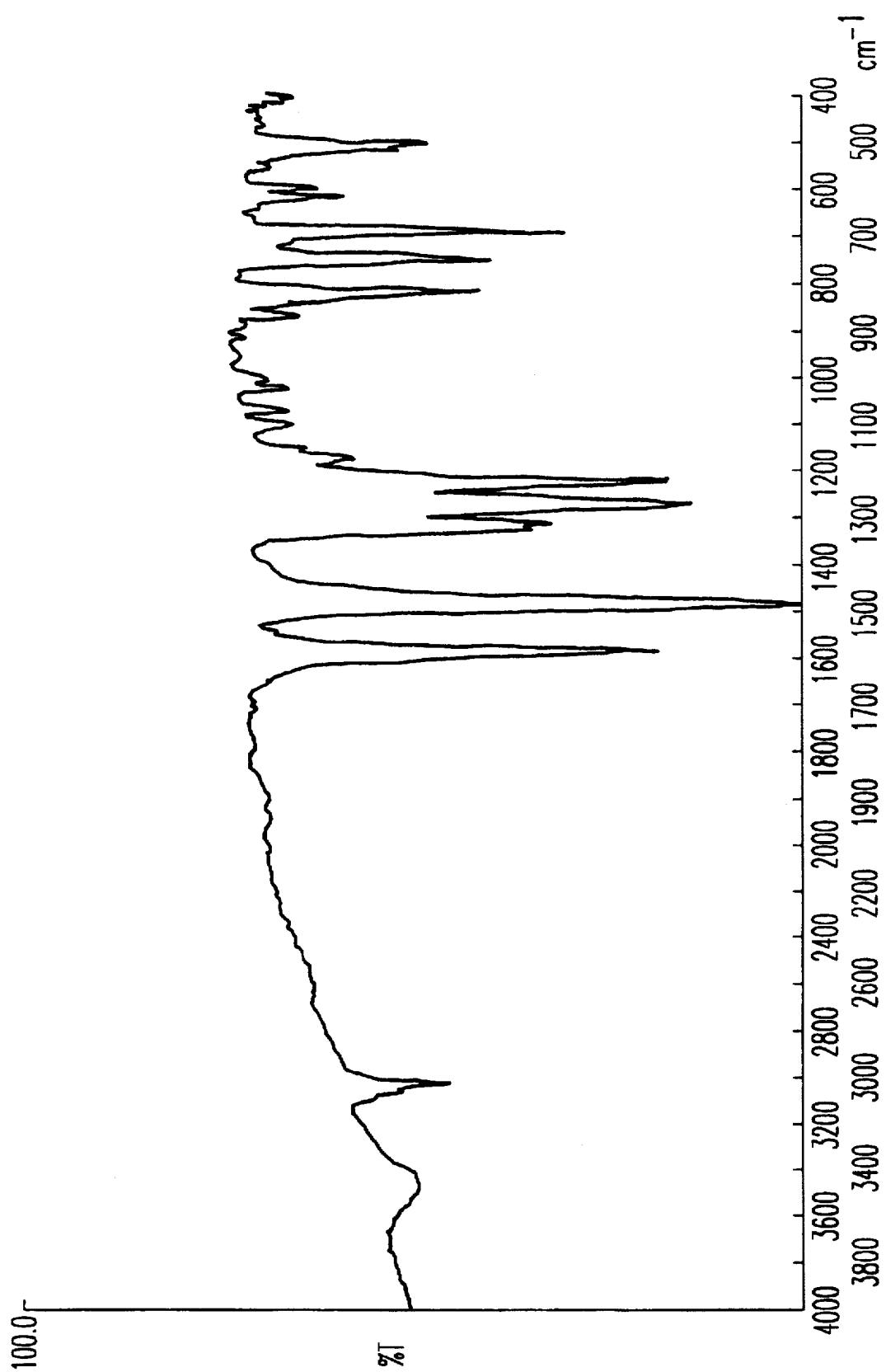
FIG. 9 shows the infrared absorption spectrum of 4,4'-bis(4'-diphenylamino-4-biphenylylanilinino)-1,1'-diphenyl ether.

FIG. 9 shows the infrared absorption spectrum of the compound obtained in Synthesis Example 9 (determined by KBr tablet process by means of IR-700 available from Nihon Bunko Kogyo K.K.).

The amine compound represented by formula (IV) is a novel compound. The synthesis of the amine compound of formula (IV) can be accomplished by the condensation reaction of the corresponding halogenated biphenylyldiphenylamine compound with the corresponding diamine compound. Alternatively, it can be accomplished by hydrolyzing the product of the condensation reaction of the corresponding halogenated biphenylyldiphenylamine compound with the corresponding amide compound to obtain a triamine compound, and then subjecting the triamine compound to condensation reaction with the corresponding dihalogenated compound. The condensation reaction is known as Ullmann reaction.

For example, a 4,4'-dihalogenated biphenyl compound represented by the following formula:

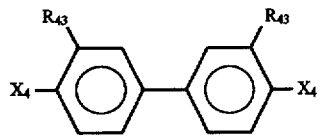

wherein $R_{43}$ is as defined above; and $X_4$ represents a chlorine atom, bromine atom or iodine atom, with the proviso that $R_{43}$ and $X_4$ are not chlorine atoms at the same time, is condensed with a diphenylamine compound represented by the following formula:

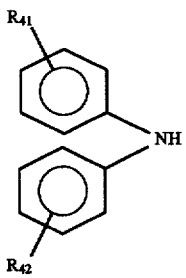

wherein $R_{41}$ and $R_{42}$ are as defined above in the same molar quantity, to obtain a 4'-halogenated biphenylyldiphenylamine compound represented by the following formula:

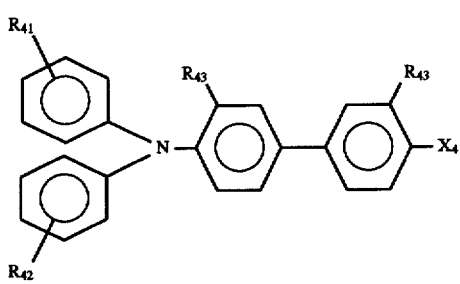

wherein $R_{41}$, $R_{42}$, $R_{43}$ and $X_4$ are as defined above, with the proviso that $R_{43}$ and $X_4$ are not chlorine atoms at the same time. Four equivalents of the 4'-halogenated biphenyldiphenylamine compound thus obtained are then allowed to act on one equivalent of a diamine compound represented by the following formula:

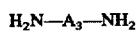

$$H_2N-A_3-NH_2$$

wherein $A_3$ and $R_{44}$ are as defined above to undergo condensation. Thus, an amine compound of the present invention is obtained.

Alternatively, two equivalents of a 4'-halogenated biphenylyldiphenylamine compound represented by the following formula:

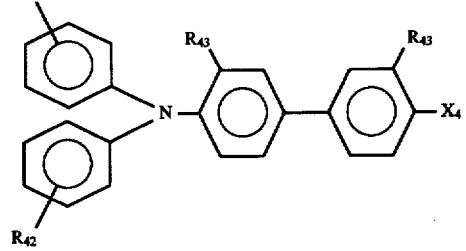

wherein $R_{41}$, $R_{42}$, $R_{43}$ and $X_4$ are as defined above, with the proviso that $R_{43}$ and $X_4$ are not chlorine atoms at the same time, synthesized from a dihalogenated biphenyl compound and a diphenylamine compound in the same manner as above are condensed with one equivalent of acetamide. The condensate is then hydrolyzed to obtain a triamine compound represented by the following formula:

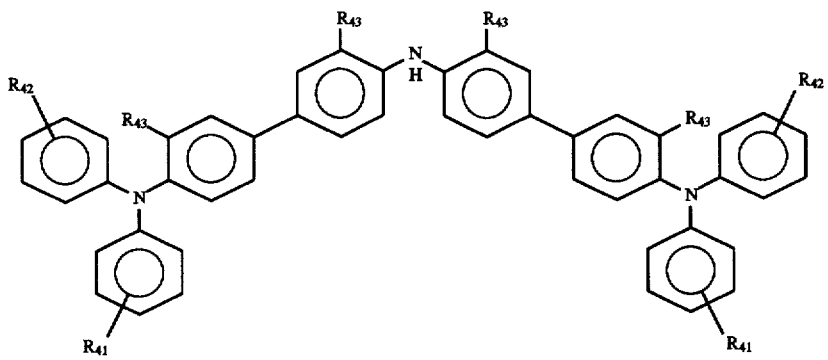

wherein $R_{41}$, $R_{42}$ and $R_{43}$ are as defined above. Two equivalents of the triamine compound are then allowed to act on one equivalent of a dihalogenated compound represented by the following formula:

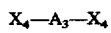

wherein $X_4$, $A_3$ and $R_{44}$ are as defined above, with the proviso that $X_4$ and $R_{44}$ are not chlorine atoms at the same time, to undergo condensation. Thus, a compound of the present invention can be obtained. Among the foregoing condensation reactions, the condensation reaction of two equivalents of 4'-halogenated biphenylyldiphenylamine compound with one equivalent of acetamide may be effected by using acetamide instead of benzamide.

The foregoing condensation reaction of various halogenated aryls with various amine compounds is effected in the presence or absence of solvent. As such a solvent there may be used nitrobenzene or dichlorobenzene. As a basic compound to be used a deacidification agent there may be used potassium carbonate, sodium carbonate, sodium hydrogencarbonate, potassium hydroxide, sodium hydroxide or the like. The condensation reaction may be also effected in the presence of a catalyst such as copper powder and halogenated copper. The reaction temperature is normally in the range of 160° to 230° C.

The novel amine compound of formula (IV) can easily form and stably maintain a glass state and is thermally and chemically stable. Thus, the amine compound of the present invention is extremely useful as a hole-transporting material to be incorporated in organic electro-luminescence devices.

Specific examples of the compound of formula (IV) will be given below.

IV-1

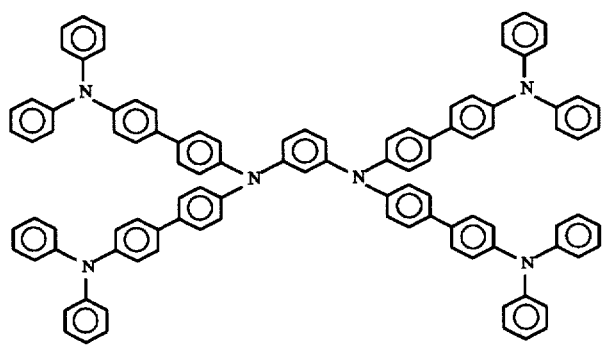

IV-2

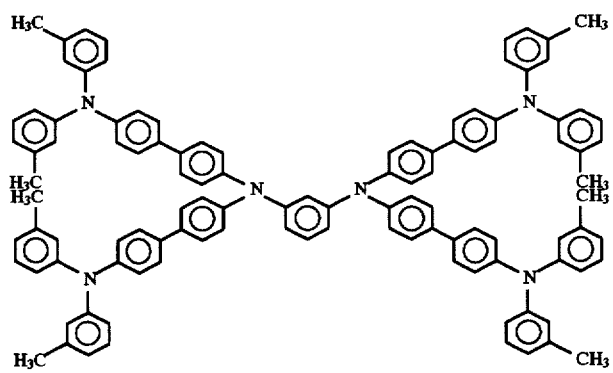

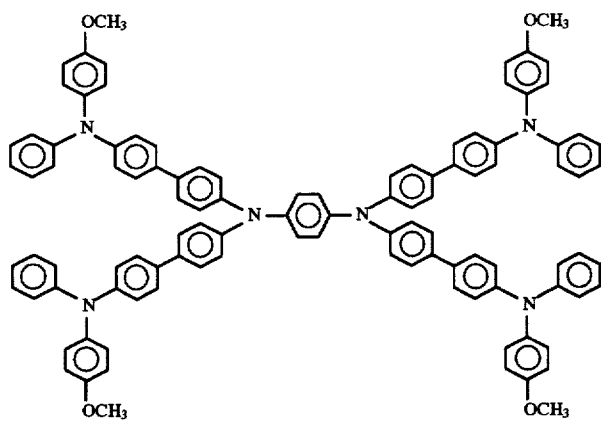
IV-3
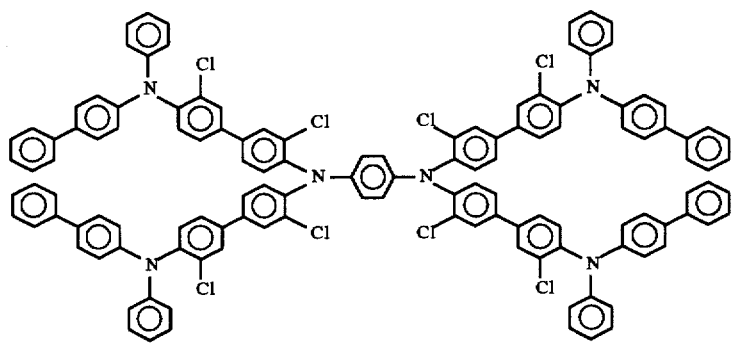
IV-4
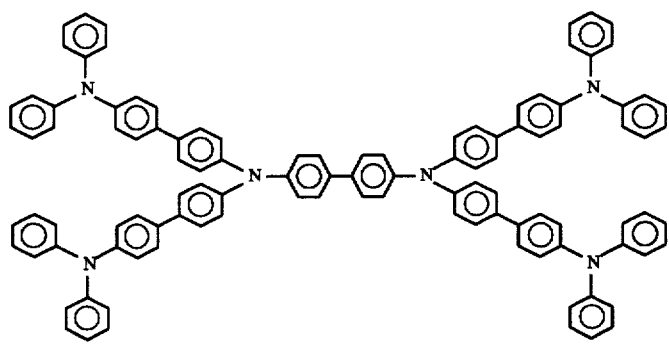
IV-5
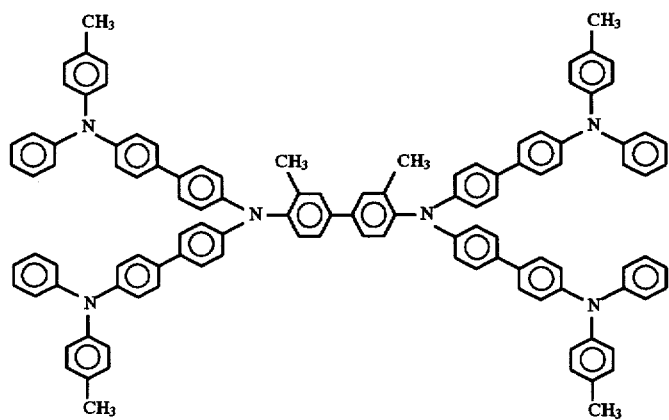
IV-6

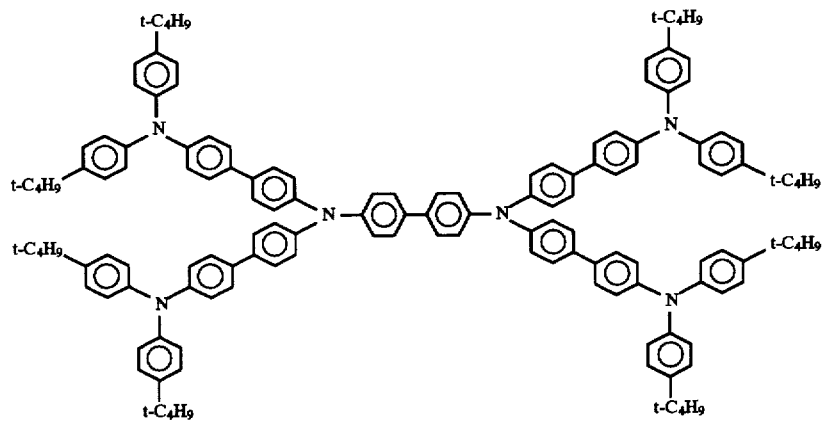
IV-7
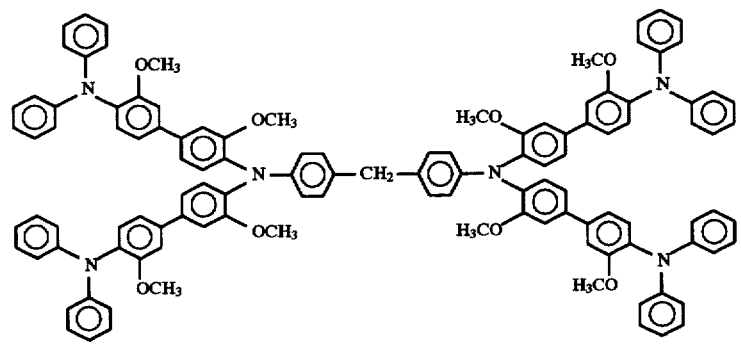
IV-8
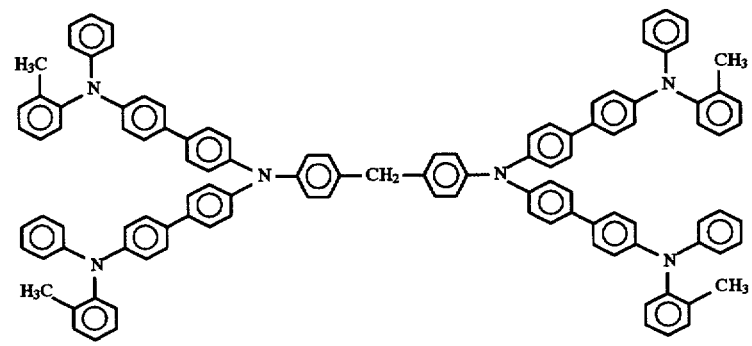
IV-9
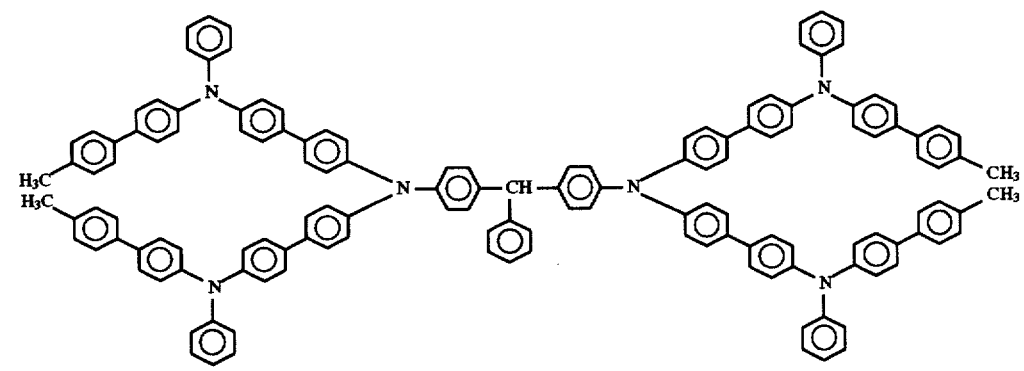
IV-10

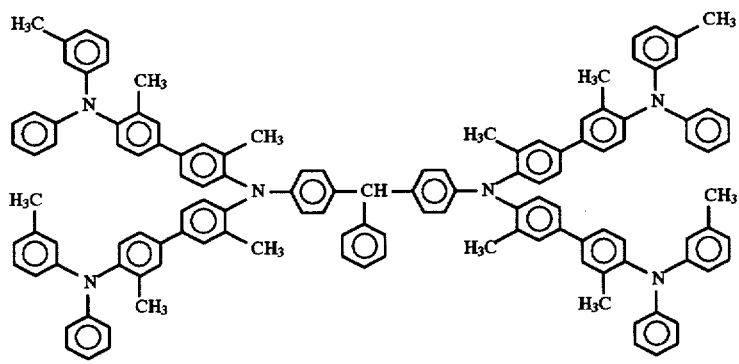
IV-11
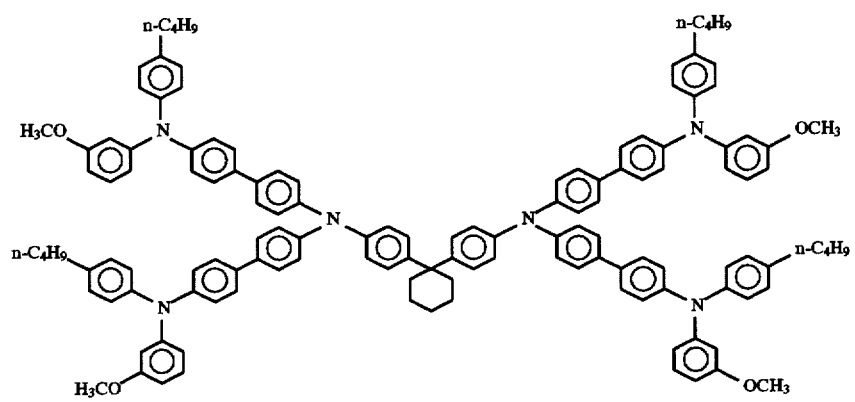
IV-12
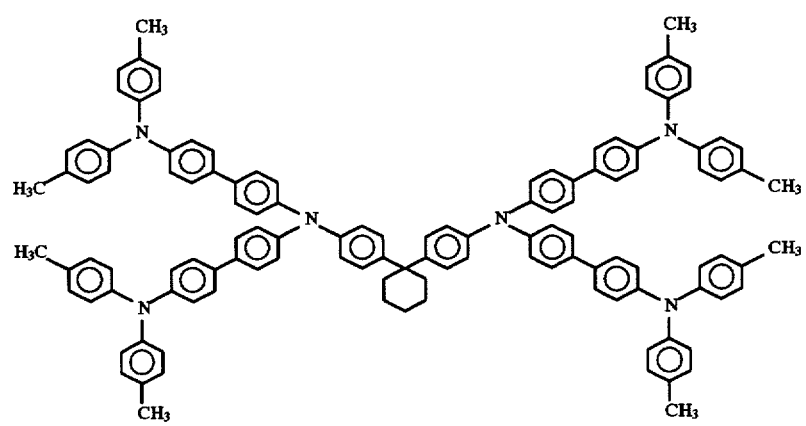
IV-13
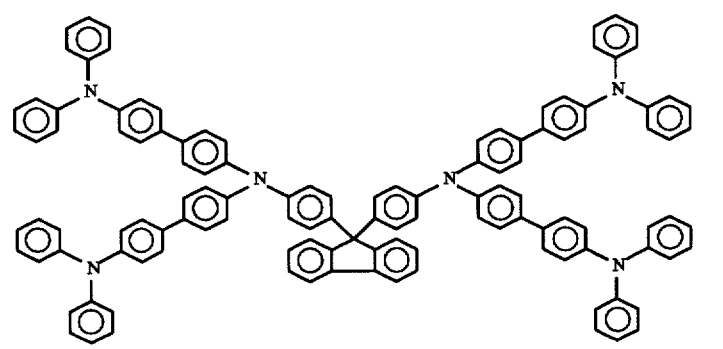
IV-14

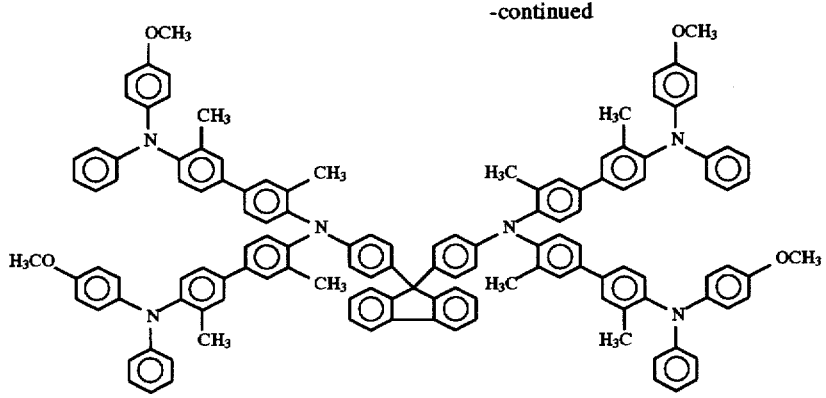

IV-15

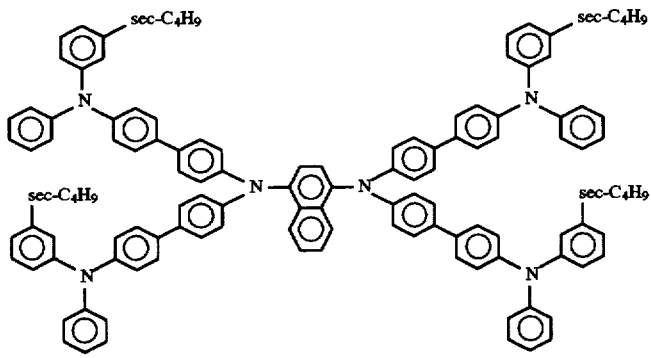

IV-16

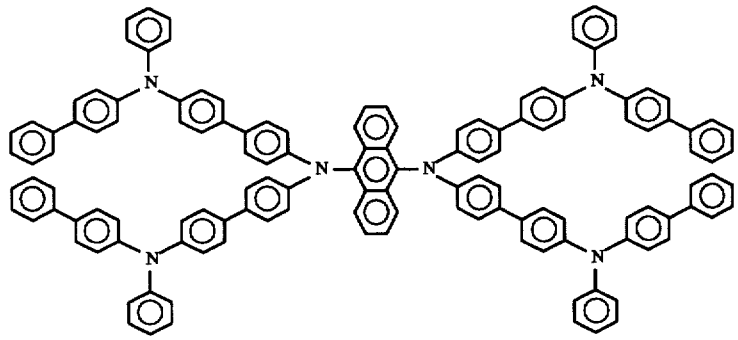

IV-17

The synthesis of the compounds of formula (IV) will be further described in the following examples.

SYNTHESIS EXAMPLE 10

16.9 g (0.10 mol) of diphenylamine, 48.7 g (0.12 mol) of 4,4'-diiodobiphenyl, 16.6 g (0.12 mol) of anhydrous potassium carbonate, 1.27 g (0.02 mol) of copper powder, and 20 ml of nitrobenzene were mixed. The reaction mixture was then allowed to undergo reaction at a temperature of 190° C. to 205° C. for 20 hours. The reaction product was then extracted with 200 ml of toluene. The insoluble contents were removed by filtration. The filtrate was then concentrated to dryness. The concentrate was then purified by column chromatography (carrier: silica gel; elute: 1/3 mixture of toluene and n-hexane) to obtain 24.9 g (yield: 55.6%) of N-(4'-iodo-4-biphenylyl)-N,N-diphenylamine. The melting point of the product was from 139.5° C. to 140.5° C.

Subsequently, 15.2 g (0.034 mol) of N-(4'-iodo-4-biphenylyl)-N,N-diphenylamine thus obtained, 0.95 g (0.016 mol) of acetamide, 4.70 g (0.034 mol) of anhydrous potassium carbonate, 0.19 g (0.003 mol) of copper powder, and 10 ml of nitrobenzene were mixed. The reaction mixture was then allowed to undergo reaction at a temperature of 200° to 212° C. for 15 hours. The reaction product was then extracted with 150 ml of toluene. The insoluble contents were then removed by filtration. The filtrate was then concentrated to obtain an oily matter. The oily matter thus obtained was then dissolved in 120 ml of isoamyl alcohol. The material was then hydrolyzed with 1 ml of water and 1.35 g (0.024 mol) of 85% potassium hydroxide at a temperature of 130° C. The reaction solution was then subjected to steam distillation to distill off isoamyl alcohol. The residue was extracted with 200 ml of toluene, washed with water, and then concentrated to dryness. The concentrate was then purified by column chromatography (carrier: silica gel; elute: 1/1 mixture of toluene and n-hexane) to obtain 7.47 g (yield: 71.2%) of N,N-bis(4'-diphenylamino-4-biphenylyl)amine. The melting point of the product was from 212.5° C. to 213.5° C.

7.21 g (0.011 mol) of N,N-bis(4'-diphenylamino-4-biphenylyl)amine thus obtained, 2.03 g (0.005 mol) of 4,4'-diiodobiphenyl, 1.52 g (0.011 mol) of anhydrous potassium carbonate, 0.13 g (0.002 mol) of copper powder, and 10 ml of nitrobenzene were mixed. The reaction mixture was then allowed to undergo reaction at a temperature of 195° C to 210° C. for 15 hours. The reaction product was then extracted with 100 ml of toluene. The insoluble contents were removed by filtration. The filtrate was then concentrated. To the concentrate was then added 120 ml of n-hexane to recover a crude crystal. The crude crystal thus recovered was then purified by column chromatography (carrier: silica gel; elute: 1/1 mixture of toluene and n-hexane) to obtain 4.16 g (yield: 56.9%) of N,N,N',N'-tetrakis(4'-diphenylamino-4-biphenylyl)benzidine. The product was molten at a temperature of 188° C. to 191° C. Thus, the melting point of the product was indefinite. The elementary analysis and infrared absorption spectrum of the product (determined by KBr tablet process by means of IR-700 available from Nihon Bunko Kogyo K.K.) are as follows:

Elementary analysis: Measured %: C 88.78, H 5.58, N 5.69 Calculated %: C 88.74, H 5.51, N 5.75

Infrared absorption spectrum: 3,028 $cm^{-1}$, 1,591 $cm^{-1}$, 1,488 $cm^{-1}$, 1,319 $cm^{-1}$, 1,275 $cm^{-1}$, 1,176 $cm^{-1}$, 818 $cm^{-1}$, 753 $cm^{-1}$, 697 $cm^{-1}$

SYNTHESIS EXAMPLE 11

20.3 g (0.12 mol) of diphenylamine, 60.9 g (0.15 mol) of 4,4'-diiodobiphenyl, 19.3 g (0.14 mol) of anhydrous potassium carbonate, 1.52 g (0.024 mol) of copper powder, and 20 ml of nitrobenzene were mixed. The reaction mixture was then allowed to undergo reaction at a temperature of 190° C. to 205° C. for 21 hours. The reaction product was then extracted with 200 ml of toluene. The insoluble contents were removed by filtration. The filtrate was then concentrated to dryness. The concentrate was then purified by column chromatography (carrier: silica gel; elute: 1/3 mixture of toluene and n-hexane) to obtain 29.0 g (yield: 54.1%) of N-(4'-iodo-4-biphenylyl)-N,N-diphenylamine. The melting point of the product was from 139.5° C. to 140.5° C.

Subsequently, 22.8 g (0.051 mol) of N-(4'-iodo-4-biphenylyl)-N,N-diphenylamine thus obtained, 2.55 g (0.012 mol) of o-tolidine, 6.91 g (0.050 mol) of anhydrous potassium carbonate, 0.64 g (0.001 mol) of copper powder, and 10 ml of nitrobenzene were mixed. The reaction mixture was then allowed to undergo reaction at a temperature of 200° to 212° C. for 28 hours. The reaction product was then extracted with 160 ml of toluene. The insoluble contents were then removed by filtration. The filtrate was then concentrated to dryness. The solid matter thus obtained was then purified by column chromatography (carrier: silica gel; elute: 1/1 mixture of toluene and n-hexane) to obtain 9.94 g (yield: 55.6%) of N,N,N',N'-tetrakis(4'-diphenylamino-4-biphenylyl)-o-tolidine. The melting point of the product was from 196° C. to 203°0 C. Thus, the melting point of the product was indefinite. The elementary analysis and infrared absorption spectrum of the product are as follows:

Elementary analysis: Measured %: C 88.67, H 5.78, N 5.56 Calculated %: C 88.68, H 5.68, N 5.64

Infrared absorption spectrum: 3,026 $cm^{-1}$, 1,589 $cm^{-1}$, 1,486 $cm^{-1}$, 1,314 $cm^{-1}$, 1,270 $cm^{-1}$, 1,176 $cm^{-1}$, 816 $cm^{-1}$, 752 $cm^{-1}$, 696 $cm^{-1}$

SYNTHESIS EXAMPLE 12

20.3 g (0.12 mol) of diphenylamine, 65.1 g (0.15 mol) of 3,3'-dimethyl-4,4'-diiodobiphenyl, 19.3 g (0.14 mol) of anhydrous potassium carbonate, 1.52 g (0.024 mol) of copper powder, and 20 ml of nitrobenzene were mixed. The reaction mixture was then allowed to undergo reaction at a temperature of 190° C. to 205° C. for 21 hours. The reaction product was then extracted with 200 ml of toluene. The insoluble contents were removed by filtration. The filtrate was then concentrated to dryness. The concentrate was then purified by column chromatography (carrier: silica gel; elute: 2/7 mixture of toluene and n-hexane) to obtain 32.6 g (yield: 57.2%) of N-(3,3'-dimethyl-4'-iodo-4-biphenylyl)-N, N-diphenylamine.

Subsequently, 24.2 g (0.051 mol) of N-(3,3'-dimethyl-4'-iodo-4-biphenylyl)-N,N-diphenylamine thus obtained, 2.55 g (0.012 mol) of o-tolidine, 6.91 g (0.050 mol) of anhydrous potassium carbonate, 0.64 g (0.001 mol) of copper powder, and 10 ml of nitrobenzene were mixed. The reaction mixture was then allowed to undergo reaction at a temperature of 200° to 212° C. for 30 hours. The reaction product was then extracted with 150 ml of toluene. The insoluble contents were then removed by filtration. The filtrate was then concentrated to dryness. The solid matter thus obtained was then purified by column chromatography (carrier: silica gel; elute: 3/4 mixture of toluene and n-hexane) to obtain 9.48 g (yield: 49.3%) of N,N,N',N'-tetrakis(3,3'-dimethyl-4'-diphenylamino-4-biphenylyl)-o-tolidine. The product was molten at a temperature of 196° C. to 212° C. Thus, the melting point of the product was indefinite. The elementary analysis and infrared absorption spectrum of the product are as follows:

Elementary analysis: Measured %: C 88.53, H 6.24, N 5.21 Calculated %: C 88.46, H 6.29, N 5.25

Infrared absorption spectrum: 3,026 $cm^{-1}$, 1,589 $cm^{-1}$, 1,486 $cm^{-1}$, 1,314 $cm^{-1}$, 1,270 $cm^{-1}$, 1,176 $cm^{-1}$, 816 $cm^{-1}$, 752 $cm^{-1}$, 696 $cm^{-1}$ The amino compound of formula (V) is a novel compound. The synthesis of the amine compound of formula (V) can be accomplished by the condensation reaction of the corresponding halogenated biphenylyldiphenylamine compound with the corresponding diamine compound. Alternatively, it can be accomplished by hydrolyzing the product of the condensation reaction of the corresponding halogenated biphenylyldiphenylamine compound with the corresponding amide compound to obtain a triamine compound, and then subjecting the triamine compound to condensation reaction with the corresponding dihalogenated compound. The condensation reaction is known as Ullmann reaction.

For example, a 4,4'-dihalogenated biphenyl compound represented by the following formula:

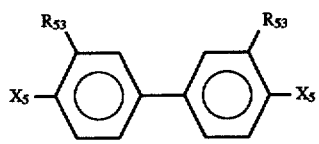

wherein $R_{53}$ is as defined above; and $X_5$ represents a chlorine atom, bromine atom or iodine atom, with the proviso that $R_{53}$ and $X_5$ are not chlorine atoms at the same time, is condensed with a diphenylamine compound represented by the following formula:

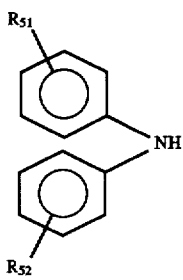

wherein $R_{51}$, and $R_{52}$ are as defined above in the same molar quantity, to obtain a 4'-halogenated biphenylyldiphenylamine compound represented by the following formula:

Alternatively, two equivalents of a 4'-halogenated biphenylyldiphenylamine compound represented by the following formula:

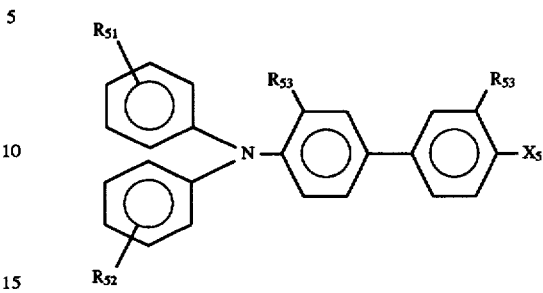

wherein $R_{51}$, $R_{52}$, $R_{53}$ and $X_5$ are as defined above, with the proviso that $R_{53}$ and $X_5$ are not chlorine atoms at the same time, synthesized from a dihalogenated biphenyl compound and a diphenylamine compound in the same manner as above are condensed with one equivalent of acetamide. The condensate is then hydrolyzed to obtain a triamine compound represented by the following formula:

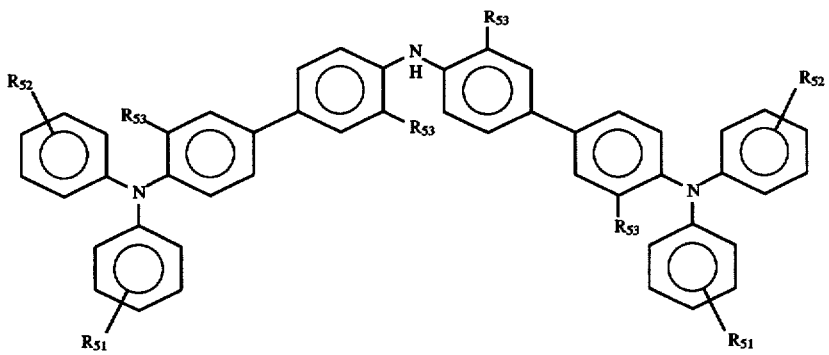

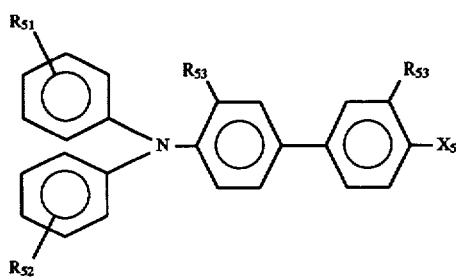

wherein $R_{51}$, $R_{52}$, $R_{53}$ and $X_5$ are as defined above, with the proviso that $R_{53}$ and $X_5$ are not chlorine atoms at the same time. Four equivalents of the 4'-halogenated biphenyldiphenylamine compound thus obtained are then allowed to act on one equivalent of a diamine compound represented by the following formula $$H_2N-A_4-NH_2$$

wherein $A_4$ is as defined above to undergo condensation. Thus, an amine compound of the present invention is obtained.

wherein $R_{51}$, $R_{52}$ and $R_{53}$ are as defined above. Two equivalents of the triamine compound are then allowed to act on one equivalent of a dihalogenated compound represented by the following formula:

$$X_5-A_4-X_5$$

wherein $X_5$ and $A_4$ are as defined above, to undergo condensation. Thus, the compound of formula (V) can be obtained. Among the foregoing condensation reactions, the condensation reaction of two equivalents of 4'-halogenated biphenylyldiphenylamine compound with one equivalent of acetamide may be effected by using acetamide instead of benzamide.

The foregoing condensation reaction of various halogenated aryls with various amine compounds is effected in the presence or absence of solvent. As such a solvent there may be used nitrobenzene or dichlorobenzene. As a basic compound to be used a deacidification agent there may be used potassium carbonate, sodium carbonate, sodium hydrogencarbonate, potassium hydroxide, sodium hydroxide or the like. The condensation reaction may be also effected in the presence of a catalyst such as copper powder and halogenated copper. The reaction temperature is normally in the range of 160° to 230° C.

The novel amine compound of formula (V) can easily form and stably maintain a glass state and is thermally and chemically stable. Thus, the amine compound is extremely useful as a hole-transporting material to be incorporated in organic electro-luminescence devices.

Specific examples of the compound of formula (V) will be given below.

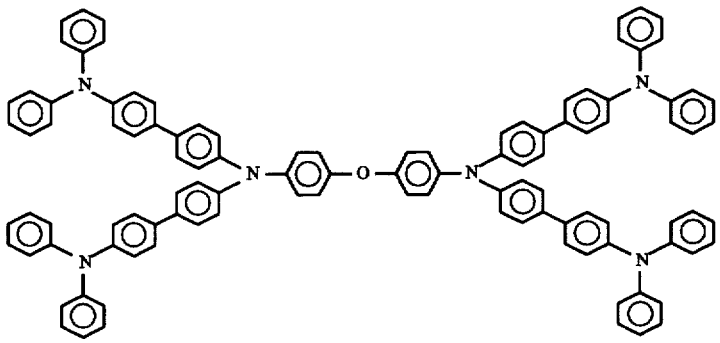

V-1

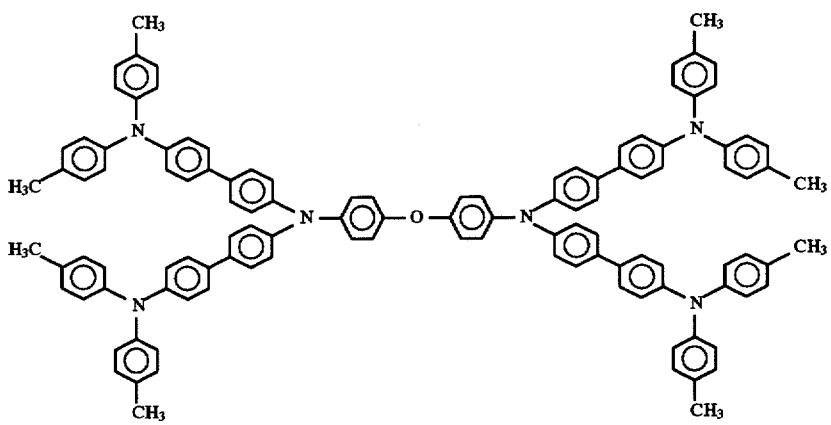

V-2

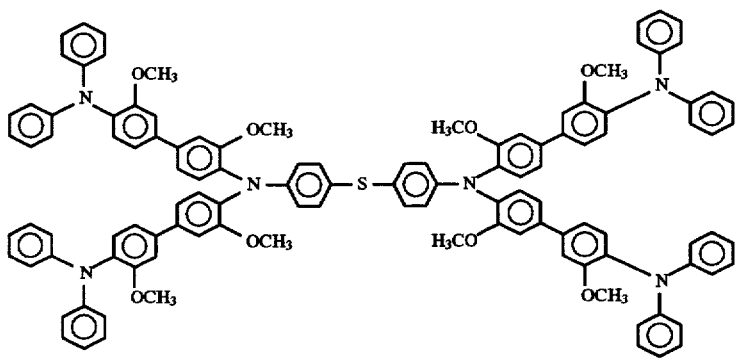

V-3

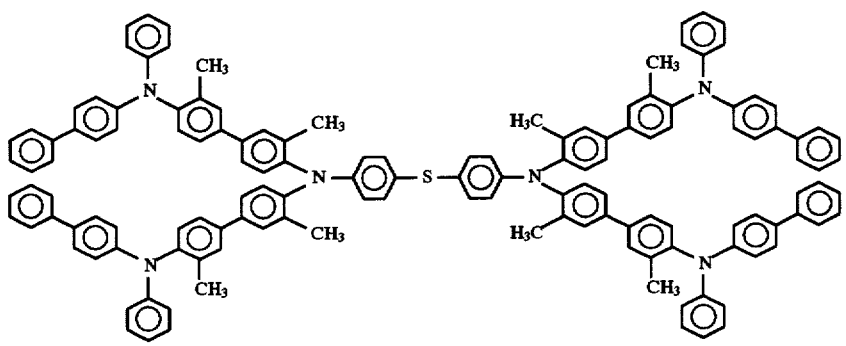

V-4

-continued
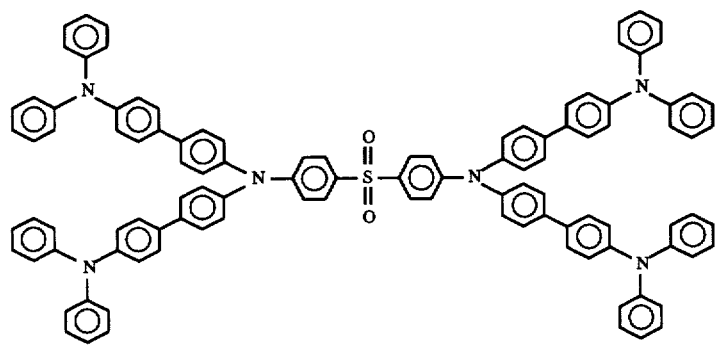
V-5
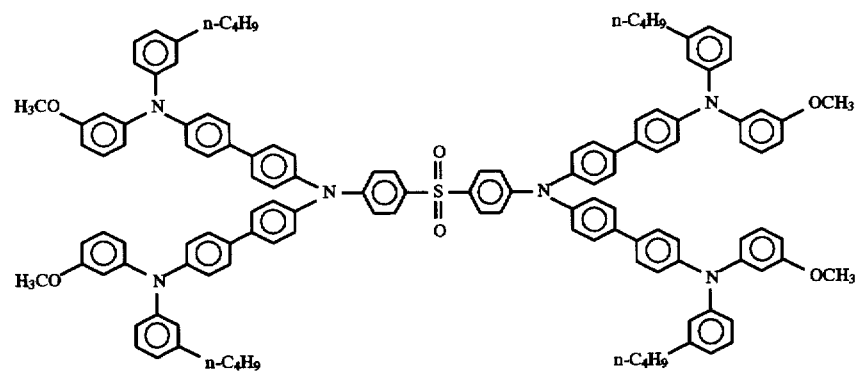
V-6
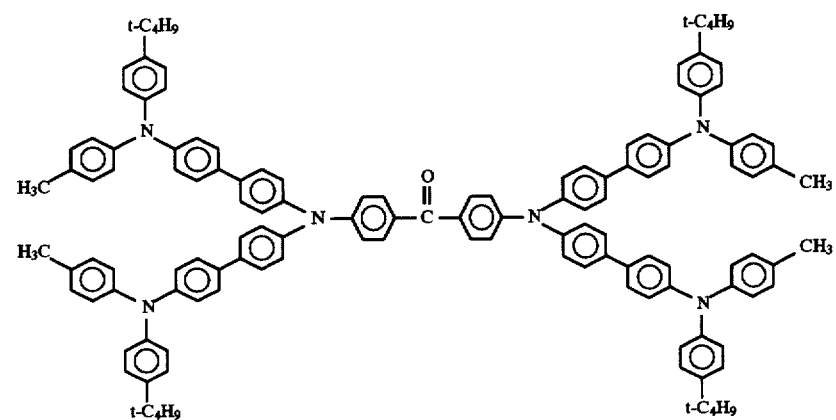
V-7
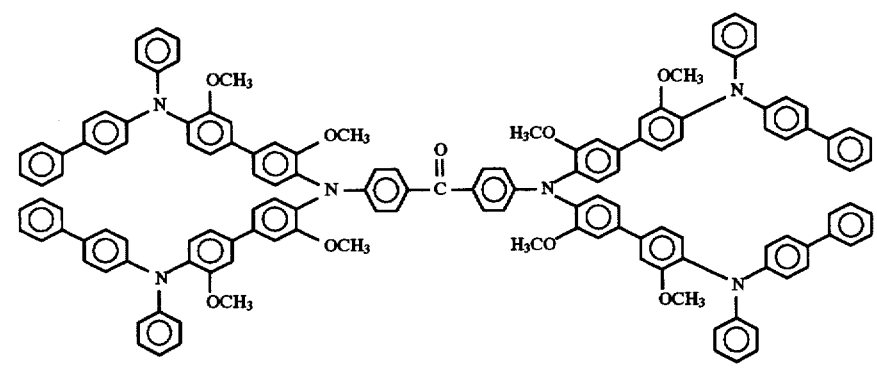
V-8

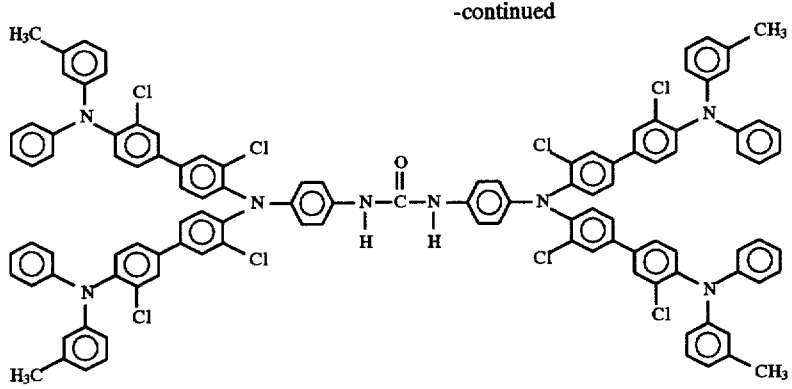

V-9

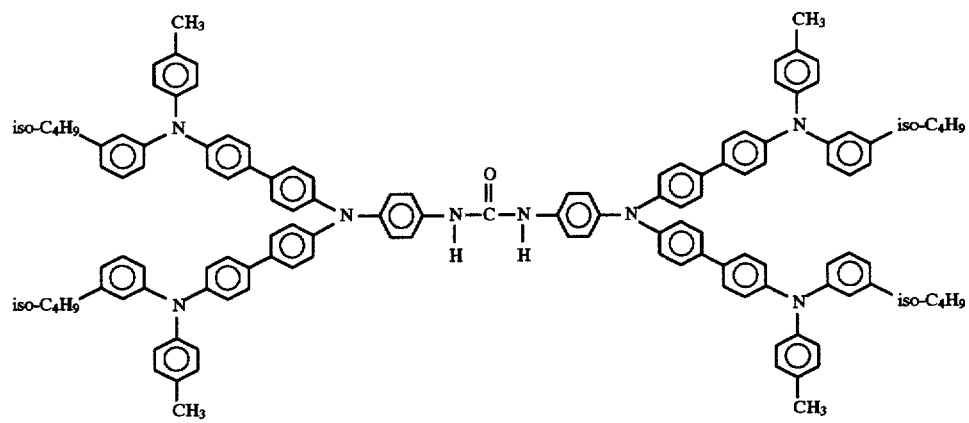

V-10

The amine compounds of formula (VI) which are used for the organic EL device according to the present invention can be synthesized as follows.

The synthesis of the amine compound of formula (VI) can be accomplished by hydrolyzing the product of the condensation reaction of the corresponding halogenated biphenylyldiphenylamine compound with the corresponding amide compound to obtain a triamine compound, and then subjecting the triamine compound to condensation reaction with the corresponding halogenated biphenylyldiphenylamine compound. These condensation reactions are known as Ullmann reaction.

The synthesis of the amine compounds of formula (VI) will be further described in the following synthesis examples.

SYNTHESIS EXAMPLE 13

16.9 g (0.10 mol) of diphenylamine, 48.7 g (0.12 mol) of 4,4'-diiodobiphenyl, 16.6 g (0.12 mol) of anhydrous potassium carbonate, 1.27 g (0.02 mol) of copper powder, and 20 ml of nitrobenzene were mixed. The reaction mixture was then allowed to undergo reaction at a temperature of 190° C. to 205° for 20 hours. The reaction product was then extracted with 200 ml of toluene. The insoluble contents were removed by filtration. The filtrate was then concentrated to dryness. The concentrate was then purified by column chromatography (carrier: silica gel; elute: 1/3 mixture of toluene and n-hexane) to obtain 24.9 g (yield: 55.6%) of N-(4'-iodo-4-biphenylyl)-N,N-diphenylamine. The melting point of the product was from 139.5° C. to 140.5° C.

Subsequently, 15.2 g (0.034 mol) of N-(4'-iodo-4-biphenylyl)-N,N-diphenylamine thus obtained, 0.95 g (0.016 mol) of acetamide, 4.70 g (0.034 mol) of anhydrous potassium carbonate, 0.19 g (0.003 mol) of copper powder, and 10 ml of nitrobenzene were mixed. The reaction mixture was then allowed to undergo reaction at a temperature of 200° to 212° C. for 15 hours. The reaction product was then extracted with 150 ml of toluene. The insoluble contents were then removed by filtration. The filtrate was then concentrated to obtain an oily matter. The oily matter thus obtained was then dissolved in 120 ml of isoamyl alcohol. The reaction solution was then hydrolyzed with 1 ml of water and 1.35 g (0.024 mol) of 85% potassium hydroxide at a temperature of 130° C. The reaction solution was then subjected to steam distillation to distill off isoamyl alcohol. The residue was extracted with 200 ml of toluene, washed with water, and then concentrated to dryness. The concentrate was then purified by column chromatography (carrier: silica gel; elute: 1/1 mixture of toluene and n-hexane) to obtain 7.47 g (yield: 71.2%) of N,N-bis(4'-diphenylamino-4-biphenylyl)amine. The melting point of the product was from 212.5° C. to 213.5° C.

6.56 g (0.01 mol) of N,N-bis(4'-diphenylamino-4-biphenylyl)amine thus obtained, 4.92 g (0.011 mol) of N-(4'-iodo-4-biphenylyl)-N,N-diphenylamine, 1.52 g (0.011 mol) of anhydrous potassium carbonate, 0.13 g (0.002 mol) of copper powder, and 10 ml of nitrobenzene were mixed. The reaction mixture was then allowed to undergo reaction at a temperature of 195° C. to 210° C. for 15 hours. The reaction product was then extracted with 100 ml of toluene. The insoluble contents were removed by filtration. To the filtrate was then added 120 ml of n-hexane to recover a crude crystal. The crude crystal thus obtained was then purified by column chromatography to obtain 4.89 g (yield: 50.2%) of N,N,N-tris(4'-diphenylamino-4-biphenylyl)amine. The product was molten at a temperature of 250° C. to 278° C. Thus, the melting point of the product was indefinite. The results of elementary analysis and infrared absorption spectrum are as follows.

Elementary analysis: Measured %: C 88.78, H 5.51, N 5.82 Calculated %: C 88.67, H 5.58, N 5.75

Infrared absorption spectrum: 3,028 cm$^{-1}$, 1,590 cm$^{-1}$, 1,487 cm$^{-1}$, 1,322 cm$^{-1}$, 1,277 cm$^{-1}$, 1,176 cm$^{-1}$, 820 cm$^{-1}$, 753 cm$^{-1}$, 697 cm$^{-1}$ In order to demonstrate that the amine compounds of formulas (I) to (V) are useful and organic EL devices comprising the amine compounds of formulas (I) to (VI) as a hole-transporting material are excellent in luminescence characteristics, lumunescence stability and storage stability, the inventors prepared and evaluated organic EL devices comprising an ITO electrode, a hole-transporting layer, a light-emitting layer, and a magnesium/silver electrode. As the light-emitting material, an Alq having an electron-transporting property was used. As the hole-transporting materials there were used amine compounds represented by formulae (I) to (VI).

Figure 10:
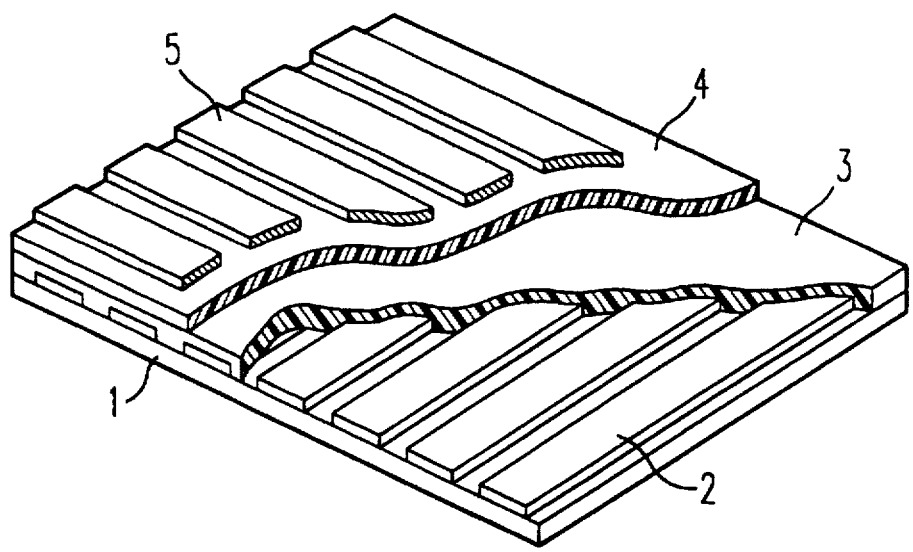
FIG. 10 shows the configuration of an embodiment of the organic EL device according to the present invention.

The organic EL device was prepared by vacuum-evaporating a hole-transporting layer 3, an electron-transporting/light-emitting layer 4, and an Mg/Ag electrode 5 in this order onto an ITO electrode which had been previously formed on a glass substrate as a transparent electrode 2 as shown in FIG. 10. In some detail, a glass substrate (on which an ITO electrode has been formed) which had been thoroughly washed, a hole-transporting material, and a purified Alq as an electron-transporting light-emitting material were charged in an evaporating apparatus. The evaporating apparatus was then evacuated to $10^{-31}$ 6 torr. The hole-transporting layer was then evaporated onto the glass substrate at a rate of 0.1 nm/sec. to a thickness of 50 nm. The evaporation of the Alq onto the hole-transporting layer thus deposited was effected at the same rate as above. The film thickness was 50 nm. The evaporation of the Mg/Ag electrode was effected at a rate of 0.4 nm/sec. The film thickness was 100 nm. The sequential evaporation processes were continuously effected without interrupting vacuum. The film thickness was monitored by means of a quartz crystal oscillator. Immediately after the preparation of the device, the electrode was taken out in dried nitrogen. Subsequently, the device was measured for properties.

The luminescence of the device thus obtained is defined as the luminance of light emitted by the application of 100 mA/cm$^2$. For the evaluation of the luminescence stability, the change in the luminance of light emitted by the continuous application of current giving light of 200 cd/m$^2$ is measured. The luminescent life is defined as the time required until the luminance is halved to 100 cd/m$^2$. The storage stability of the device is defined as the time required until the luminance of light emitted by the application of current of 20 mA/cm$^2$ to the device which has been allowed to stand at room temperature in dried air for a predetermined period of time is reduced to half of the initial luminance.

While an Alq was used as an electron-transporting light-emitting layer 4 for the evaluation of the hole-transporting material of the present invention, various materials such as rare earth complexes, oxazole derivatives and pol-p-phenylene vinylenes may be used as a material for a light-emitting layer. An organic EL device with even higher performances can be prepared by incorporating dopants such as quinacridone and coumarin in the light-emitting layer. Alternatively, an organic EL device comprising an electron-transporting layer, a light-emitting layer and a hole-transporting layer may be prepared. Also, the hole-transporting material of the present invention can be combined with a proper electron-transporting material to use the hole-transporting layer also as a light-emitting layer.

Examples of the substrate include a glass. Examples of the electrode to be formed on a substrate include an ITO. Examples of the electron transporting material include Alq, triazole and oxadiazole. Examples of the electrode to be formed on the electron-transporting layer include Mg/Ag, Al and Al/Li.

The thickness of the electrode is preferably from 100 to 200 nm. The thickness of the hole-transporting layer, electron-transporting layer and light-emitting layer each is preferably from 10 to 200 nm.

Hole-transporting materials of the present invention can be used singly or in admixture. In the latter case, two or more hole-transporting materials may be vacuum-evaporated at the same time. Alternatively, a hole-transporting material of the present invention may be vacuum-evaporated together with conventional hole-transporting materials such as TPAC and TPD. If two or more hole-transporting materials are vacuum-evaporated at the same time, it exerts an effect of inhibiting the crystallization of the hole-transporting layer.

Next, the organic EL devices according to the present invention will be described in detail in reference to the device examples.

DEVICE EXAMPLE 1

A glass substrate having an ITO electrode formed thereon which had been thoroughly washed, an amine compound of formula (I) wherein $R_{11}$ is p-n-Bu, $R_{12}$ is H, and $R_{13}$ is H having a melting point of 132.9° C. (hereinafter Compound (1)) as a hole-transporting material, and a purified Alq as an electron-transporting light-emitting material were charged in an evaporating apparatus. Compound (1) was then evaporated onto the ITO electrode at a rate of 0.1 nm/sec. to a thickness of 50 nm. The film thickness was monitored by means of a quartz crystal oscillator. The evaporation of the Alq onto the hole-transporting layer thus deposited was effected at the same rate as above. The film thickness was 50 nm. The evaporation of the Mg/Ag electrode was effected at a rate of 0.4 nm/sec. The film thickness was 100 nm. The sequential evaporation processes were continuously effected without interrupting vacuum. Immediately after the preparation of the device, the electrode was taken out in dried nitrogen. Subsequently, the device was measured for properties. As a result, the product exhibited a luminescence of 2,500 cd/m$^2$, a luminescent life of 620 hours and a storage stability of 2,200 hours.

For comparison, EL devices were prepared in the same manner as above except that TPD and TPAC were used as hole-transporting materials, respectively. These EL devices were then examined for properties. As a result, the EL device prepared from TPD exhibited a luminescence of 2,200 cd/m$^2$, a luminescent life of 220 hours and a storage stability of 460 hours. On the other hand, the EL device prepared from TPAC exhibited a luminescence of 2,500 cd/m$^2$, a luminescent life of 280 hours and a storage stability of 560 hours. This shows that Compound (1) of the present invention can provide a long luminescent life and an excellent storage stability.

DEVICE EXAMPLE 2

EL devices were prepared and evaluated in the same manner as in Device Example 1 except that the following compounds of formula (I) were used as hole-transporting materials, respectively.

| Compound No. | Formula (I) | | |
| --- | --- | --- | --- |
| | $R_{11}$ | $R_{12}$ | $R_{13}$ |
| (2) | i-Bu | H | H |
| (3) | i-Bu | H | $CH_3$ |
| (4) | t-Bu | H | H |
| (5) | t-Bu | t-Bu | H |
| (6) | $C_6H_5$ | H | H |
| (7) | $C_6H_5$ | $C_6H_5$ | H |
| (8) | $C_6H_5$ | $C_6H_5$ | $CH_3$ |
| (9) | p-$CH_3$—$C_6H_4$ | H | $OCH_3$ |
| (10) | p-$CH_3$—$C_6H_4$ | p-$CH_3$—$C_6H_4$ | H |

The results are set forth in Table 3. In Compounds (2) to (10), $R_{11}$ and $R_{12}$ are all on p-positions (4-positions). This shows that Compounds (2) to (10) of formula (I) can provide a long luminescent life and an excellent storage stability.

DEVICE EXAMPLE 3

EL devices were prepared and evaluated in the same manner as in Device Example 1 except that the following compounds of formula (II) were used as hole-transporting

| Compound No. | Formula (II) | | | | | |
| --- | --- | --- | --- | --- | --- | --- |
| | $R_{21}$ | $R_{22}$ | $R_{23}$ | $R_{24}$ | $A_1$ | $R_{25}$ |
| (11) | H | H | H | H | (a1) | |
| (12) | H | H | H | H | (b1) | |
| (13) | H | H | H | H | (c1) | H |
| (14) | H | H | H | $CH_3$ | (c1) | $CH_3$ |
| (15) | H | H | H | H | (d1) | |
| (16) | H | H | H | $CH_3$ | (d1) | |
| (17) | H | 3-$OCH_3$ | 3-$OCH_3$ | $OCH_3$ | (e1)* | |
| (18) | H | 4-t-Bu | H | Cl | (f1) | |
| (19) | 4-$OC_2H_5$ | H | H | H | (g1) | |
| (20) | H | 4-n-Pr | 4-n-Pr | H | (h1) | |

*bonding position: 1, 4-positions

The results are set forth in Table 4. This shows that Compounds (11) to (20) of formula (II) can provide a long luminescent life and an excellent storage stability.

DEVICE EXAMPLE 4

Organic EL devices were prepared and evaluated in the same manner as in Device Example 1 except that the following compounds of formula (III) were used as hole-transporting materials.

| Compound No. | Formula (III) | | | | |
| --- | --- | --- | --- | --- | --- |
| | $R_{31}$ | $R_{32}$ | $R_{33}$ | $R_{34}$ | $A_2$ |
| (21) | H | H | H | H | (j1) |
| (22) | H | 4-$CH_3$ | 4-$CH_3$ | H | (j1) |
| (23) | 4-t-Bu | 4-t-Bu | H | H | (j1) |
| (24) | H | 4-$CH_3$ | 4-$OCH_3$ | H | (k1) |
| (25) | 4-$CH_3$ | H | 4-n-Bu | H | (k1) |
| (26) | H | H | H | H | (l1) |
| (27) | 4-t-Bu | 4-t-Bu | 4-t-Bu | H | (l1) |
| (28) | H | 4-t-Bu | 4-t-Bu | H | (m1) |
| (29) | 4-$C_6H_5$ | 4-$CH_3$ | 4-$CH_3$ | H | (n1) |
| (30) | H | 4-$OCH_3$ | H | Cl | (n1) |

The obtained results are shown in Table 5. This shows that Compounds (21) to (30) of formula (III) can provide a long luminescent life and an excellent storage stability.

DEVICE EXAMPLE 5

Organic EL devices were prepared and evaluated in the same manner as in Device Example 1 except that the following compounds of formula (IV) were used as hole-transporting materials.

| Compound No. | Formula (IV) | | | | |
| --- | --- | --- | --- | --- | --- |
| | $R_{41}$ | $R_{42}$ | $R_{43}$ | $A_3$ | $R_{44}$ |
| (31) | H | H | H | (a2) | |
| (32) | H | H | H | (b2) | |
| (33) | H | H | Cl | (b2) | |
| (34) | H | H | H | (c2) | H |
| (35) | 4-t-Bu | 4-t-Bu | H | (c2) | H |
| (36) | 4-t-Bu | 4-t-Bu | H | (d2) | |
| (37) | 4-$C_6H_5$ | 4-$C_6H_5$ | H | (e2) | |
| (38) | 4-(p-$CH_3$—$C_6H_4$) | 4-(p-$CH_3$—$C_6H_4$) | H | (f2) | |
| (39) | 4-$OCH_3$ | 4-$OCH_3$ | H | (g2) | |
| (40) | H | H | Cl | (h2) | |
| (41) | 4-$CH_3$ | 4-$CH_3$ | H | (i2) | |

The results are set forth in Table 6. This shows that Compounds (31) to (41) of formula (IV) provide a long luminescent life and an excellent storage stability.

DEVICE EXAMPLE 6

Organic EL devices were prepared and evaluated in the same manner as in Device Example 1 except that the following compounds of formula (V) were used as hole-transporting materials.

| Compound No. | Formula (V) | | | |
| --- | --- | --- | --- | --- |
| | $R_{51}$ | $R_{52}$ | $R_{53}$ | $A_4$ |
| (42) | H | H | H | (j2) |
| (43) | H | H | H | (k2) |
| (44) | H | H | $OCH_3$ | (k2) |
| (45) | 4-t-Bu | 4-t-Bu | H | (k2) |
| (46) | H | H | H | (l2) |
| (47) | 4-$CH_3$ | 4-$CH_3$ | H | (l2) |
| (48) | H | 4-$C_6H_5$ | H | (l2) |
| (49) | 4-$CH_3$ | 4-$C_6H_5$ | H | (m2) |
| (50) | 3-$CH_3$ | H | Cl | (m2) |
| (51) | 4-$CH_3$ | 3-$CH_3$ | H | (n2) |
| (52) | 3-t-Bu | 3-$OCH_3$ | H | (n2) |

The obtained results are shown in Table 7. This shows that the amine compounds (42) to (52) of the present invention can provide a long luminescent life and an excellent storage stability.

DEVICE EXAMPLE 7

EL devices were prepared and evaluated in the same manner as in Device Example 1 except that the following compounds of formula (VI) were used as hole-transporting materials, respectively.

| Compound No. | Formula (VI) | | |
| --- | --- | --- | --- |
| | $R_{61}$ | $R_{62}$ | $R_{63}$ |
| (53) | H | H | H |
| (54) | 4-$CH_3$ | 4-$CH_3$ | H |
| (55) | H | H | $CH_3$ |
| (56) | 4-$CH_3$ | 4-$CH_3$ | $CH_3$ |
| (57) | 4-t-Bu | 4-t-Bu | H |
| (58) | 4-t-Bu | 4-t-Bu | $CH_3$ |
| (59) | 4-i-Bu | 4-i-Bu | H |
| (60) | 3-$C_6H_5$ | 3-$C_6H_5$ | H |
| (61) | 4-(p-$CH_3$—$C_6H_4$) | 4-(p-$CH_3$—$C_6H_4$) | $OCH_3$ |

-continued

| Compound No. | Formula (VI) | | |
|---|---|---|---|
| | $R_{61}$ | $R_{62}$ | $R_{63}$ |
| (62) | 4-OCH$_3$ | 4-OCH$_3$ | H |
| (63) | 4-CH$_3$ | 4-CH$_3$ | Cl |

The results are set forth in Table 8. This shows that Compounds (53) to (63) of formula (VI) can provide a long luminescent life and an excellent storage stability.

TABLE 3

| Compound No. | Luminescence (cd/m$_2$) | Luminescent life (Hr) | Storage stability (Hr) |
|---|---|---|---|
| (2) | 3,200 | 560 | 1,400 |
| (3) | 2,800 | 670 | 1,600 |
| (4) | 4,100 | 650 | 1,100 |
| (5) | 2,500 | 700 | 2,100 |
| (6) | 3,700 | 460 | 1,800 |
| (7) | 2,000 | 600 | 2,200 |
| (8) | 3,200 | 450 | 1,900 |
| (9) | 4,000 | 590 | 1,700 |
| (10) | 3,600 | 570 | 2,200 |

TABLE 4

| Compound No. | Luminescence (cd/m$_2$) | Luminescent life (Hr) | Storage stability (Hr) |
|---|---|---|---|
| (11) | 3,400 | 760 | 3,900 |
| (12) | 2,800 | 490 | 2,200 |
| (13) | 2,700 | 550 | 2,000 |
| (14) | 3,000 | 450 | 2,400 |
| (15) | 2,000 | 520 | 1,800 |
| (16) | 1,900 | 750 | 1,200 |
| (17) | 2,700 | 490 | 3,900 |
| (18) | 2,800 | 480 | 2,200 |
| (19) | 2,300 | 410 | 2,100 |
| (20) | 3,300 | 580 | 2,200 |

TABLE 5

| Compound No. | Luminescence (cd/m$^2$) | Luminescent life (Hr) | Storage stability (Hr) |
|---|---|---|---|
| (21) | 3,100 | 580 | 2,100 |
| (22) | 2,700 | 660 | 3,500 |
| (23) | 1,950 | 590 | 3,700 |
| (24) | 2,200 | 790 | 3,000 |
| (25) | 2,500 | 630 | 4,300 |
| (26) | 2,600 | 670 | 2,600 |
| (27) | 2,050 | 850 | 2,900 |
| (28) | 2,800 | 680 | 4,200 |
| (29) | 2,450 | 900 | 3,400 |
| (30) | 1,900 | 690 | 4,100 |

TABLE 6

| Compound No. | Luminescence (cd/m$^2$) | Luminescent life (Hr) | Storage stability (Hr) |
|---|---|---|---|
| (31) | 1,400 | 700 | 2,100 |
| (32) | 1,200 | 570 | 2,050 |
| (33) | 2,000 | 680 | 2,600 |
| (34) | 2,600 | 1050 | 3,500 |
| (35) | 2,150 | 1,100 | 2,900 |
| (36) | 2,100 | 620 | 3,200 |
| (37) | 2,300 | 510 | 2,400 |
| (38) | 1,550 | 480 | 2,200 |

TABLE 6-continued

| Compound No. | Luminescence (cd/m$^2$) | Luminescent life (Hr) | Storage stability (Hr) |
|---|---|---|---|
| (39) | 1,700 | 490 | 2,500 |
| (40) | 2,150 | 570 | 2,100 |
| (41) | 2,200 | 560 | 2,800 |

TABLE 7

| Compound No. | Luminescence (cd/m$^2$) | Luminescent life (Hr) | Storage stability (Hr) |
|---|---|---|---|
| (42) | 2,200 | 700 | 3,000 |
| (43) | 2,000 | 650 | 3,000 |
| (44) | 1,900 | 600 | 2,850 |
| (45) | 2,150 | 550 | 3,200 |
| (46) | 2,500 | 790 | 2,800 |
| (47) | 2,350 | 590 | 2,500 |
| (48) | 2,400 | 620 | 3,600 |
| (49) | 2,550 | 740 | 4,900 |
| (50) | 2,770 | 650 | 3,750 |
| (51) | 2,250 | 830 | 4,100 |
| (52) | 2,400 | 790 | 3,800 |

TABLE 8

| Compound No. | Luminescence (cd/m$^2$) | Luminescent life (Hr) | Storage stability (Hr) |
|---|---|---|---|
| (53) | 1,500 | 950 | 2,700 |
| (54) | 1,800 | 560 | 2,900 |
| (55) | 2,750 | 470 | 4,200 |
| (56) | 2,100 | 750 | 3,100 |
| (57) | 2,800 | 640 | 3,300 |
| (58) | 1,400 | 760 | 2,800 |
| (59) | 1,700 | 650 | 2,500 |
| (60) | 2,200 | 520 | 2,100 |
| (61) | 2,100 | 690 | 2,800 |
| (62) | 1,300 | 500 | 2,000 |
| (63) | 1,500 | 700 | 2,450 |

DEVICE EXAMPLE 8

An EL device was prepared in the same manner as in Device Example 1 except that Compound (13) of formula (II) (wherein $R_{21}$ is H, $R_{22}$ is H, $R_{23}$ is H, $R_{24}$ is H, $R_{25}$ is H, and $A_1$=(c1)) and Compound (4) of formula (I) (wherein $R_{11}$ is 4-t-Bu, $R_{12}$ is H, and $R_{13}$ H) were vacuum-evaporated as hole-transporting materials at the same time. The EL device thus prepared was then evaluated for properties. It exhibited a luminescence of 3,300 cd/m$^2$, a luminescent life of 720 hours and a storage stability of 2,900 hours. The results show that the hole-transporting layer formed by the simultaneous vacuum evaporation of Compound (13) and Compound (4) can provide a long luminescent life and an excellent luminescence stability.

DEVICE EXAMPLE 9

An EL device was prepared in the same manner as in Device Example 1 except that Compound (21) of formula (III) (wherein $R_{31}$ is H, $R_{32}$ is H, $R_{33}$ is H, $R_{34}$ is H, and $A_2$ is (J1)) and Compound (46) of formula (V) (wherein $R_{51}$ is H, $R_{52}$ is H, $R_{53}$ is H, and $A_4$ is (12)) were vacuum-evaporated as hole-transporting materials at the same time. The EL device thus prepared was then evaluated for properties. It exhibited a luminescence of 2,430 cd/m$^2$, a luminescent life of 1110 hours and a storage stability of 4,800 hours. The results show that the hole-transporting layer formed by the simultaneous vacuum evaporation of Compound (21) of formula (III) and Compound (46) of formula (V) can provide a long luminescent life and an excellent luminescence stability.

DEVICE EXAMPLE 10

An EL device was prepared in the same manner as in Device Example 1 except that Compound (13) of formula (II) (wherein $R_{21}$ is H, $R_{22}$ is H, $R_{23}$ is H, $R_{24}$ is H, $R_{25}$ is H, and $A_1$ is (c1)) was used as a hole-transporting material and purified triazole was used as an electron-transporting material. The EL device thus prepared was then evaluated for properties. In this case, since triazole exhibits high hole blocking properties, the hole-transporting material was observed to emit blue light. The EL device thus obtained exhibited a luminescence of 200 cd/m², a luminescent life of 300 hours and a storage stability of 2,700 hours. For comparison, another EL device was prepared in the same manner as above except that TPD was used as a hole-transporting material. The EL device thus obtained was examined for properties. The EL device prepared from TPD exhibited a luminescence of 100 cd/m², a luminescent life of 110 hours and a storage stability of 410 hours. The results show that Compound (13) of formula (II) can provide a long luminescent life and an excellent luminescence stability.

As mentioned above, the electro-luminescence device of the present invention comprises a compound according to the present invention as a hole-transporting layer to provide drastic improvements in luminescence stability and storage stability as compared with the conventional organic EL devices which find greatest difficulty in these properties.

While the invention has been described in detail and with reference to specific embodiments thereof, it will be apparent to one skilled in the art that various changes and modifications can be made therein without departing from the spirit and scope thereof.

What is claimed is:

1. An electro-luminescence device, comprising a pair of electrodes in a region provided therebetween, said region performing hole-transporting, light emitting and electron-transporting, said region comprising at least one of the compounds having the formula (I) to (V):

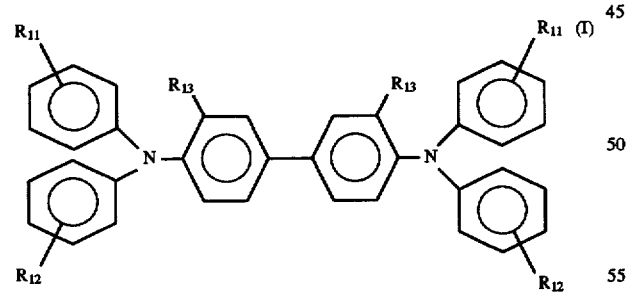

wherein $R_{11}$ and $R_{12}$ may be the same or different and each represent a hydrogen atom, a lower alkyl group, a lower alkoxy group, a phenyl group, or a phenyl group having a lower alkyl group or a lower alkoxy group as a substituent (s), with the proviso that at least one of $R_{11}$ and $R_{12}$ is a normal butyl group, an isobutyl group, a secondary butyl group, a tertiary butyl group, a phenyl group, or a phenyl group having a lower alkyl group or a lower alkoxy group; and and $R_{13}$ represents a hydrogen represents a hydrogen atom, a lower alkyl group, a lower alkoxy group or a chlorine atoms:

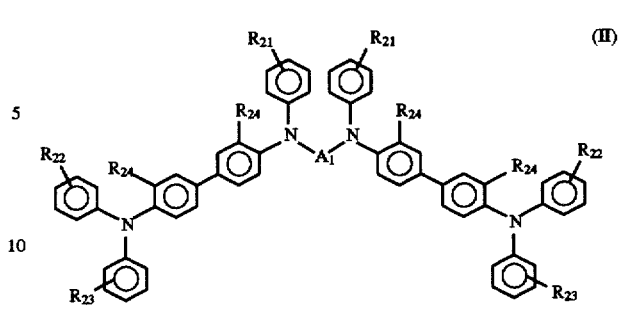

wherein $R_{21}$, $R_{22}$ and $R_{23}$ may be the same or different and each represent a hydrogen atom, a lower alkyl group, a lower alkoxy group, an unsubstituted phenyl group, or a phenyl group having a lower alkyl group or a lower alkoxy group as a substituent(s); $R_{24}$ represents a hydrogen atom, a lower alkyl group, a lower alkoxy group or a chlorine atom; and $A_1$ represents a group represented by any one of the following structural formulae (a1) to (i1);

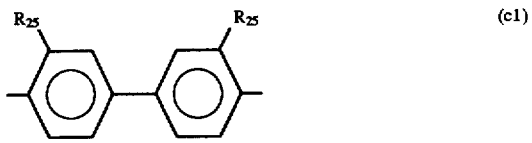

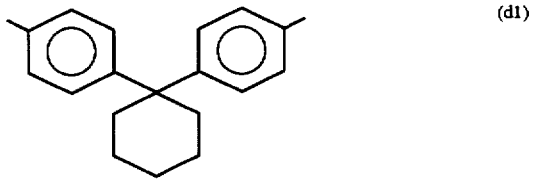

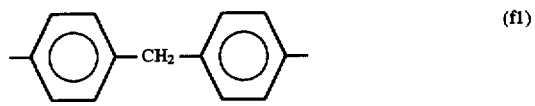

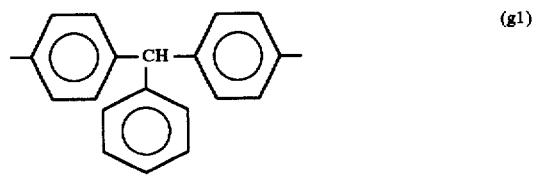

-continued

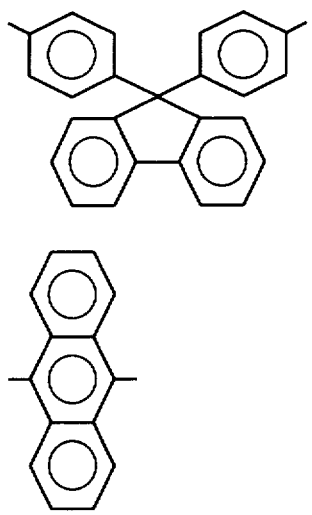

in which $R_{25}$ represents a hydrogen atom, a lower alkyl group, a lower alkoxy group or a chlorine atom;

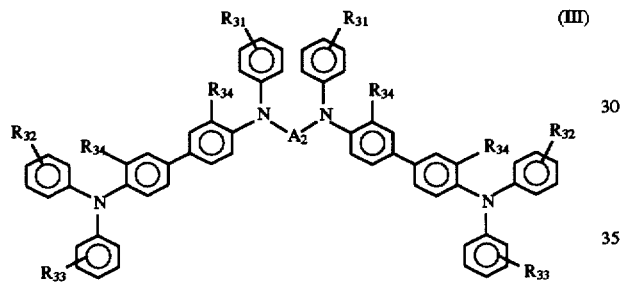
(III)

wherein $R_{31}$, $R_{32}$ and $R_{33}$ may be the same or different and each represent a hydrogen atom, a lower alkyl group or a lower alkoxy group, an unsubstituted phenyl group, or a phenyl group having a lower alkyl group or a lower alkoxy group as a substituent(s); $R_{34}$ represents a hydrogen atom, a lower alkyl group, a lower alkoxy group or a chlorine atom; and $A_2$ represents a group represented by any one of the following formulae (j1) to (n1);

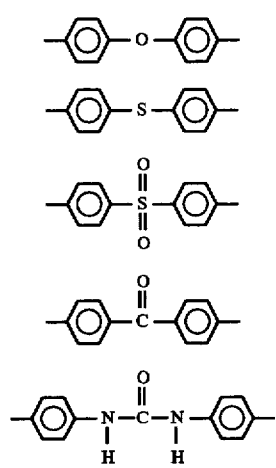

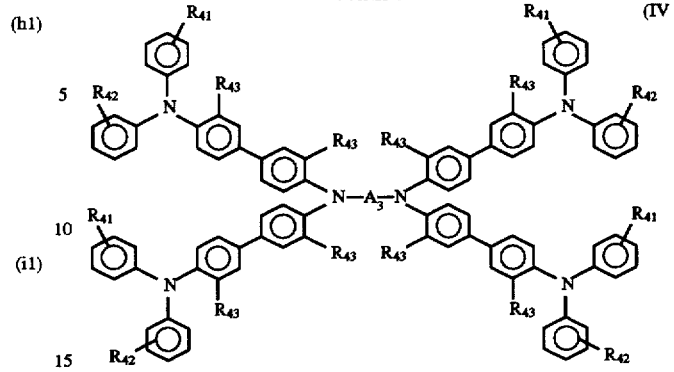
(IV)

wherein $R_{41}$ and $R_{42}$ may be the same or different and each represent a hydrogen atom, a lower alkyl group, a lower alkoxy group, an unsubstituted phenyl group, or a phenyl group having a lower alkyl group or a lower alkoxy group as a substituent(s); $R_{43}$ represents a hydrogen atom, a lower alkyl group, a lower alkoxy group or a chlorine atom; and $A_3$ represents a group represented by any one of the following structural formulae (a2) to (i2);

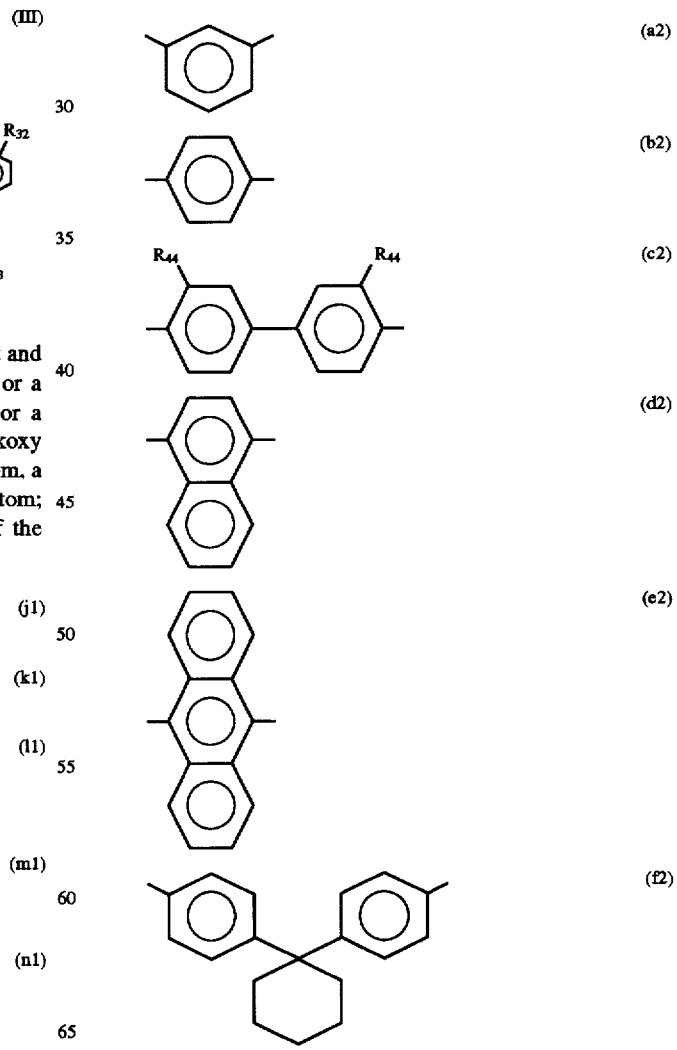

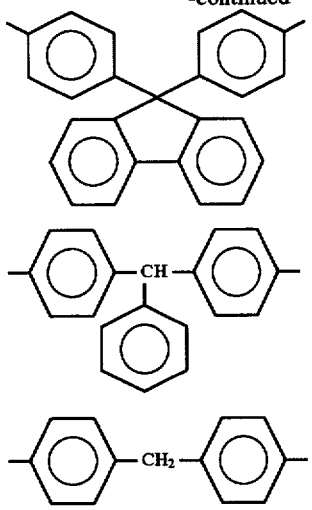

in which $R_{44}$ represents a hydrogen atom, a lower alkyl group, a lower alkoxy group or a chlorine atom;

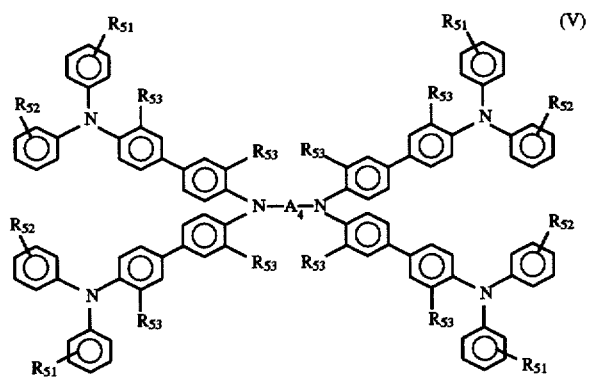
(V)

wherein $R_{51}$ and $R_{52}$ may be the same or different and each represent a hydrogen atom, a lower alkyl group or a lower alkoxy group, an unsubstituted phenyl group, or a phenyl group having a lower alkyl group or a lower alkoxy group as a substituent(s); $R_{53}$ represents a hydrogen atom, a lower alkyl group, a lower alkoxy group or a chlorine atom; and $A_4$ represents a group represented by any one of the following formulae (j2) to (n2);

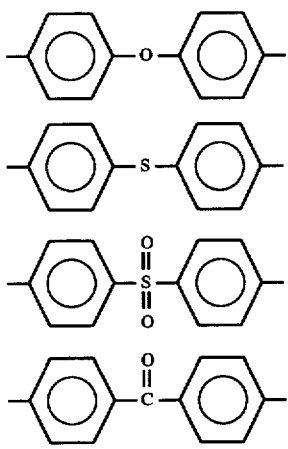

(j2)
(k2)
(l2)
(m2)

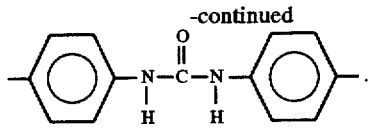
(n2)

2. The electro-luminescence device according to claim 1, wherein said region comprises a hole-transporting layer, a light emitting layer and an electron-transporting layer.

3. The electro-luminescence device according to claim 2, wherein said hole-transporting layer comprises at least two selected from the group consisting of the compounds represented by formulas (I) through (V):

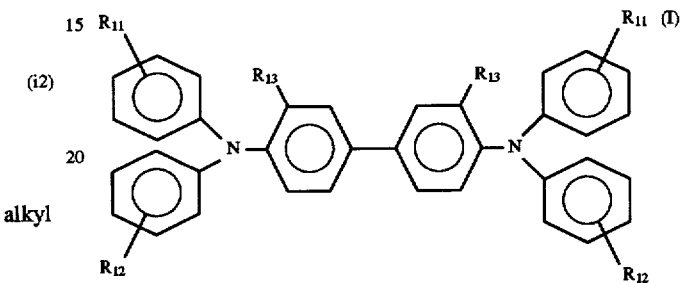
(I)

wherein $R_{11}$ and $R_{12}$ may be the same or different and each represent a hydrogen atom, a lower alkyl group, a lower alkoxy group, a phenyl group, or a phenyl group having a lower alkyl group or a lower alkoxy group as a substituent (s), with the proviso that at lest one of $R_{11}$ and $R_{12}$ is a normal butyl group, an isobutyl group, a secondary butyl group, a tertiary butyl group, a phenyl group, or a phenyl group having a lower alkyl group or a lower alkoxy group; and and $R_{13}$ represents a hydrogen represents a hydrogen atom, a lower alkyl group, a lower alkoxy group or a chlorine atoms:

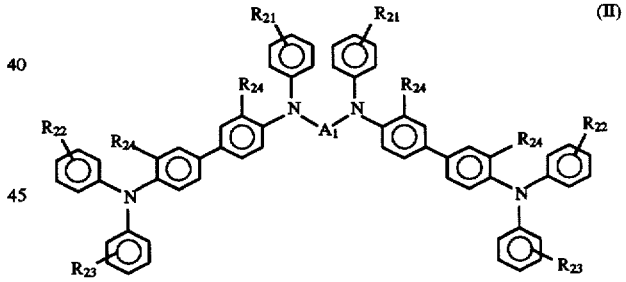
(II)

wherein $R_{21}$, $R_{22}$ and $R_{23}$ may be the same or different and each represent a hydrogen atom, a lower alkyl group, a lower alkoxy group, an unsubstituted phenyl group, or a phenyl group having a lower alkyl group or a lower alkoxy group as a substituent(s); $R_{24}$ represents a hydrogen atom, a lower alkyl group, a lower alkoxy group or a chlorine atom; and $A_1$ represents a group represented by any one of the following structural formulae (a1) to (i1);

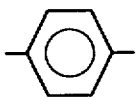
(a1)

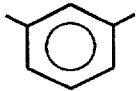
(b1)

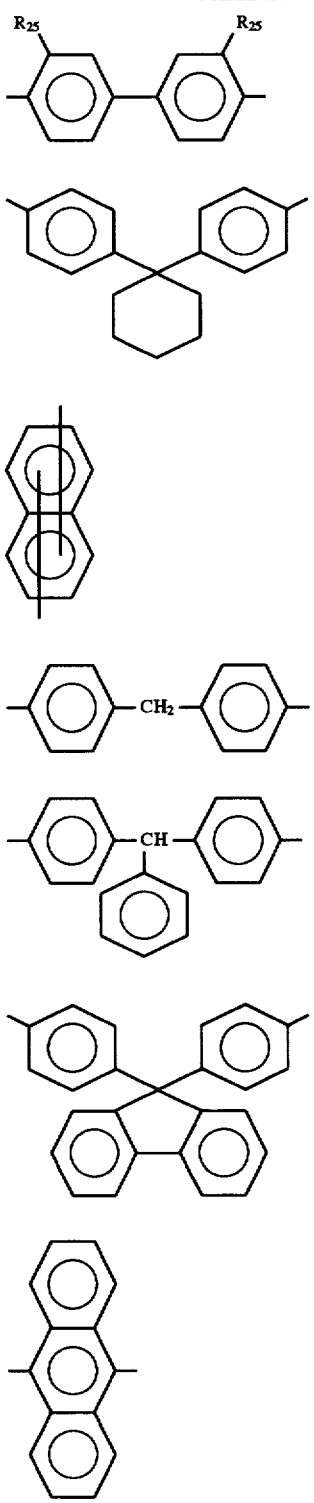

in which $R_{25}$ represents a hydrogen atom, a lower alkyl group, a lower alkoxy group or a chlorine atom;

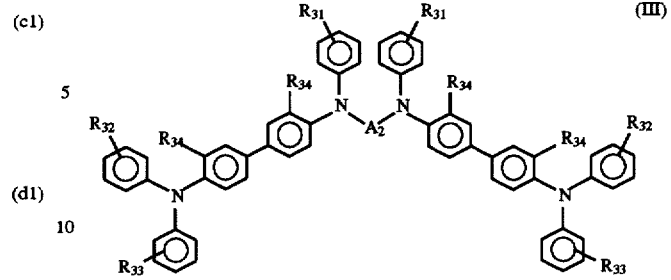

wherein $R_{31}$, $R_{32}$ and $R_{33}$ may be the same or different and each represent a hydrogen atom, a lower alkyl group or a lower alkoxy group, an unsubstituted phenyl group, or a phenyl group having a lower alkyl group or a lower alkoxy group as a substituent(s); $R_{34}$ represents a hydrogen atom, a lower alkyl group, a lower alkoxy group or a chlorine atom; and $A_2$ represents a group represented by any one of the following formulae (j1) to (n1);

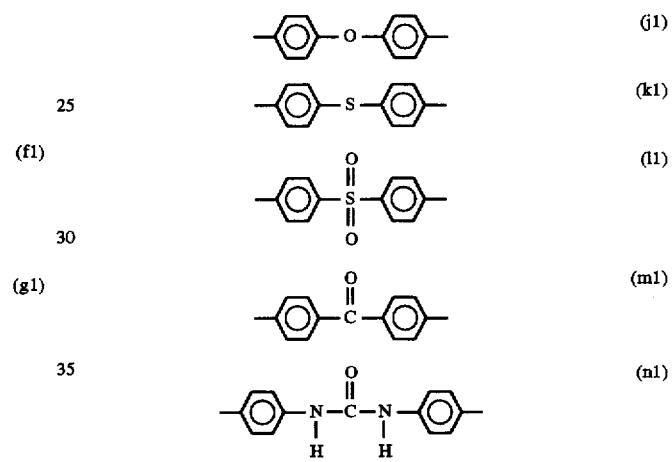

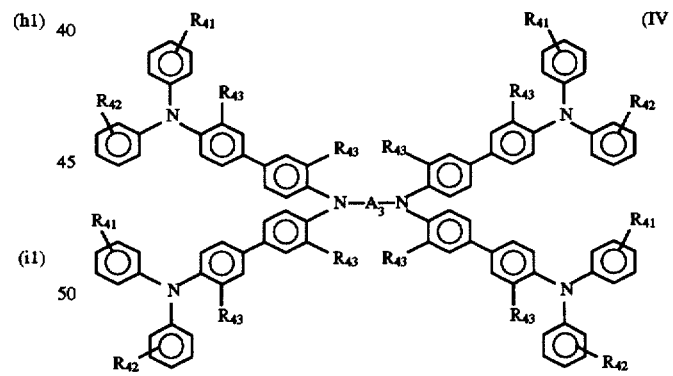

wherein $R_{41}$ and $R_{42}$ may be the same or different and each represent a hydrogen atom, a lower alkyl group, a lower alkoxy group, an unsubstituted phenyl group, or a phenyl group having a lower alkyl group or a lower alkoxy group as a substituent(s); $R_{43}$ represents a hydrogen atom, a lower alkyl group, a lower alkoxy group or a chlorine atom; and $A_3$ represents a group represented by any one of the following structural formulae (a2) to (i2);

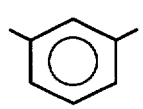

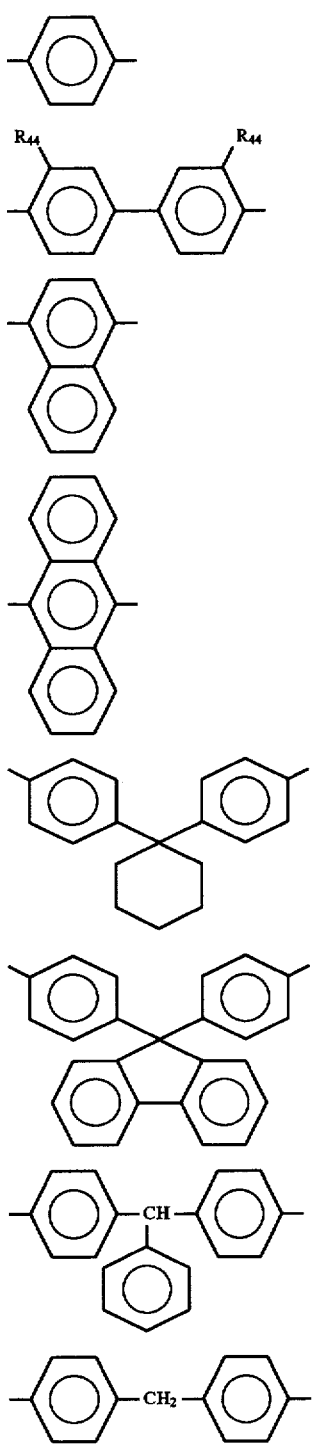

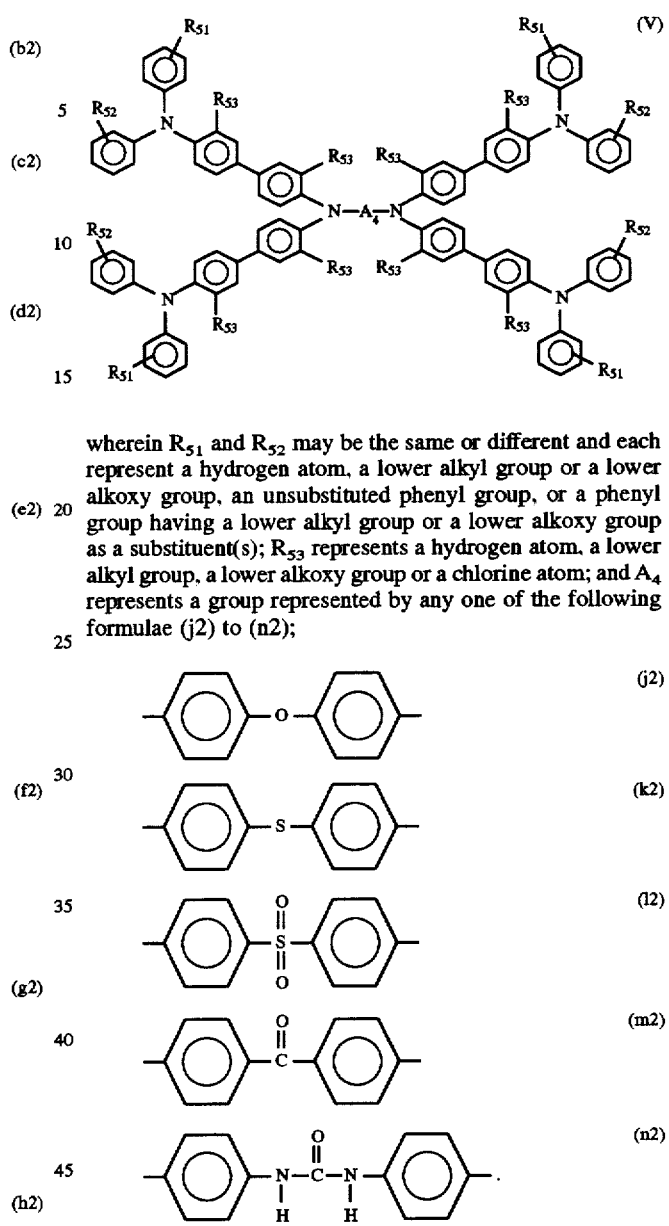

in which $R_{44}$ represents a hydrogen atom, a lower alkyl group, a lower alkoxy group or a chlorine atom;

wherein $R_{51}$ and $R_{52}$ may be the same or different and each represent a hydrogen atom, a lower alkyl group or a lower alkoxy group, an unsubstituted phenyl group, or a phenyl group having a lower alkyl group or a lower alkoxy group as a substituent(s); $R_{53}$ represents a hydrogen atom, a lower alkyl group, a lower alkoxy group or a chlorine atom; and $A_4$ represents a group represented by any one of the following formulae (j2) to (n2);

4. The electro-luminescence device according to claim 2, wherein said hole-transporting layer also serves as said light emitting layer.

5. The electro-luminescence device according to claim 2, wherein said electron-transporting layer also serves as said light emitting layer.

* * * * *